United States Patent [19]
Anilionis et al.

[11] Patent Number: 5,196,338
[45] Date of Patent: Mar. 23, 1993

[54] **RECOMBINANT VECTORS FOR *HAEMOPHILUS INFLUENZAE* PEPTIDES AND PROTEINS**

[75] Inventors: Algis Anilionis, Pittsford, N.Y.; Robert C. Seid, Jr., San Francisco, Calif.; Robert A. Deich, Rochester, N.Y.; Gary W. Zlotnick, Penfield, N.Y.; Bruce A. Green, Pittsford, N.Y.

[73] Assignee: Praxis Biologics, Inc., Rochester, N.Y.

[21] Appl. No.: 480,396

[22] Filed: Feb. 15, 1990

Related U.S. Application Data

[60] Division of Ser. No. 396,572, Aug. 21, 1989, abandoned, which is a continuation-in-part of Ser. No. 239,572, Sep. 1, 1988, Pat. No. 5,098,997, which is a continuation-in-part of Ser. No. 132,073, Dec. 11, 1987, abandoned, which is a continuation-in-part of Ser. No. 20,849, Mar. 2, 1987, abandoned, which is a continuation-in-part of Ser. No. 948,364, Dec. 31, 1986, abandoned.

[51] Int. Cl.5 .................... C12N 15/62; C12N 15/31; C12N 15/63
[52] U.S. Cl. .................... 435/252.3; 435/69.1; 435/69.7; 435/320.1; 530/350
[58] Field of Search .................... 435/69.1, 69.7, 252.3, 435/320.1; 424/88; 530/350, 806

[56] References Cited

U.S. PATENT DOCUMENTS 5,098,997 3/1992 Anilionis et al. .................... 530/350
5,110,908 5/1992 Deich et al. .................... 530/403

OTHER PUBLICATIONS

Science 222:778–782, Nov. 18, 1983, Young et al., Yeast RNA Polymerase II Genes: Isolation with Antibody Probes.
J. Infect. Diseases 152: 1300–1307, Dec. 1985, Murphy et al., Identification of a Specific Epitope of *Haemophilus influenzae* on a 16,600 Dalton Outer Membrane Protein.
Bio/Technology 3: 323–326, Apr. 1985, Valenzuela et al., Antigen Engineering in Yeast: Synthesis and Assembly of Hybrid Hepatitis B Surface Antigen–Herpes Simplex 1 gD Particles.
Infect. and Immun. 49: 544–549, Sep. 1985, Munson et al., Purification and Partial Characterization of Outer Membrane Proteins P5 and P6 from *Haemophilus influenzae* Type b.

*Primary Examiner*—David L. Lacey
*Assistant Examiner*—John D. Ulm
*Attorney, Agent, or Firm*—Alan M. Gordon; Geraldine F. Baldwin

[57] ABSTRACT

Peptides and proteins related to an epitope comprising an outer membrane protein of *Haemophilus influenzae* are described. The peptides and proteins can be prepared by methods including novel and improved methods of purification from *H. influenzae* cultures, and by recombinant DNA and chemical synthetic techniques. Additionally, recombinant vectors containing nucleotide sequences encoding PBOMP-1 and PBOMP-2 related peptides, proteins and fusion proteins are also described. Recombinant vectors include plasmid DNA and viral DNA such as human viruses, animal viruses, insect viruses and bacteriophages that direct the expression of the PBOMP-1 and PBOMP-2 related peptides, proteins, and fusion proteins in appropriate host cells. The peptides, proteins, fusion proteins and viruses both "live" and "inactivated" are used as immunogens in vaccine formulations to protect against *H. influenzae* infections. The peptides, proteins and fusion proteins are also used as reagents in immunoassays as well as to prepare immunoglobulins for passive immunization. Use of the nucleotide sequences encoding the PBOMP related peptides, proteins and fusion proteins in hybridization assays is also described.

19 Claims, 33 Drawing Sheets

```
ATG AAC AAA TTT GTT AAA TCA TTA TTA GTT GCA GGT TCT GTA GCT GCA TTA GCA GCT TGT
Met Asn Lys Phe Val Lys Ser Leu Leu Val Ala Gly Ser Val Ala Ala Leu Ala Ala Cys

AGT TCA TCT AAC AAC GAT GCT GCA GGC AAT GGT GCT GCT CCA ACT TTT GGC GGT TAC TCT
Ser Ser Ser Asn Asn Asp Ala Ala Gly Asn Gly Ala Ala Gln Thr Phe Gly Gly Tyr Ser

GTT GCT GAT CTT CAA CAA CGT TAC AAT ACC GTT TAT TTC GGT TTT GAT AAA TAT GAC ATT
Val Ala Asp Leu Gln Gln Arg Tyr Asn Thr Val Try Phe Gly Phe Asp Lys Tyr Asp Ile

ACT GGT GAA TAC GTT CAA ATC TTA GAT GCG CAC GCT GCA TAT TTA AAT GCA ACA CCA GCT
Thr Gly Glu Tyr Val Gln Ile Leu Asp Ala His Ala Ala Tyr Leu Asn Ala Thr Pro Ala

GCT AAA GTA TTA GTA GAA GGT AAC ACT GAT GAA CGT GGT ACA CCA GAA TAC AAC ATC GCA
Ala Lys Val Leu Val Glu Gly Asn Thr Asp Glu Arg Gly Thr Pro Glu Tyr Asn Ile Ala

TTA GGC CAA CGT CGT GCA GAT GCA GTT AAA GGT TAT TTA GCT GGT AAA GGT GTT GAT GCT
Leu Gly Gln Arg Arg Ala Asp Ala Val Lys Gly Tyr Leu Ala Gly Lys Gly Val Asp Ala

GGT AAA TTA GGC ACA GTA TCT TAC GGT GAA GAA AAA CCT GCA GTA TTA GGT CAT GAT GAA
Gly Lys Leu Gly Thr Val Ser Tyr Gly Glu Glu Lys Pro Ala Val Leu Gly His Asp Glu

GCT GCA TAT TCT AAA AAC CGT CGT GCA GTG TTA GCG TAC TAA
Ala Ala Tyr Ser Lys Asn Arg Arg Ala Val Leu Ala Tyr End
```

FIG. I

FIG. 10

```
         10         20         30         40         50         60
AGATCTCACA ACGGGCGTTT CAGAGGTACT TAGTACATCT TTTCTAGGCG AAAGTCCAAG 70         80         90        100        110        120
CCTCTCTCCA AATGGAATTA TGATTATTTA TAGTTCTACA CAGGGCTTAG GAAAGGTGCT 130        140        150        160        170        180
ACAATTGGTT TCTGCAGATG GTCGCTTTAA GGCGAGCCTT CCAGGAAGTG ATGGTCAAGT 190        200        210        220        230        240
TAAATTTCCA GCTTGGTCTC CATACTTAAC TAAATAAAAA ACTCATTTAG GAGAAATCTA 250        260        270        280        290        300
ATGAACAAAT TTGTTAAATC ATTATTAGTT GCAGGTTCTG TAGCTGCATT AGCAGCTTGT 310        320        330        340        350        360
AGTTCATCTA ACAACGATGC TGCAGGCAAT GGTGCTGCTC AAACTTTTGG CGGTTACTCT 370        380        390        400        410        420
GTTGCTGATC TTCAACAACG TTACAATACC GTTTATTTCG GTTTTGATAA ATATGACATT 430        440        450        460        470        480
ACTGGTGAAT ACGTTCAAAT CTTAGATGCG CACGCTGCAT ATTTAAATGC AACACCAGCT 490        500        510        520        530        540
GCTAAAGTAT TAGTAGAAGG TAACACTGAT GAACGTGGTA CACCAGAATA CAACATCGCA 550        560        570        580        590        600
TTAGGCCAAC GTCGTGCAGA TGCAGTTAAA GGTTATTTAG CTGGTAAAGG TGTTGATGCT 610        620        630        640        650        660
GGTAAATTAG GCACAGTATC TTACGGTGAA GAAAAACCTG CAGTATTAGG TCATGATGAA 670        680        690        700        710        720
GCTGCATATT CTAAAAACCG TCGTGCAGTG TTAGCGTACT AATTCTTAAT ATTTCTAATA

730
CTTGAAAAAC AGGATCC
```

FIG. 11

```
ATG AAC AAA TTT GTT AAA TCA TTA TTA GTT GCA GGT TCT GTA GCT GCA TTA GCA GCT TGT
Met Asn Lys Phe Val Lys Ser Leu Leu Val Ala Gly Ser Val Ala Ala Leu Ala Ala Cys

AGT TCA TCT AAC AAC GAT GCT GCA GGC AAT GGT GCT CCA ACT TTT GGC GGT TAC TCT
Ser Ser Ser Asn Asn Asp Ala Ala Gly Asn Gly Ala Ala Gln Thr Phe Gly Gly Tyr Ser

GTT GCT GAT CTT CAA CAA CGT TAC AAT ACC GTT TAT TTC GGT TTT GAT AAA TAT GAC ATT
Val Ala Asp Leu Gln Gln Arg Tyr Asn Thr Val Try Phe Gly Phe Asp Lys Tyr Asp Ile

ACT GGT GAA TAC GTT CAA ATC TTA GAT GCG CAC GCT GCA TAT TTA AAT GCA ACA CCA GCT
Thr Gly Glu Tyr Val Gln Ile Leu Asp Ala His Ala Ala Tyr Leu Asn Ala Thr Pro Ala

GCT AAA GTA TTA GTA GAA GGT GCA GAT GCA AAC ACT GAT GAA CGT GGT ACA CCA GAA TAC AAC ATC GCA
Ala Lys Val Leu Val Glu Gly Ala Asp Ala Asn Thr Asp Glu Arg Gly Thr Pro Glu Tyr Asn Ile Ala

TTA GGC CAA CGT CGT GCA GAT GCA GTT AAA GGT TAT TTA GCT GGT AAA GGT GTT GAT GCT
Leu Gly Gln Arg Arg Ala Asp Ala Val Lys Gly Tyr Leu Ala Gly Lys Gly Val Asp Ala

GGT AAA TTA GGC ACA GTA TCT TAC GGT GAA GAA AAA CCT GCA GTA TTA GGT CAT GAT GAA
Gly Lys Leu Gly Thr Val Ser Tyr Gly Glu Glu Lys Pro Ala Val Leu Gly His Asp Glu

GCT GCA TAT TCT AAA AAC CGT CGT GCA GTG TTA GCG TAC TAA
Ala Ala Tyr Ser Lys Asn Arg Arg Ala Val Leu Ala Tyr End
```

FIG. 12

```
PBOMP-1:  tyr-asn-thr-val-tyr-phe-gly-phe-asp-lys-tyr-asp-ile-thr-gly-glu-tyr-
T9:       tyr-asn-thr-val-tyr-phe-gly-phe-asp-lys-tyr-asp-ile-thr-gly-phe-tyr- PBOMP-1:  val-gln-ile-leu-asp-ala-his-ala-ala-tyr-leu-asn-ala-ala-thr-pro-ala-ala
T9:       val-thr-ile-----asp-ala-asp-ala-ala-tyr-leu-asn-ala-ala-thr-pro-ala-ala
```

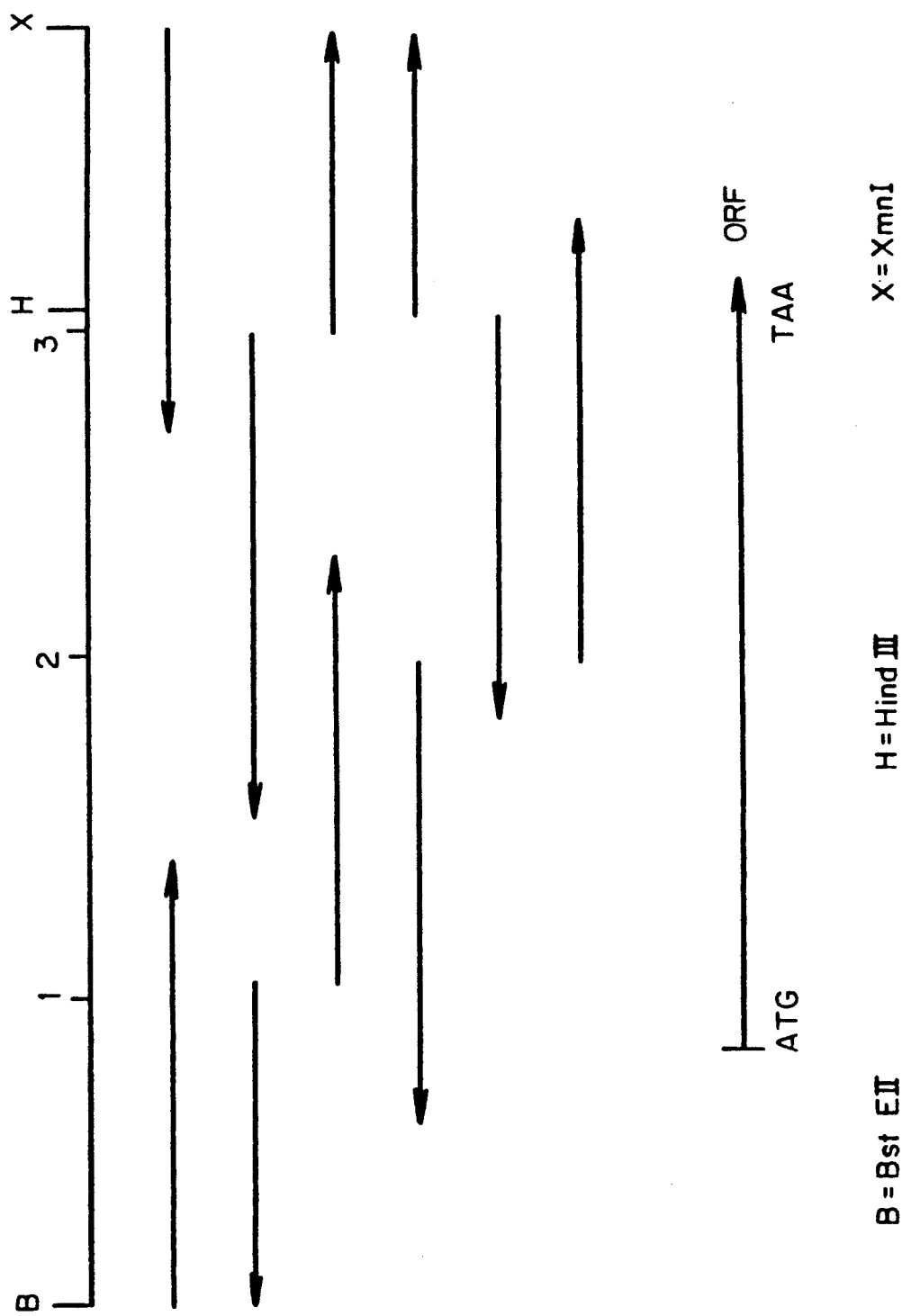

FIG. 14

```
        10         20         30         40         50         60
GGTAACCAGC AGAAAGGATA GGAGGTTGTT ATTGTGCATA AGTATGGTTC AACTTTAGTT 70         80         90        100        110        120
GTTGGTGCTT GTGTTTTAGT ATCTGACAAT GGTAATACTA AAAACATTTC AACTTTTTCT 130        140        150        160        170        180
CCAAGAAACC CACTTTAATT CCTTCTAATA TAGAGAATAT TATATGAAAA AAACAAATAT 190        200        210        220        230        240
GGCATTAGCA CTGTTAGTTG CTTTTAGTGT AACTGGTTGT GCAAATACTG ATATTTTCAG 250        260        270        280        290        300
CGGTGATGTT TATAGCGCAT CTCAAGCAAA GGAAGCGCGT TCAATTACTT ATGGTACGAT 310        320        330        340        350        360
TGTTTCTGTA CGCCCTGTTA AAATTCAAGC TGATAATCAA GGTGTAGTTG GTACGCTTGG 370        380        390        400        410        420
TGGTGGAGCT TTAGGTGGTA TTGCTGGTAG TACAATTGGC GGTGGTCGTG GTCAAGCTAT 430        440        450        460        470        480
TGCAGCAGTA GTTGGTGCAA TTGGCGGTGC AATAGCTGGA AGTAAAATCG AAGAAAAAAT 490        500        510        520        530        540
GAGTCAAGTA AACGGTGCTG AACTTGTAAT TAAGAAAGAT GATGGTCAAG AGATCGTTGT 550        560        570        580        590        600
TGTTCAAAAG GCTGACAGCA GTTTTGTAGC TGGTCGCCGA GTTCGTATTG TTGGTGGCGG 610        620        630        640        650        660
CTCAAGCTTA AATGTTTCTG TGCTATAACC AATAGCATTA AAGTCTAATA TGATTAATCA 670        680        690        700        710        720
GTGTCTTAAC TTAGTAAGGC ACTGATTTTT TTATAATTAA ATTCATTTAA AATATATATT 730        740        750        760        770        780
ATCGTCTATC TAAGATAAAT TTAAAGGACT AAATTAGAAT TTAGTCCTTT AGAAAACTTG

GAATTNNTTC
‿‿‿‿‿‿‿
   XmnI
```

FIG. 15

```
ATG AAA ACA AAT ATG GCA CTG TTA GTT GCT TTT AGT GTA ACT GGT TGT GCA
Met Lys Thr Asn Met Ala Leu Leu Val Ala Phe Ser Val Thr Gly Cys Ala

AAT ACT GAT ATT TTC AGC GGT GAT GTT TAT AGC GCA TCT CAA GCA AAG GAA GCG CGT TCA
Asn Thr Asp Ile Phe Ser Gly Asp Val Tyr Ser Ala Ser Gln Ala Lys Glu Ala Arg Ser

ATT ACT TAT GGT ACG AGT GTT TCT GTA CGC CCT GTT AAA ATT CAA GCT GAT AAT CAA GGT
Ile Thr Tyr Gly Thr Ser Val Ser Val Arg Pro Val Lys Ile Gln Ala Asp Asn Gln Gly

GTA GTT GGT ACG CTT GGT GGA GCT GGT GGT TTA GGT GGT ATT GCT GGT AGT ACA ATT GGC GGT
Val Val Gly Thr Leu Gly Gly Ala Gly Gly Leu Gly Gly Ile Ala Gly Ser Thr Ile Gly Gly

GGT CGT GGT CAA GCT ATT GCA GCA GTA GTT GGT GCA ATT GGC GGT GCA ATA GCT GGA AGT
Gly Arg Gly Gln Ala Ile Ala Ala Val Val Gly Ala Ile Gly Gly Ala Ile Ala Gly Ser

AAA ATC GAA GAA AAA ATG AGT CAA GTA AAC GGT GCT GAA CTT GTA ATT AAG AAA GAT GAT
Lys Ile Glu Glu Lys Met Ser Gln Val Asn Gly Ala Glu Leu Val Ile Lys Lys Asp Asp

GGT CAA GAG ATC GTT GTT CAA AAG GCT GAC AGC AGT TTT GTA GCT CGC CGA GTT
Gly Gln Glu Ile Val Val Val Gln Lys Ala Asp Ser Ser Phe Val Ala Gly Arg Arg Val

CGT ATT GTT GGT GGC TCA AGC TTA AAT GTT TCT GTG CTA TAA
Arg Ile Val Gly Gly Gly Ser Ser Leu Asn Val Ser Val Leu End
```

PBOMP-2 / GLOBOMYCIN

PBOMP-1 / GLOBOMYCIN

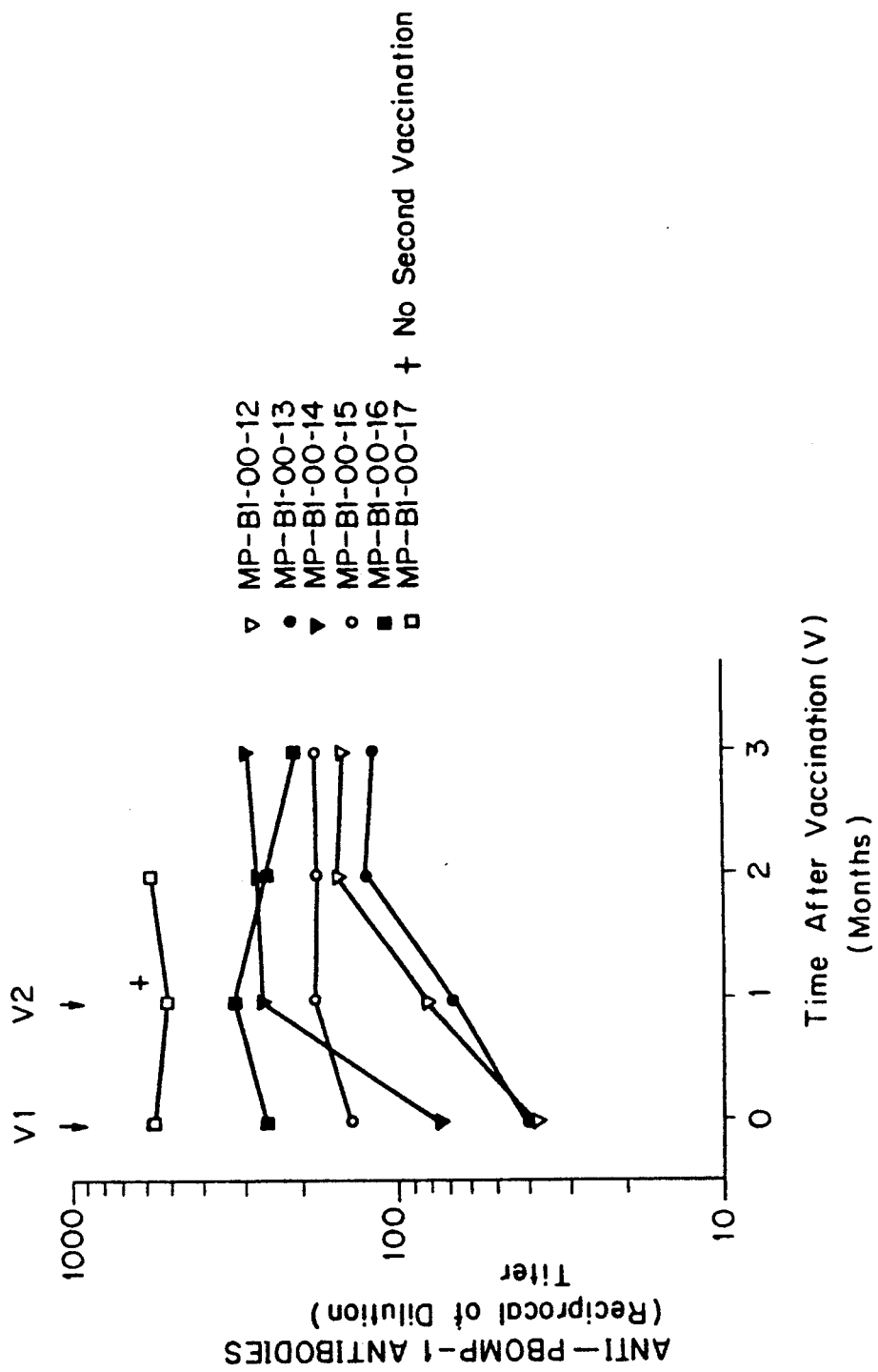

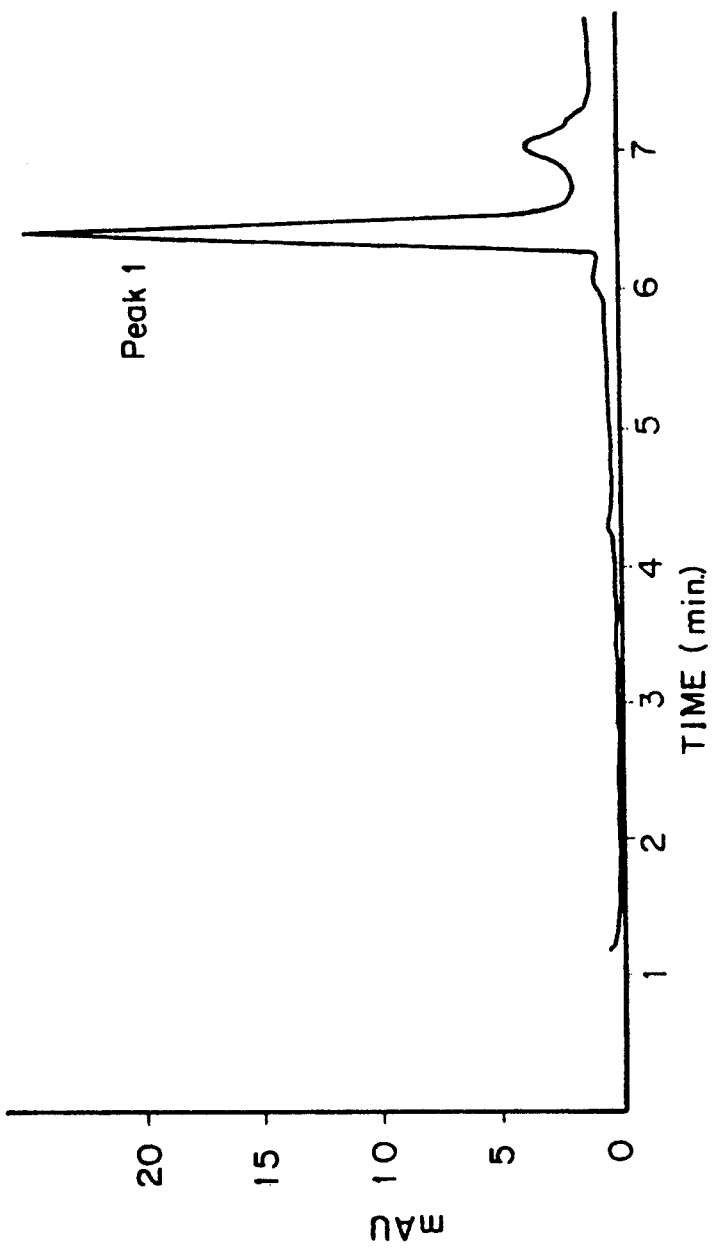
FIG. 22 Elution Pattern of PBOMP-1 on Reverse Phase C-4 Column

FIG. 23A COOMASSIE STAIN
PURIFICATION OF RECOMBINANT PBOMP-1
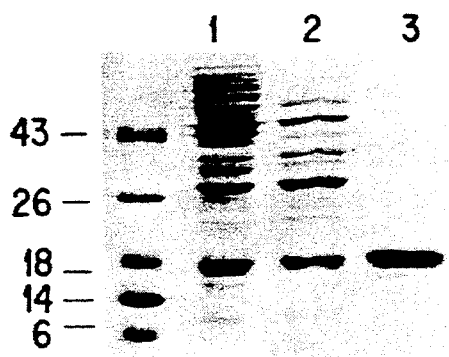
1. Cytoplasmic Fraction
2. Deae Eluate
3. Reverse Phase Eluate
FIG. 23B WESTERN BLOT
PURIFICATION OF RECOMBINANT PBOMP-1
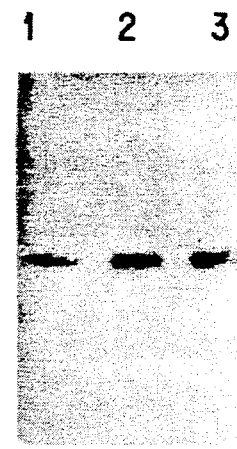
1. Cytoplasmic Fraction
2. Deae Eluate
3. Reverse Phase Eluate

| PEPTIDE | SEQUENCE | SEQUENCE LENGTH | ORIGIN |
|---|---|---|---|
| P1 | $H_2N$-C-S-S-S-N-N-D-A-A-G-N-G-A-A-Q-F-G-G-Y-$CO_2H$ (1–20) | 20 | N-TERMINUS |
| P2 | $H_2N$-D-E-A-A-Y-S-K-N-R-R-A-V-L-A-Y-$CO_2H$ (120–134) | 16 | C-TERMINUS |
| P3 | $H_2N$-K-P-A-V-L-G-H-D-E-A-A-Y-S-K-N-R-R-A-V-L-A-Y-$CO_2H$ (113–134) | 22 | C-TERMINUS |
| P4 | $H_2N$-K-L-G-T-V-S-Y-G-E-E-K-P-A-V-L-G-H-D-E-A-A-Y-S-K-N-R-R-A-V-L-A-Y-$CO_2H$ (103–134) | 32 | C-TERMINUS |
| P5 | $H_2N$-K-G-V-D-A-G-K-L-G-T-V-S-Y-G-E-E-K-P-A-V-L-G-H-D-E-A-A-Y-S-K-N-R-R-A-V-L-A-Y-$CO_2H$ (97–134) | 38 | C-TERMINUS |

FIG. 27

RECOMBINANT VECTORS FOR *HAEMOPHILUS INFLUENZAE* PEPTIDES AND PROTEINS

CROSS REFERENCE TO RELATED APPLICATIONS

This application is a divisional application of copending Ser. No. 07/396,572 filed on Aug. 21, 1989, abandoned, which in turn is continuation-in-part application of copending Ser. No. 239,572 filed on Sep. 1, 1988 now U.S. Pat. No. 5,098,997, which in turn is a continuation-in-part of Ser. No. 132,073 filed on Dec. 11, 1987 currently abandoned which in turn is a continuation-in-part of Ser. No. 020,849 filed on Mar. 2, 1987, abandoned, which in turn is a continuation-in-part application of Ser. No. 948,364 filed on Dec. 31, 1986 the latter two applications currently abandoned in favor of copending applications Ser. Nos. 07/436,092, now U.S. Pat. No. 5,110,908, now U.S. Pat. No. 5,108,744 both filed on Nov. 11, 1989.

TABLE OF CONTENTS

1. Field of the Invention
2. Background of the Invention
   2.1. Recombinant DNA Technology and Gene Expression
      2.1.1. *E. coli* as A Host System for Expression
      2.1.2. Vaccinia Virus as an Expression Vector
      2.1.3. Baculovirus as an Expression Vector
   2.2. *Haemophilus influenzae* and Disease
   2.3. Vaccines Against *H. influenzae*
3. Summary of the Invention
4. Brief Description of the Figures
5. Detailed Description of the Invention
   5.1. Isolation and Purification of PBOMP-1
      5.1.1. Isolation of PBOMP-1 Enriches Insoluble Cell Wall Material From *H. influenzae*
      5.1.2. Solubilization of PBOMP-1 From the PBOMP-1 Enriches Insoluble Cell Wall Material
   5.2 Characterization of PBOMP-1 by Amino Acid Analysis and Sequencing of PBOMP Peptides
   5.3. Generation of PBOMP-1 and/or PBOMP-2 Related Peptides
   5.4. Molecular Cloning of Genes or Gene Fragments Encoding PBOMP-1 and PBOMP-2
      5.4.1. Isolation of Genes Encoding PBOMP-1 and Related PBOMPs
      5.4.2. Insertion of PBOMP Genes Into Expression Vectors
      5.4.3. Identification and Purification of the Expressed Gene Products
   5.5. Nucleotide Sequencing of PBOMP Genes
   5.6. Determination of Immunopotency of PBOMPs
   5.7. Formulation of a Vaccine
      5.7.1. Subunit Vaccine Formulations
      5.7.2. Viral Vaccine Formulations
      5.7.3. Passive Immunity and Anti-Idiotypic Antibodies
   5.8. Diagnostic Assays
      5.8.1. Immunoassays
      5.8.2. Nucleic Acid Hybridization Assays
6. Examples: Isolation and Characterization of Natural and Recombinant DNA-Derived PBOMPs
   6.1. Isolation, Purification and Analysis of PBOMP-1
      6.1.1. Characterization of PBOMP-1 by Amino Acid Composition and Sequence
      6.1.2. Characterization of PBOMP-1 By Fatty Acid Analysis
   6.2. Preparation of Anti-PBOMP-1 and Anti-PBOMP-2 Antibodies
      6.2.1. Preparation of Polyclonal Anti-PBOMP-1 and Anti-PBOMP-2 Antiserum.
      6.2.2. Production of Anti-PBOMP-1 and Anti-PBOMP-2 Monoclonal Antibodies
   6.3. Reactivity of Anti-PBOMP-1 and Anti-PBOMP-2 Antibodies with *E. coli*
   6.4. General Procedures Used for Preparation of Recombinant Plasmids
      6.4.1. Conditions for Restriction Enzyme Digestions
      6.4.2. Gel Purification of DNA Fragments
      6.4.3. DNA Ligation
      6.4.4. Protein Immuno Blot Analysis (Western Blot)
      6.4.5. Gene Fusions
      6.4.6. DNA Filter Hybridization Analysis (Southern Blot)
   6.5. Cloning the PBOMP Genes of *H. influenzae*
      6.5.1. Construction of Hi Plasmid Library
      6.5.2. Construction of Hib Lambda Gene Bank
   6.6 Isolation of PBOMP Genes
      6.6.1. Isolation of a PBOMP Gene Encoding a Protein Which Reacts with Monoclonal Antibodies Against PBOMP-1
      6.6.2. Isolation of a PBOMP Gene Encoding a Protein Which Reacts with Polyclonal Anti-PBOMP-1 Antisera
   6.7. Determination of the Sequence of PBOMP Genes
      6.7.1. Sequencing Strategy for the PBOMP Gene Expressed by pAA152
      6.7.2. Sequencing Strategy for the PBOMPB Gene Expressed by pAA130
   6.8. Characterization of PBOMPs Expressed By Recombinant *E. coli* As Lipoproteins
7. Efficacy of PBOMP-1 and PBOMP-2 Subunit Vaccines
   7.1. Bactericidal Activity of Anti-Sera Induced by PBOMP-1 and PBOMP-2
   7.2. Infant Rat Protection from *H. influenzae*
   7.3. Immunogenicity of PBOMP-1 in Human Adults
   7.4. Bactericidal Activity of Anti-Sera Induced by rPBOMP-1
8. Novel Plasmids for Enhanced Expression of PBOMPs in *E. coli*
   8.1. Enhanced Expression of PBOMP-1 in *E. coli*
      8.1.1. Purification and Characterization of Signal-Less PBOMP-1
   8.2. Enhanced Expression of PBOMP-2 in *E. coli*
9. Mapping of Epitope Determinants of PBOMP-1
   9.1. Synthetic and Cleavage Peptides
   9.2. Monoclonal Antibodies (Mabs)
   9.3. Epitope Mapping With mabs
      9.3.1. Reactivity of Synthetic Peptides Via Direct ELISA Assays
      9.3.2. Inhibitory Activity of Synthetic Peptides
      9.3.3. Reactivity of Mabs with Proteolitically Cleaved PBOMP-1 Fragments
   9.4. Functional Activity of Mabs
10. Induction of a Biologically Functional Antibody by a Conjugate of a Synthetic N-Terminal Peptide of PBOMP-1
    10.1. Chemical Characterization of Peptide-Protein Conjugates 10.2. Preparation ;of Polyclonal Anti-PBOMP-1 N-Terminal (N-1-20) Peptide Antiserum
10.3. Preparation of Monoclonal Antibodies to PBOMP-1 N-Terminal (N-1-20) Peptide
10.4. Immunogenicity of PBOMP-1 N-Terminal (N-1-20) Peptide-Carrier Conjugate
10.5. Functional Assays: Bactericidal Activity of Anti-(N-1-20) Peptide Antibodies
11. Isolation and Characterization of the Recombinant-DNA Derived PBOMP-2: PBOMP-1 Fusion Protein
 11.1. Construction of the plasmid, pPX183, for the Expression of PBOMP-2: PBOMP-1 in *E. Coli*
 11.2. Expression of the PBOMP-2: PBOMP-1 Fusion Protein
 11.3. Construction of Plasmic pPX199 Expressing PBOMP-2: PBOMP-1 Fusion Protein
 11.4. Expression of Signal-Less PBOMP-2: PBOMP-1 Fusion Protein
12. Efficacy of Fusion Protein Subunit Vaccines
 12.1. Preparation of Anti-PBOMP-2: PBOMP-1 Antibodies
 12.2. PBOMP-2: PBOMP-1 Fusion Protein in Combination with E. Protein Induces Anti-Haemophilis Antibodies
13. Deposit of Microorganisms

1. FIELD OF THE INVENTION

The present invention relates to compositions and methods for the preparation of proteins and peptides associated with the outer membrane of *Haemophilus influenzae*. More particularly, the invention is directed to compositions and methods for preparation of proteins and peptides related to a class of outer membrane proteins of about 16000 daltons molecular weight of type b and non-typable *H. influenzae* including PBOMP-1 and PBOMP-2. The proteins and peptides are used as immunogens in vaccine formulations for active immunization and for the generation of antibodies for use in passive immunization and as reagents in diagnostic assays.

The proteins and peptides can be obtained by novel improved methods of purification from *H. influenzae* or produced using either recombinant DNA or chemical synthetic methods. Additionally, the invention relates to novel DNA sequences and vectors useful for directing expression of PBOMP-1 and PBOMP-2 related proteins and peptides. The nucleotide sequences are used as reagents in nucleic acid hybridization assays.

2. BACKGROUND OF THE INVENTION

2.1 Recombinant DNA Technology and Gene Expression

Recombinant DNA technology involves insertion of specific DNA sequences into a DNA vehicle (vector) to form a recombinant DNA molecule which is capable of replication in a host cell. Generally, the inserted DNA sequence is foreign to the recipient DNA vehicle, i.e., the inserted DNA sequence and the DNA vector are derived from organisms which do not exchange genetic information in nature, or the inserted DNA sequence may be wholly or partially synthetically made. Several general methods have been developed which enable construction of recombinant DNA molecules. For example, U.S. Pat. No. 4,237,224 to Cohen and Boyer describes production of such recombinant plasmids using processes of cleavage with restriction enzymes and joining with DNA ligase by known methods of ligation. These recombinant plasmids are then introduced by means of transformation and replicated in unicellular cultures including procaryotic organisms and eucaryotic cells grown in tissue culture. Because of the general applicability of the techniques described therein, U.S. Pat. No. 4,237,224 is hereby incorporated by reference into the present specification.

Another method for introducing recombinant DNA molecules into unicellular organisms is described by Collins and Hohn in U.S. Pat. No. 4,304,863 which is also incorporated herein by reference. This method utilizes a packaging/transduction system with bacteriophage vectors (cosmids).

Recombinant genes may also be introduced into viruses, such as vaccina virus. Recombinant viruses can be generated by transfection of plasmids into cells infected with virus.

Regardless of the method used for construction, the recombinant DNA molecule must be compatible with the host cell, i.e., capable of autonomous replication in the host cell or stably integrated into one of the host cell's chromosomes. The recombinant DNA molecule or virus (e.g., a vaccinia virus recombinant) should also have a marker function which allows the selection of the desired recombinant DNA molecule(s) or virus(es). In addition, if all of the proper replication, transcription and translation signals are correctly arranged on the recombinant DNA molecule, the foreign gene will be properly expressed in the transformed bacterial cells, as is the case with bacterial expression plasmids, or in permissive cell lines infected with a recombinant virus or a recombinant plasmid carrying a eucaryotic origin of replication.

Different genetic signals and processing events control many levels of gene expression; for instance, DNA transcription and messenger RNA (mRNA) translation. Transcription of DNA is dependent upon the presence of a promotor which is a DNA sequence that directs the binding of RNA polymerase and thereby promotes mRNA synthesis. The DNA sequences of eucaryotic promotors differ from those of procaryotic promotors. Furthermore, eucaryotic promotors and accompanying genetic signals may not be recognized in or may not function in a procaryotic system and further, procaryotic promotors are not recognized and do not function in eucaryotic cells.

Similarly, translation of mRNA in procaryotes depends upon the presence of the proper procaryotic signals which differ from those of eucaryotes. Efficient translation of mRNA in procaryotes requires a ribosome binding site called the Shine-Dalgarno (SD) sequence on the mRNA. This sequence is a short nucleotide sequence of mRNA that is located before the start codon, usually AUG, which encodes the amino-terminal methionine of the protein. The SD sequences are complementary to the 3'-end of the 16S rRNA (ribosomal RNA) and probably promote binding of mRNA to ribosomes by duplexing with the rRNA to allow correct positioning of the ribosome. For a review on maximizing gene expression, see Roberts and Lauer, 1979, Methods in Enzymology 68:473.

Many other factors complicate the expression of foreign genes in procaryotes even after the proper signals are inserted and appropriately positioned. One such factor is the presence of an active proteolytic system in *E. coli* and other bacteria. This protein-degrading system appears to selectively destroy "abnormal" or foreign proteins A tremendous utility, therefore, would be afforded by the development of a means to protect eucaryotic proteins expressed in bacteria from proteolytic degradation. One strategy is to construct hybrid genes in which the foreign sequence is ligated in phase (i.e., in the correct reading frame) with a procaryotic gene. Expression of this hybrid gene results in a fusion protein product (a protein that is a hybrid of procaryotic and foreign amino acid sequences).

Successful expression of a cloned gene requires efficient transcription of DNA, translation of the mRNA and in some instances post-translational modification of the protein. Expression vectors have been used to express genes in a suitable host and to increase protein production. The cloned gene should be placed next to a strong promotor which is controllable so that transcription can be turned on when necessary. Cells can be grown to a high density and then the promotor can be induced to increase the number of transcripts. These, if efficiently translated will result in high yields of protein. This is an especially valuable system if the foreign protein is deleterious to the host cell.

2.1.1 E. coli as a Host System for Expression

Most plasmid cloning vectors commonly used in E. coli are derivatives of ColE1-type replicons (for additional information see Oka et al., 1979, Mol. Gen. Genet. 172:151-159). The ColE1 plasmids are stably maintained in E. coli strains as monomeric molecules with a copy number of about 15-20 copies per chromosome. Various levels of expression of human and animal protein products of foreign genes inserted into these plasmids have been obtained. However, very high expression levels should be obtained in order for the system to become economically feasible to produce foreign protein products.

One way to obtain large amounts of a given gene product is to clone a gene on a plasmid which has a very high copy number within the bacterial cell. In theory, by increasing the number of copies of a particular gene, mRNA levels should also increase which should lead to increased production of the recombinant protein.

2.1.2. Vaccinia Virus as an Expression Vector

Vaccinia virus may be used as a cloning and expression vector. The virus contains a linear double-stranded DNA genome of approximately 187 kb pairs which replicates within the cytoplasm of infected cells. These viruses contain a complete transcriptional enzyme system (including capping, methylating and polyadenylating enzymes) within the virus core which are necessary for virus infectivity. Vaccinia virus transcriptional regulatory sequences (promotors) allow for initiation of transcription by vaccinia RNA polymerase but not by eucaryotic RNA polymerase.

Expression of foreign DNA in recombinant viruses requires the fusion of vaccinia promotors to protein coding sequences of the foreign gene. Plasmid vectors, also called insertion vectors have been constructed to insert the chimeric gene into vaccina virus. One type of insertion vector is composed of: (1) a vaccinia virus promotor including the transcriptional initiation site; (2) several unique restriction endonuclease cloning sites downstream from the transcriptional start site for insertion of foreign DNA fragments; (3) nonessential vaccinia virus DNA (such as the TK gene) flanking the promotor and cloning sites which direct insertion of the chimeric gene into the homologous nonessential region of the virus genome; and (4) a bacterial origin of replication and antibiotic resistance marker for replication and selection in E. coli. Examples of such vectors are described by MacKett (1984, J. Virol. 49: 857-864)

Recombinant viruses are produced by transfection of recombinant bacterial insertion plasmids containing the foreign gene into cells infected with vaccinia virus. Homologous recombination takes place within the infected cells and results in the insertion of the foreign gene into the viral genome. Recombinant viruses can be screened for and subsequently isolated using immunological techniques, DNA plaque hybridization, or genetic selection. These vaccinia recombinants retain their essential functions and infectivity and can be constructed to accommodate approximately 35 kb of foreign DNA.

Expression of a foreign gene can be detected by enzymatic or immunological assays [e.g., immunoprecipitation, enzyme-linked immunosorbent assay (ELISA), radioimmunoassay, or immunoblotting]. Additionally, naturally occurring membrane glycoproteins produced from recombinant vaccinia infected cells are glycosylated and may be transported to the cell surface. High expression levels can be obtained by using strong promotors or cloning multiple copies of a single gene in appropriate vectors and suitable hosts.

2.1.3. Baculovirus as an Expression Vector

A baculovirus, such as *Autographica californica* nuclear polyhedrosis virus (AcNPV) may also be used as a cloning or expression vector. The infectious form of AcNPV is normally found in a viral occlusion. This structure is largely composed of polyhedrin peptide in which virus particles are embedded. Polyhedrin gene expression occurs very late in the infection cycle, after mature virus particles are formed. Therefore polyhedrin gene expression is a dispensible function, i.e., nonoccluded virus particles produced in the absence of polyhedrin gene expression are fully active and are capable of infecting cells in culture. According to European Patent Application Serial No. 84105841.5 by Smith et al., a recombinant baculovirus expression vector is prepared by cleaving baculovirus DNA to produce a fragment comprising a polyhedrin gene or portion thereof, inserting this fragment into a cloning vehicle and thereafter inserting the gene to be expressed such that it is under control of the polyhedrin gene promotor. The recombinant transfer vector formed in this way is mixed with baculovirus helper DNA and used to transfect insect cells in culture to effect recombination and incorporation of the selected gene at the polyhedrin gene locus of the baculovirus genome. The resultant recombinant baculovirus is used to infect susceptible insects or cultured insect cells.

2.2 Haemophilus influenzae and Disease

*H. influenzae* are divided into two groups. Those strains which possess a known capsule are typed by the serological reaction of the capsule with reference antisera. Types a-f have been identified. Strains which fail to react with any of the reference antisera are known as non-typable.

*H. influenzae* type b (Hib) is the most frequent cause of neonatal meningitis and other invasive infections in the Unites States (Fraser et al., 1974, Am. J. Epidemiol. 100:29-34). The major incidence of childhood meningitis occurs between the ages of one and five years. Sixty percent of those meningitis cases due to Hib occur in children under the age of two (Fraser et al., supra).

It is now well established that non-typable *H. influenzae* (Hi) also cause diseases including pneumonia, bacteremia, meningitis, postpartum sepsis, and acute febrile tracheobronchitis in adults (Murphy et al., 1985, J. Infect. Diseases 152: 1300–1307). Non-typable Hi are a frequent etiologic agent of otitis media in children and young adults, causing about 20 to 40% of all otitis media cases. Children may experience multiple infections due to the same organism since infection confers no long lasting immunity. Current therapy for chronic or repeated occurrences of otitis media includes administration of antibiotics and insertion of tubes to drain the inner ear. Hi strains have also been implicated as a primary cause of sinusitis (Cherry J. D. and J. P. Dudley, 1981, in Textbook of Pediatric Infectious Diseases, Feigin and Cherry eds., pp 103–105). Additionally, non-typable Hi cause neonatal sepsis.

Antiserum produced against the capsular polysaccharide of type b *H. influenzae* (Hib) which comprises polyribosyl ribitol phosphate (PRP), has been shown to be bactericidal and protective against Hib (Smith et al., 1973, Pediatrics 52:637–644; Anderson, et al., 1972, J. Clin. Inv. 51:31–38). Anti-PRP antibody is ineffective against non-typable *H. influenzae* infections.

2.3 Vaccines Against H. influenzae

The ideal candidate for a Haemophilus vaccine would have three properties: a) it would be immunogenic in infants of 2–6 months (b) it would elicit an antibody which would protect against infections caused by typable and non-typable *H. influenzae*, and (c) it would elicit antibody against a determinant found on the surface of all strains of *H. influenzae*.

The currently available vaccines which protect against Hib infections consist essentially of PRP, the type b capsular polysaccharide. Purified PRP polysaccharide is immunogenic in children above 18 months of age, but does not elicit a protective antibody response in those younger than 18 months. In general, polysaccharides have been shown to be poor immunogens in children less than about 18 months of age.

To address this problem, various laboratories have begun studies in which PRP is either chemically coupled to a protein carrier molecule (Anderson et al., 1985, ped. Res. 18:252A) or mixed with protein molecules (Monji et al., 1986, Infect. Immun. 51:865–871) and administered to animals or humans. Conjugation of PRP to protein has been shown to elicit an anti-PRP antibody response in human infants as young as 6 months, while a mixture of PRP with some proteins has produced anti-PRP antibody in infant animals (Monji et al., supra).

Although the conjugate and admixture vaccine formulations address one difficulty of PRP vaccines, i.e., their inability to protect infants younger than 18 months, they fail to address another major problem of the PRP vaccine. Anti-PRP antibody is ineffective against non-typable *H. influenzae*, which by definition lack the PRP capsule. Hence there is a long recognized need for a vaccine that will elicit a protective immune response in children of about 18 months and younger against both typable, including type b and non-typable *H. influenzae*.

One object of the present invention is to provide a vaccine formulation that elicits a protective immune response against typable *H. influenzae* including type b and non-typable *H. influenzae* in children under 6 months as well as in older children and adults. The approach of the present invention is to vaccinate with a protein or fragment thereof which is exposed on the surface of Haemophilus. The best candidate is an outer membrane protein (OMP) of *H. influenzae*. Outer membrane proteins are usually surface exposed molecules. They are composed of protein which is normally immunogenic in infants, and they have been shown to be capable of eliciting protective antibody in other bacterial systems (Sugasawara et. al., 1983, Infect. Immun. 42:980–985).

In addition Hi and Hib strains have been shown to have similar OMP profiles (Loeb and Smith, 1980, Infect. Immun. 30:709–717). Antibody to an OMP of Haemophilus could be both bactericidal and opsonic much as anti-PRP has been shown to be bactericidal and opsonic for Hib (Anderson et al., 1972, J. Clin. Invest. 51:31–38; Cates et al., 1985, Infect. Immun. 48:183–189). An outer membrane protein has the additional advantage of being common to Hi and Hib and could protect against both types of bacteria.

3 SUMMARY OF THE INVENTION

The present invention is directed to peptides and proteins related to an outer membrane protein of about 16,000 daltons molecular weight of Haemophilus influenzae identified by applicants and termed "Praxis Biologics Outer Membrane Protein-1" (PBOMP-1) and to an antigenically related outer membrane protein of about 16,000 daltons molecular weight of *Haemophilus influenzae* also identified by applicants and termed "Praxis Biologics Outer Membrane Protein-2" (PBOMP-2), as well as the molecularly cloned genes or gene fragments which encode these peptides or proteins. The present invention is also directed to peptides and proteins related to a PBOMP-1: PBOMP-2 or PBOMP-2: PBOMP-1 fusion protein as well as the molecularly cloned genes or gene fragments which encode these peptides or proteins. In a specific embodiment of the invention, chemically synthesized PBOMP-1 or PBMOP-2 related peptides encompass an antigenic region(s) of PBOMP-1 or PBOMP-2 respectively. The peptides are conjugated to a protein carrier, resulting in the generation of an immunogenic peptide conjugate. The invention is also directed to a substantially pure PBOMP-1 obtained from *H. influenzae* using novel and improved methods. The peptides or proteins of the present invention may be used as immunogens in vaccine formulations for *H. influenzae*, or as reagents in diagnostic immunoassays for *H. influenzae*.

The present invention is also directed to methods for the molecular cloning of genes or gene fragments encoding PBOMP-1 and PBOMP-2 related peptides. These molecularly cloned sequences can then be used in the further construction of other vectors by recombinant DNA techniques, including expression vectors for the encoded peptide products, or use in diagnostic assays for *H. influenzae* based on nucleic acid hybridization, or in construction of a sequence encoding a PBOMP-1: PBOMP-2 or PBOMP-2: PBOMP-1 fusion protein.

The peptides or proteins of the present invention may be purified from *H. influenzae*, or produced using recombinant DNA techniques in any vector-host system, or synthesized by chemical methods. Accordingly, the invention is also directed to the construction of novel DNA sequences and vectors including plasmid DNA, and viral DNA such as human viruses, animal viruses, insect viruses, or bacteriophages which can be used to direct the expression of PBOMP-1 and PBOMP-2 related peptides or proteins as well as PBOMP-1: PBOMP-2 or PBOMP-2: PBOMP-1 related peptides or proteins in appropriate host cells from which the peptides and proteins may be purified. Chemical methods for the synthesis of PBOMP-1 and PBOMP-2 related peptides and proteins are described.

PBOMP-1, PBOMP-2, PBOMP-1: PBOMP-2 and PBOMP-2: PBOMP-1 related peptides and proteins can be used as immunogens in subunit vaccine formulations for use against all pathogenic *H. influenzae*, including both type b and non-typable *H influenzae*. PBOMP-1 and PBOMP-2 related proteins or peptides for subunit vaccine preparations can be obtained by chemical synthesis, purification from *H. influenzae* or purification from recombinant expression vector systems. PBOMP-1: PBOMP-2 and PBOMP-2 PBOMP-1 related proteins or peptides for subunit vaccine preparations can be obtained by purification from recombinant expression vector systems or by chemical synthesis. Alternatively, recombinant viruses which produce the PBOMP-1, PBOMP-2, PBOMP-1: PBOMP-2, or PBOMP-2: PBOMP-1 related peptides or proteins themselves or extracts of cells infected with such recombinant viruses can be used as immunogens in viral vaccine formulations. Since the PBOMP-1 or PBOMP-2 protein or PBOMP-1: PBOMP-2 or PBOMP-2: PBOMP-1 fusion protein will be recognized as "foreign" in the host animal, a humoral and possibly a cell-mediated immune response will be induced, directed against PBOMP-1, PBOMP-2, PBOMP-1: PBOMP-2 or PBOMP-2: PBOMP-1 respectively. In a properly prepared vaccine formulation, this should protect the host against subsequent *H. influenzae* infections. Moreover, the present subunit vaccine formulations will be compatible with currently available PRP vaccines.

The PBOMP-1-related and/or PBOMP-2 related sequences of the present invention can be used in human medical assays. These include the use of the peptides and proteins of the present invention as reagents in immunoassays such as ELISA tests and radioimmunoassays which are useful as diagnostic tools for the detection of *H. influenzae* infection in blood samples, body fluid, tissues, etc. The PBOMP-1 encoding and/or PBOMP-2-encoding gene sequences can be used in DNA-DNA or DNA-RNA hybridization assays for similar diagnostic detection of *H. influenzae*. Additionally, these reagents will provide a valuable tool in elucidating the mechanism of pathogenesis of *H. influenzae*.

The present invention is directed further to anti-PBOMP-1, anti-PBOMP-2, anti-PBOMP-1: PBOMP-2, and/or anti-PBOMP-2: PBOMP-1 monoclonal antibodies which have uses in passive immunization regimes, and in diagnostic immunoassays. In one embodiment of the invention, monoclonal antibodies may be generated against PBOMP-1, PBOMP-2, PBOMP-1: PBOMP-2, and/or PBOMP-2: PBOMP-1 related peptides.

4 BRIEF DESCRIPTION OF THE FIGURES

The present invention may be more fully understood by reference to the following detailed description and examples of specific embodiments as well as the appended figures in which:

FIG. 1 represents sodium dodecylsulfate polyacrylamide gel electrophoretic (SDS-PAGE) analysis of PBOMP-1. Samples and gels were prepared as described in Section 6.1. Lane A contains about 5 ug PBOMP-1. Lane B contains prestained low molecular weight (MW) standards: ovalbumin, alpha-chymotrypsinogen, beta-lactoglobulin, lysozyme, bovine trypsin inhibitor and insulin (A and B chains). Relative MWs [in kilodaltons (kd)] are shown at the side.

FIG. 2 (A and B) represents reactivity of whole cell lysates of *E. coli* and *H. influenzae* with polyclonal anti-PBOMP-1 antibody and a monoclonal anti-PBOMP-1 antibody (G1-1). In FIG. 2A, lysates were reacted with polyclonal anti-PBOMP-1 antibody. Lanes are as follows: (1) *E. coli* HB101; (2) *E. coli* JM83; (3) molecular weight standards; (4) purified PBOMP-1 obtained from cultured *H. influenzae* cells. In FIG. 2B, lysates were reacted with monoclonal anti-PBOMP-1 antibody. Lanes are as described in FIG. 2A.

FIG. 3 represents a restriction map of pGD103, a derivative of pLG339 (see Stoker et al., 1982, Gene 18:335–41).

FIG. 4 (A and B) represents maps of pAA152 which comprises a 4.2 Kb fragment of *H. influenzae* DNA cloned into pGD103. A gene encoding PBOMP-1 is localized to an 737 bp BglII-BamHI fragment. FIG. 4A is a circular restriction map of pAA152. FIG. 4B illustrates deletion analysis of the inserted fragment of pAA152. The remaining *H. influenzae* DNA in the deletion derivatives is denoted by black lines. PBOMP phenotype is noted at the right.

FIG. 5 represents reactivity of whole cell lysates of *E. coli* JM83 containing pAA152 with individual monoclonal antibodies which react with different epitopes of PBOMP-1. Lanes are as follows: (A) monoclonal antibody G1-1; (b) monoclonal antibody G94-3; (C) monoclonal antibody G18-3; (D) monoclonal antibody 25-2; and (E) monoclonal antibody G2-3.

FIG. 6 represents autoradiographic analysis of DS410 minicells containing recombinant plasmids pAA130 and pAA152. Molecular weight standards are noted at the left of the figure. Lanes represent: (A) DS410 (pAA130); (B) DS410 (pGD103); and (C) DS410 (pAA152). The location of kanamycin aminoglycosidase is noted t the right of the figure.

FIG. 7 (A and B) represents maps of pAA130 which comprises a 5.7 Kb fragment of *H. influenzae* DNA cloned into pGD103. FIG. 7A represents a circular restriction map of pAA130. FIG. 7B represents deletion analysis of the H. influenzae inserted fragment of pAA130. Solid black lines denote remaining *H. influenzae* DNA in the deletion derivatives. PBOMP phenotype is noted at the right. A gene encoding PBOMP-2 is localized to a 781 bp BstEII-XmnI fragment.

FIG. 10 represents the nucleotide sequence of the 737 bp fragment which contains the PBOMP-1 gene. The predicted open reading frame (ORF) is shown by the underlined sequence and the direction of transcription indicated by the arrowhead.

FIG. 11 represents the deduced amino acid sequence of PBOMP-1. The nucleotide sequence is depicted on the upper line and the corresponding amino acid sequence below. The amino acid enclosed within the box represents the predicted N-terminal amino acid of the mature form of the protein.

FIG. 12 represents alignment of the partial amino acid sequence of a peptide derived from PBOMP-1 (below) with a portion of the derived amino acid sequence of the PBOMP-1 gene (above). Residues enclosed within boxes represent mismatches.

FIG. 13 represents the sequencing strategy of the 789 bp BstEII-XmnI fragment of pAA130 showing the origin, direction and extent of sequence determined from each clone. The arrow at the bottom denotes the location of the major open reading frame (ORF).

FIG. 14 represents the nucleotide sequence of the 789 bp BstEII-XmnI fragment of pAA130 which contains the PBOMP-2 gene. The predicted ORF is shown by the underlined sequence. The direction of transcription is denoted by the arrowhead. The two bases designated "N" represent unknown nucleotides.

FIG. 15 represents the deduced amino acid sequence of PBOMP-2. The nucleotide sequence is depicted above and the corresponding amino acid sequence below. The residue enclosed within the box indicates the predicted N-terminal amino acid of the mature form of the protein.

Figure 16:
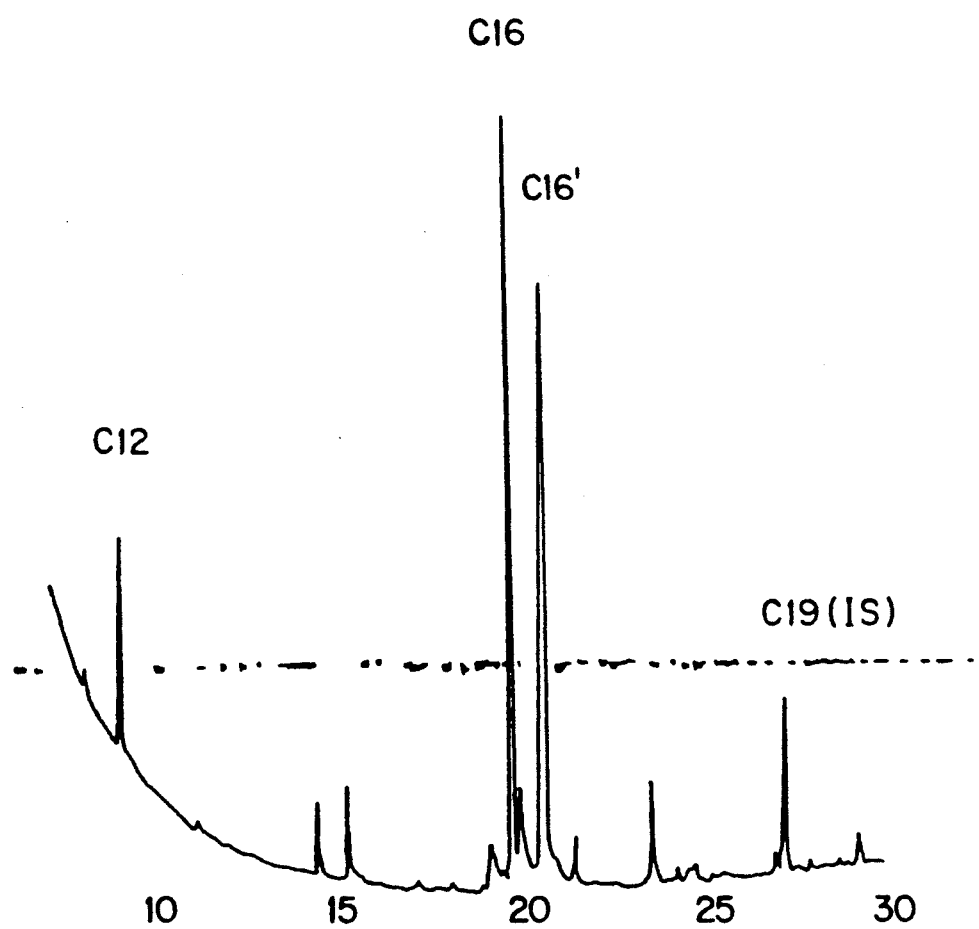

FIG. 16 represents a chromatogram, obtained using gas liquid chromatography, of the fatty acids of PBOMP-1. Nonadecanoic acid (C 19) was included as an internal standard.

FIG. 17 represents autoradiographic SDS-PAGE analysis of E. coli JM83 cells containing recombinant plasmids pAA130 and pAA152 as well as control E. coli JM83 cells containing pGD103. Lanes represent: (1) pAA130; (2) pAA152 and (3) pGD103. The location of a band of about 15,000 daltons molecular weight is noted at the left of the figure.

Figure 18B:
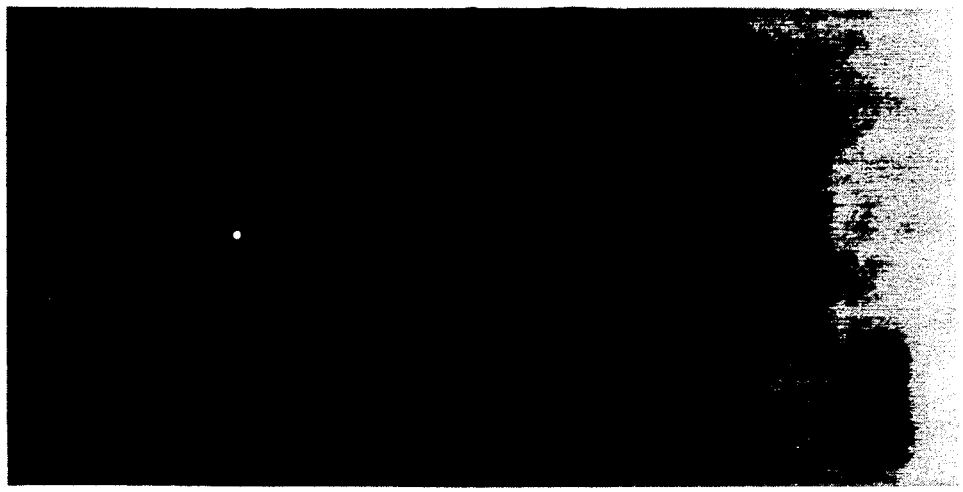
Figure 18A:

FIG. 18 (A and B) represents Western blot gel analysis of whole cell lysates of E. coli JM83 containing pAA130 or pAA152 in the presence or absence of globomycin. Molecular weight standards are noted at the left of FIG. 18 (A and B). FIG. 18A represents lysates of cells containing pAA152 which contains the PBOMP-1 gene. Lanes represent: (1) globomycin absent; and (2) globomycin present.

FIG. 18B represents lysates of cells containing pAA130 which contains the PBOMP-2 gene. Lanes represent: (1) globomycin absent; and (2) globomycin present.

FIG. 19 graphically illustrates the antibody response obtained when a vaccine formulation comprising PBOMP-1 (5.2 ug) was administered to human adults.

Figure 20:
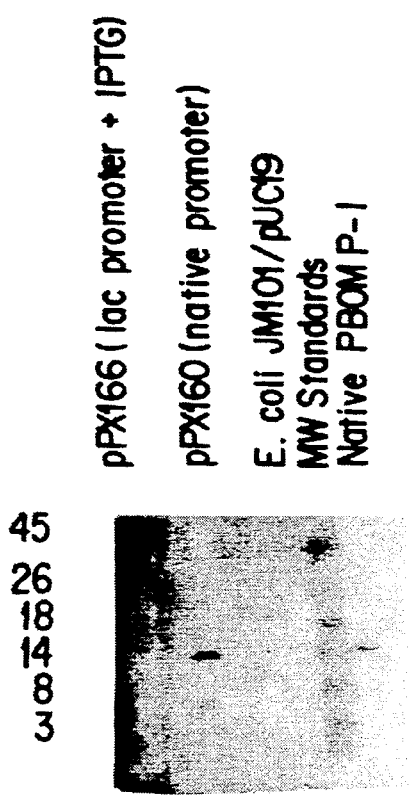

FIG. 20 represents reactivity of whole cell lysates of E. coli JM101 or JM103 with monoclonal antibody G-204. Lanes represent: (A) JM103 containing pPX166; (B) JM103 containing pPX160; (C) JM101 containgin pUC19; (D) molecular weight standard displayed in kilodaltons on the left side of the figure; and (E) native PBOMP-1 from H. influenzae.

Figure 21:
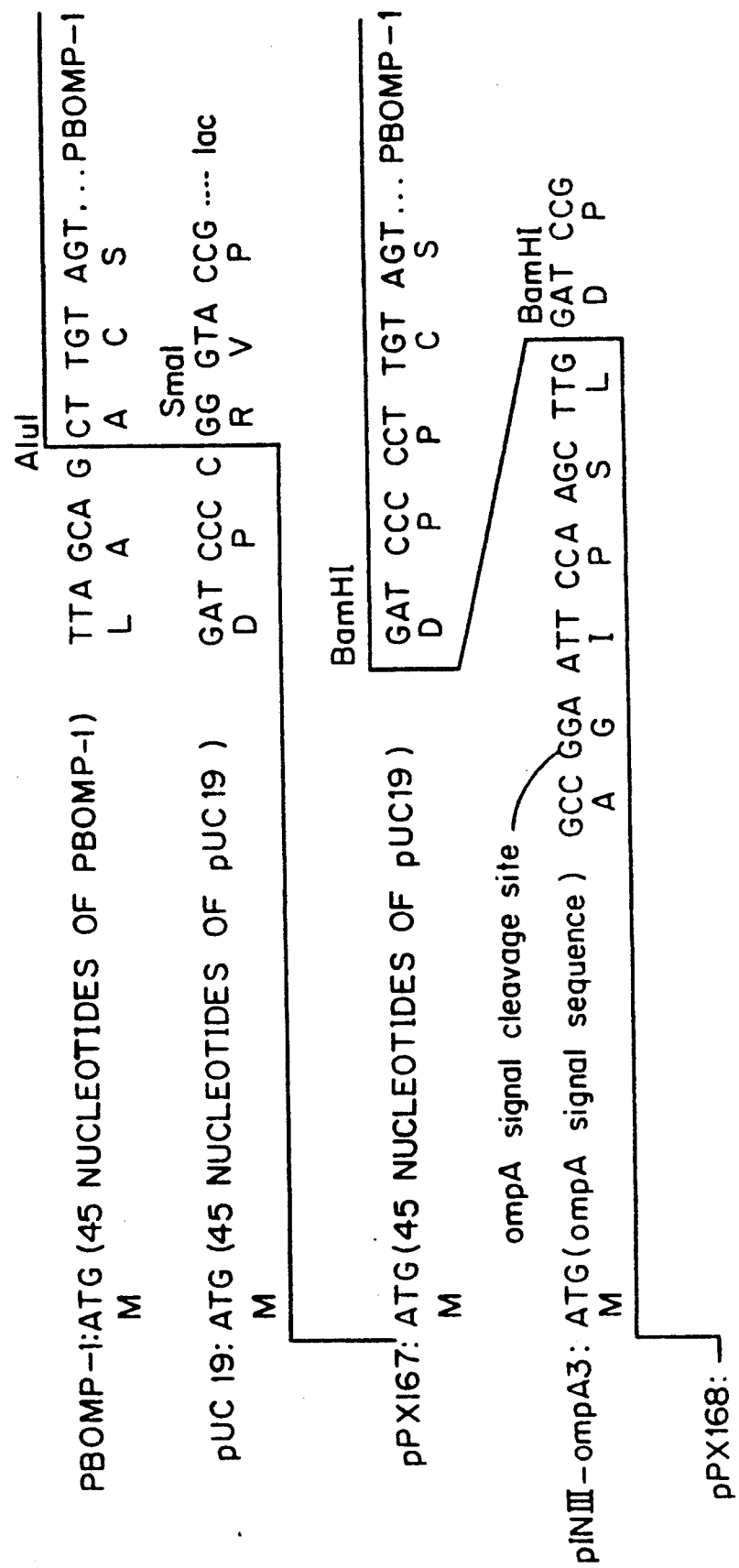

FIG. 21 is a schematic representation of the construction of plasmids containing the PBOMP-1 protein coding sequence lacking the PBOMP-1 signal sequence. In plasmid pPX167, the PBOMP-1 gene lacking the signal sequence is inserted downstream from the lac promoter. Plasmid pPX168 was constructed by cleaving the PBOMP-1 coding sequence in pPX167 at the BamHI site in the polylinker and cloning the resulting fragment into the BamHI site of plasmid pINIII-ompA3. Plasmid pPX168 contains a chimeric sequence coding for mature PBOMP-1 linked at the amino termius to the signal sequence of E. coli omp A protein.

FIG. 22 represents a chromatogram obtained using reverse phase C-4 high performance liquid chromatography of the supernatant fraction of a cytoplasmic extract of E. coli strain PR13 containing plasmid pPX167.

FIG. 23A represents SDS-PAGE analysis of signalless PBOMP-1 obtained from E. coli PR13 containing plasmid ppX167 stained with Coomassie stain. Lanes represent: (1) cytoplasmic fraction; (2) DEAE eluate; and (3) reverse phase eluate. Molecular weight standards were run in the lane to the left of lane 1 and relative MWs (in kilodaltons) are shown at the left side of the figure.

FIG. 23B represents reactivity of the fractions with anti-PBOMP-1 monoclonal antibody. Lanes are as in FIG. 23A.

Figure 24:
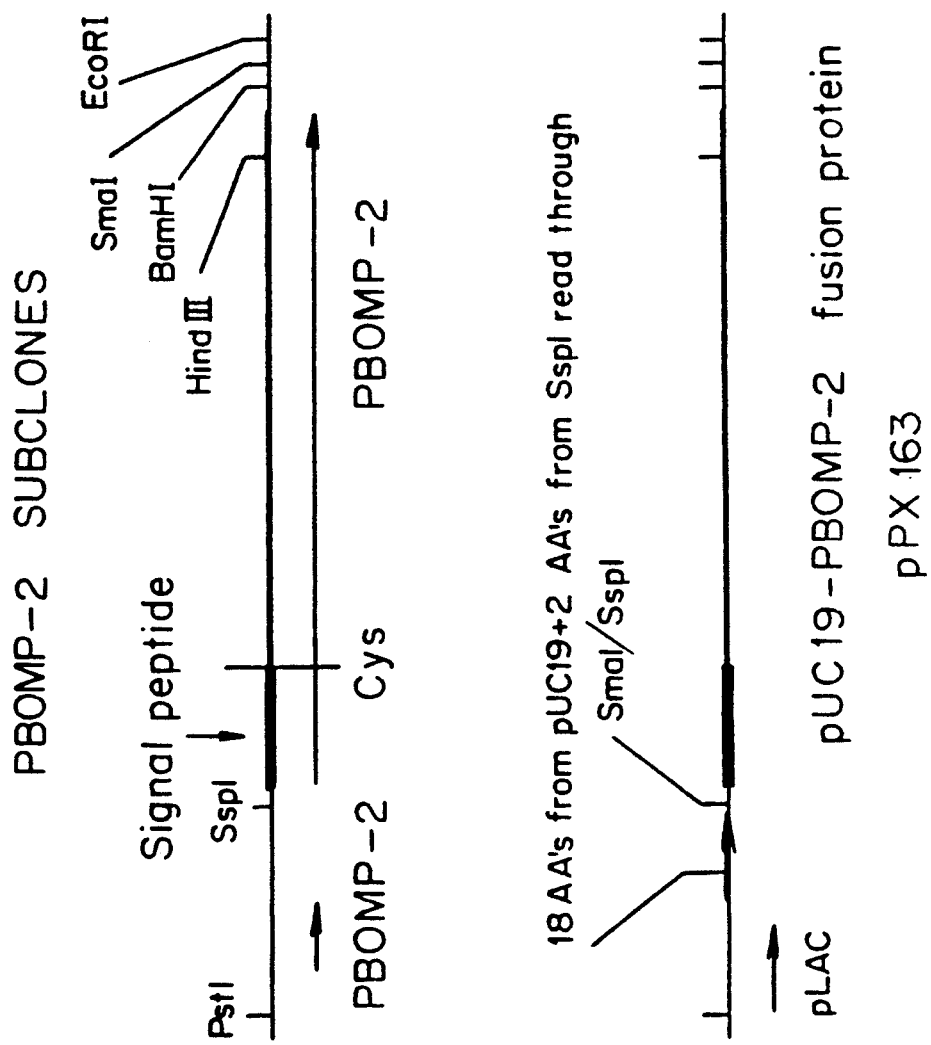

FIG. 24 is a schematic representation of the construction of plasmid pPX163 containing the entire coding sequence of PBOMP-2 protein inserted downstream from the lac promoter.

Figure 25:
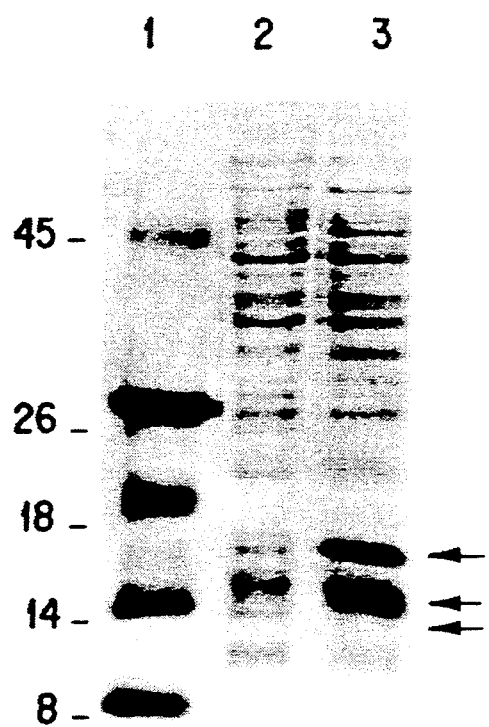

FIG. 25 represents an SDS-PAGE analysis of whole cell lysates of E. coli JM103 containing pPX163 grown in the presence or absence of IPTG. Lanes represent: (1) molecular weight standards: Kilodaltons; (2) lysate of JM103 containing pPX163 grown without IPTG; and (3) as in Lane 2, grown in the presence of IPTG (5mM) for 4 hours. Arrows show position of three PBOMP-2 reactive bands induced by IPTG.

Figure 26:
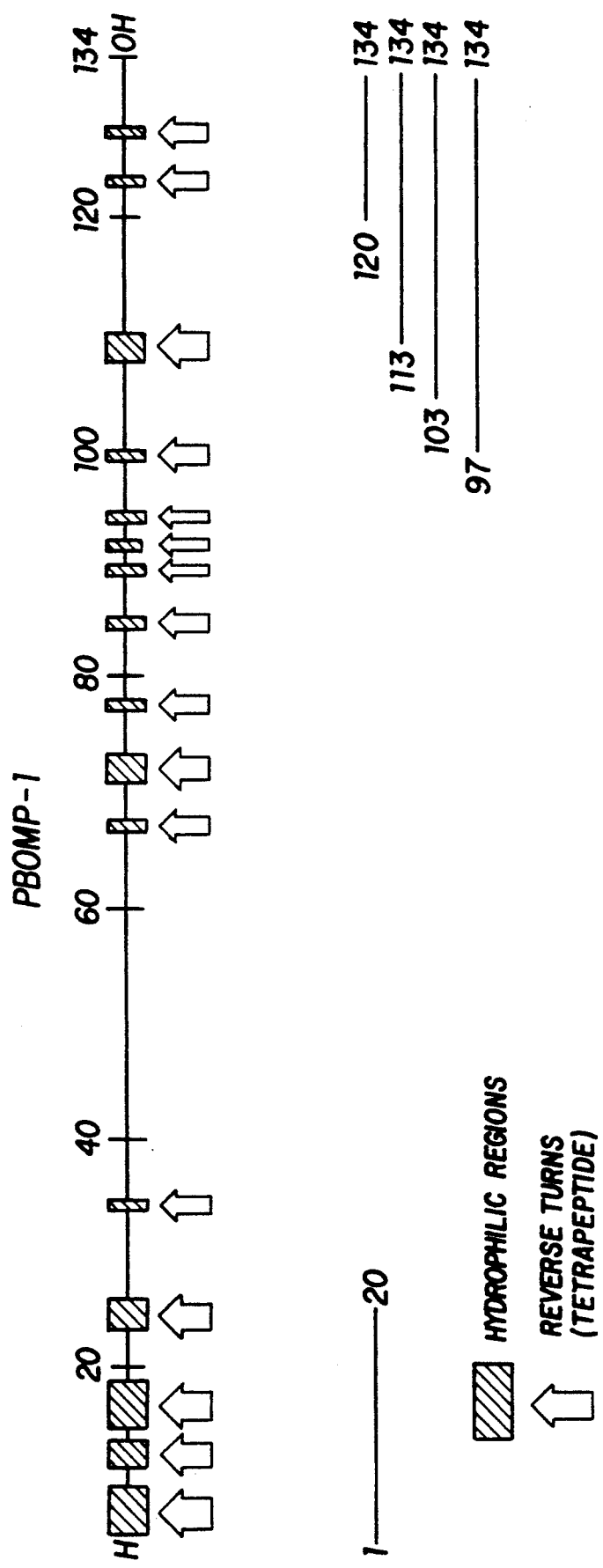

FIG. 26 is a schematic representation of the structure of PBOMP-1 represents hydrophilic regions of the protein and represents reverse turns present in the secondary structure of the protein. The location and size of chemically synthesized PBOMP-1 related peptides within the PBOMP-1 sequences are shown below.

FIG. 27 represents the amino acid sequences of the five chemically synthesized PBOMP-1 related peptides.

Figure 28:
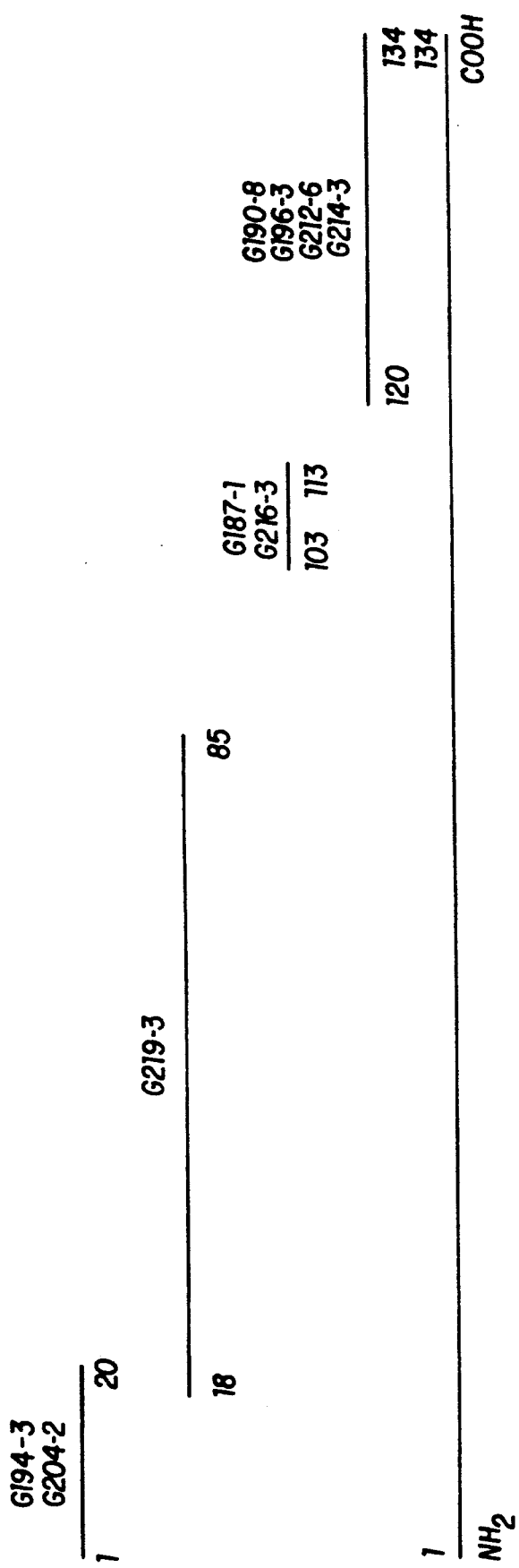

FIG. 28 shows a map of epitopes on the PBOMP-1 protein recognized by monoclonal antibodies to PBOMP-1.

Figure 29:
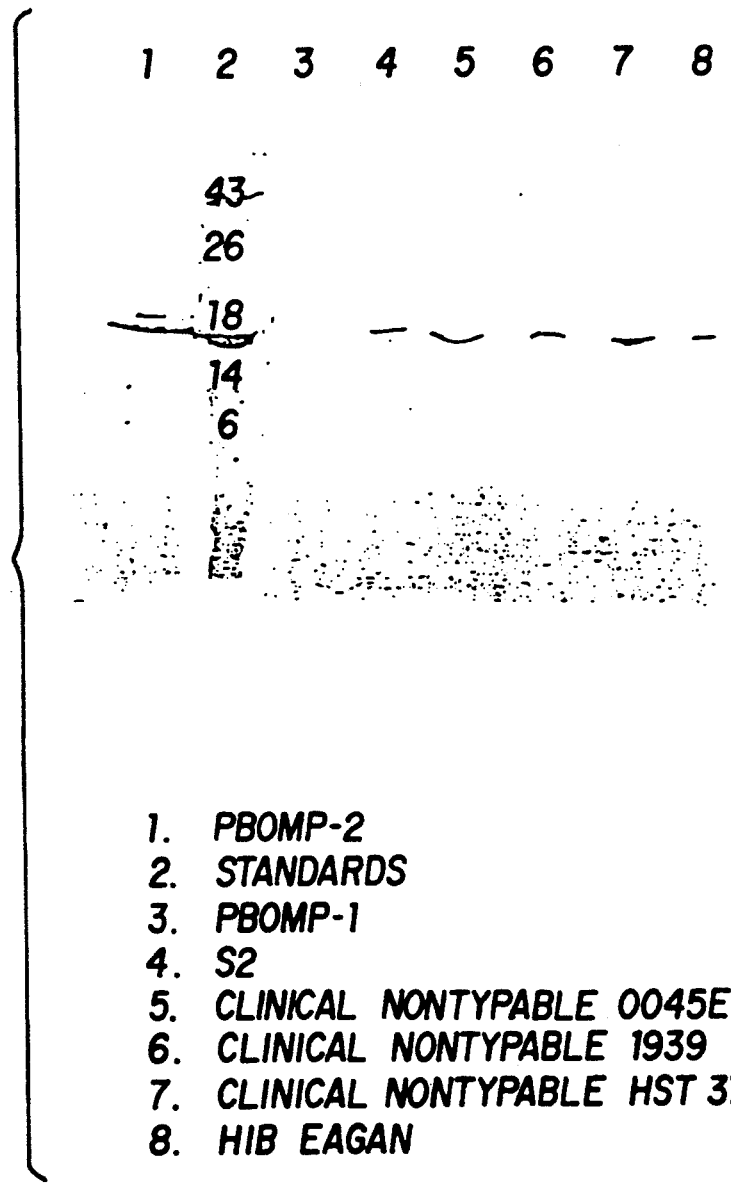

FIG. 29 represents reactivity of whole cell lysates of infected E. coli JM103 cells with the capsule deficient H. influenzae strain S2 (lane 4); or of the clinical nontypable H. influenzae strains: 0045E (lane 5), 1939 (lane 6), HST31 (lane 7), and Hib Eagan (lane 8) with anti-PBOMP-2 monoclonal antibody, 61-1. Molecular weight standards (kilodaltons) are shown in lane 2. The reactivities of PBOMP-2 and PBOMP-1 with anti-PBOMP-2 monoclonal antibody 61-1 are shown in lanes 1 and 3 respectively.

Figure 30:
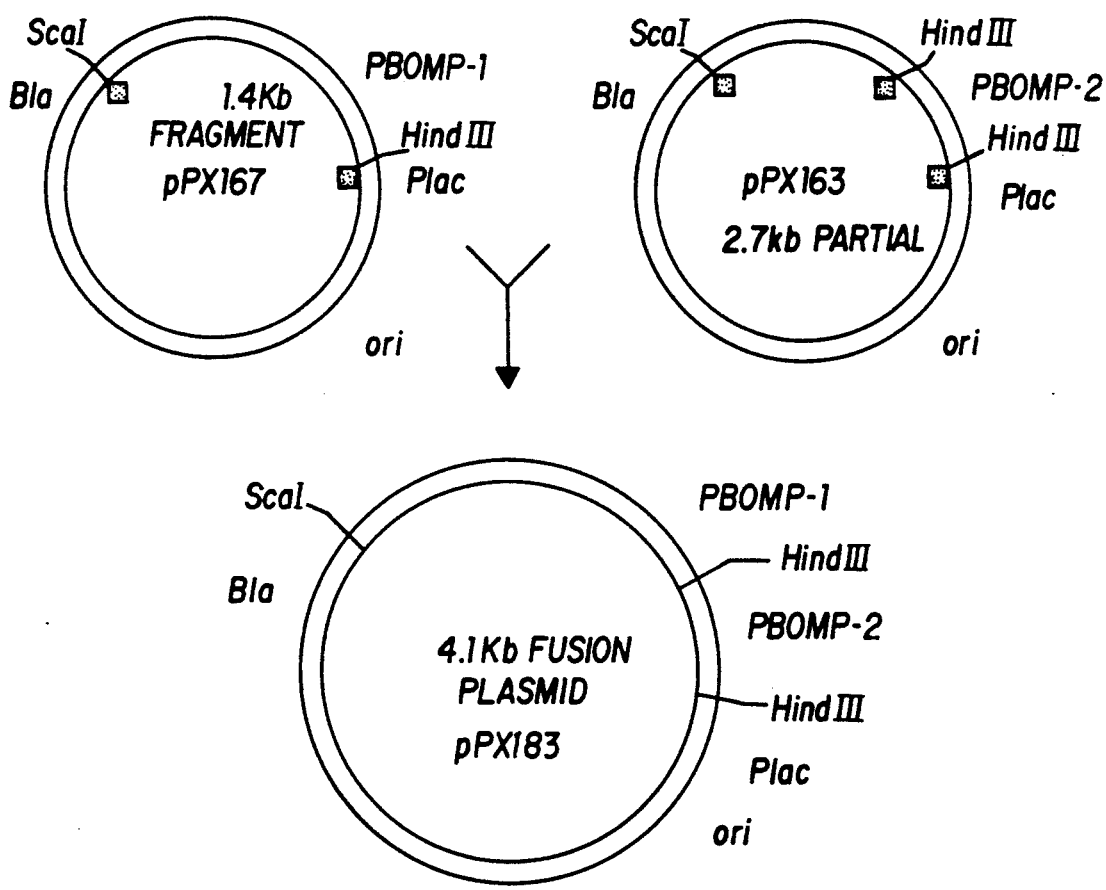

FIG. 30 is a schematic representation of the construction of a plasmid containing the PBOMP-2: PBOMP-1 fusion protein coding sequence. Plasmid pPX183 was constructed by separately digesting plasmids, pPX163 and pPX167 with ScaI to completion. The pPX163 ScaI digest was further treated with HindIII to yield a partial digest and the pPX167 ScaI digest was completely digested with HindIII. The 2.7 kb ScaI-HindIII fragment from pPX163 and the 1.4 kb ScaI-HindIII fragment from pPX167 were isolated and gel purified. The two ScaI-HindIII fragments were subsequently ligated together.

Figure 31:
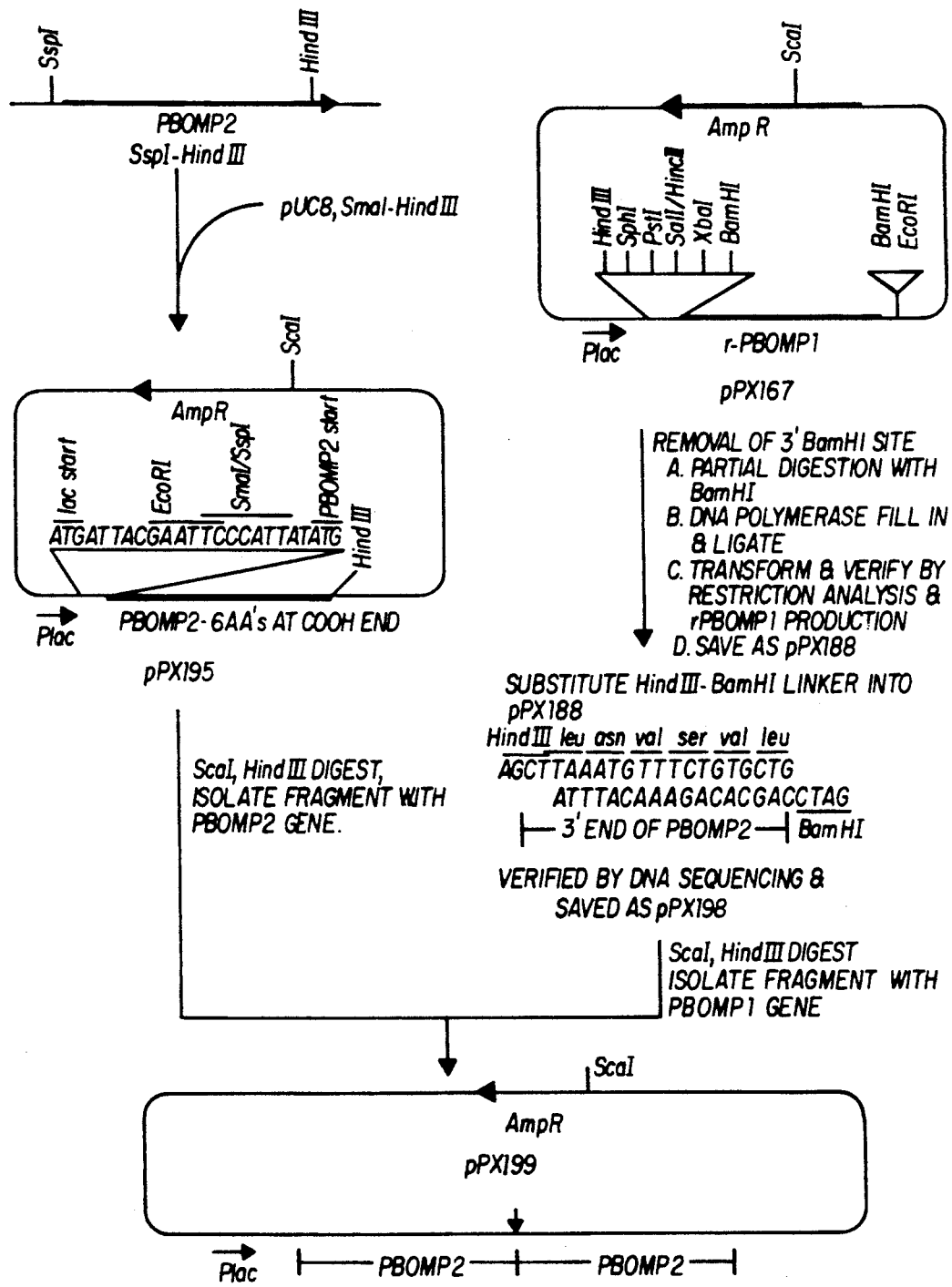

FIG. 31 is a schematic representation of the construction of plasmid pPX199 containing the PBOMP- 2:PBOMP-1 fusion protein coding sequence. See text for details of the construction.

Figure 32:

FIG. 32 represents SDS-PAGE analysis of the fatty acylated PBOMP-2: PBOMP-1 fusion protein expressed by *E. coli* cells containing plasmid pPX199. About 5 μg of the purified fusion protein was analyzed in a 15% gel (Lane 2). Prestained low molecular weight standards were run for comparison and estimation of molecular weight (Lane 1).

Figure 33:
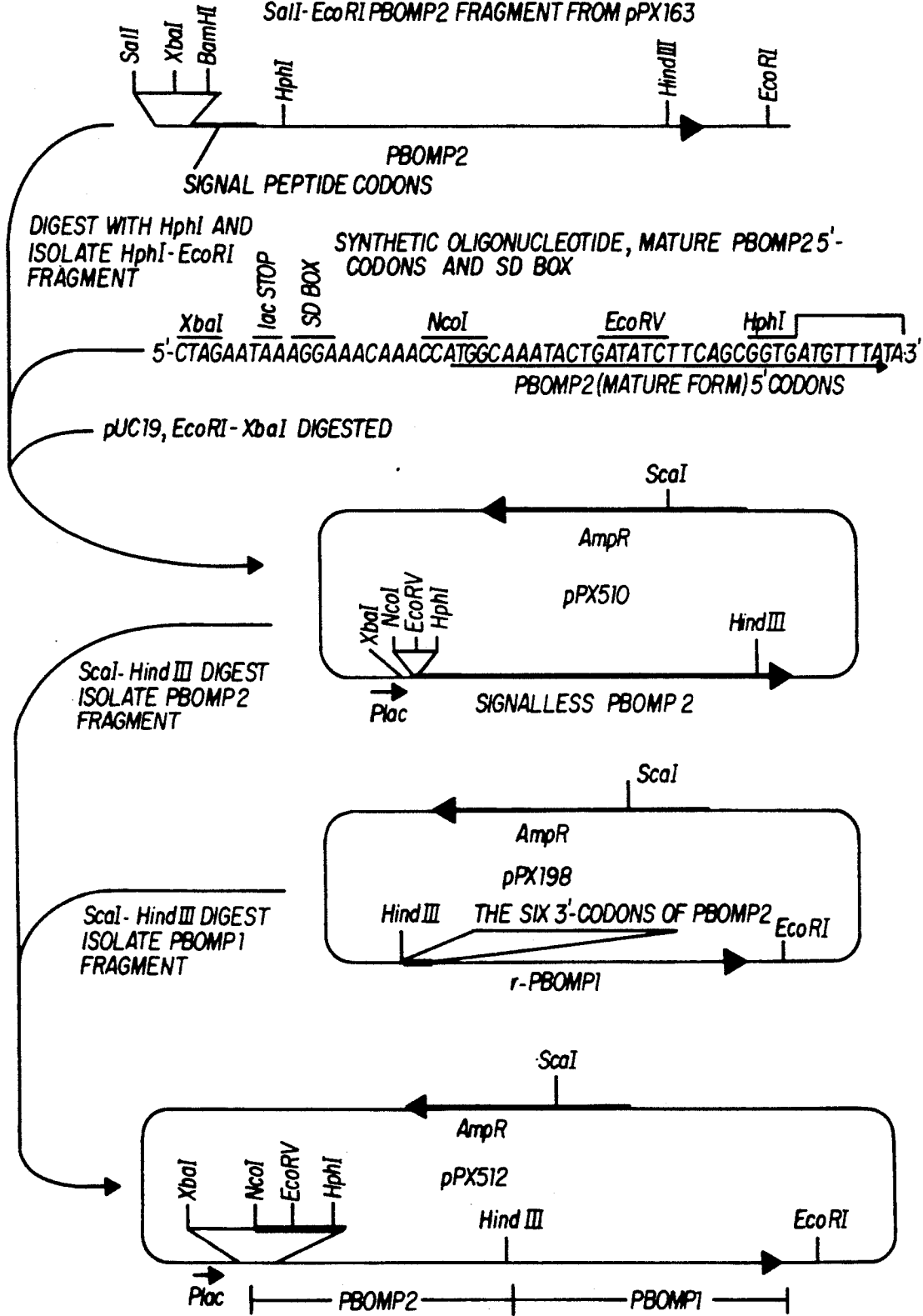

FIG. 33 is a schematic representation of the construction of plasmid pPX512 containing the PBOMP-2: PBOMP-1 fusion protein coding sequence lacking the PBOMP-2 signal sequence. In plasmid pPX512, the PBOMP-2 gene lacking the signal sequence is inserted downstream from the lac promoter. Plasmid pPX512 contains a chimeric sequence coding for mature PBOMP-2 sequence, except that the N-terminal cysteine is replaced by methionine, linked at the carboxy terminus to the PBOMP-1 sequence. See text for details of the construction.

DETAILED DESCRIPTION OF THE INVENTION

The present invention is directed to proteins and peptides related to epitopes of an approximately 16000 dalton molecular weight outer membrane protein of *H. influenzae*, i.e., PBOMP-1 and of a related approximately 16000 dalton molecular weight outer membrane protein of *H. influenzae*, i.e., PBOMP-2. The invention is directed further to fusion proteins comprising epitopes of other important proteins of *H. influenzae* including IgA protease, fimbri and outer membrane proteins. The present invention is also directed to proteins and peptides related to epitopes of a PBOMP-1: PBOMP-2 or a PBOMP-2: PBOMP-1 fusion protein. The apparent molecular weights as determined using SDS-PAGE reflect the total molecular weights of the mature (i.e., proteolytically processed) forms, including any post-translational modification(s) (e.g., fatty acylation, acetylation, etc.). The proteins and peptides of the invention can be produced using recombinant DNA methods or by chemical synthesis. Additionally, the PBOMP-1 and/or PBOMP-2 proteins and peptides of the invention can be obtained in substantially pure form from cultures of *H. influenzae* using novel and improved methods of isolation and purification. The PBOMP-1, PBOMP-2, PBOMP-1: PBOMP-2, and PBOMP-2: PBOMP-1 proteins and peptides specifying epitopes of *H. influenzae* can be used as immunogens in various vaccine formulations to protect against infection with *H. influenzae*, an etiological agent of bacterial meningitis, otitis media, epiglottitis, pneumonia, etc. The vaccine formulations are effective against both *H. influenzae* typable strains including types a, b, c, d, e, and f as well as non-typable *H. influenzae* strains.

The present invention further relates to the nucleotide sequence(s) of the genes encoding the PBOMP-1, PBOMP-2, PBOMP-1: PBOMP-2, and PBOMP-2: PBOMP-1 proteins as well as the amino acid sequences of the PBOMP-1, PBOMP-2, PBOMP-1: PBOMP-2, and PBOMP-2: PBOMP-1 proteins and polypeptide fragments thereof.

According to one embodiment of the present invention, recombinant DNA techniques are used to insert nucleotide sequences encoding PBOMP-1, PBOMP-2, PBOMP-1: PBOMP-2 and PBOMP-2: PBOMP-1 epitopes into expression vectors that will direct the expression of these sequences in appropriate host cells. These expression vector host cell systems can be used to produce PBOMP-1, PBOMP-2, PBOMP-1: PBOMP-2, and PBOMP-2: PBOMP-1, and related proteins and peptides. The gene products can be purified from cells in culture and used as immunogens in subunit vaccine formulations. Alternatively, the amino acid sequence of PBOMP-1 and PBOMP-2 proteins and peptides may be deduced either (1) from the substantially pure PBOMP-1 protein isolated from *H. influenzae* as taught herein or (2) from the *H. influenzae* nucleotide sequences contained in recombinants that express immunogenic PBOMP-1, PBOMP-2, PBOMP-1: PBOMP-2 or PBOMP-2: PBOMP-1 related proteins and peptides. These proteins and peptides may then be chemically synthesized and used in synthetic subunit vaccine formulations.

Where the expression vector that expresses the PBOMP-1, PBOMP-2, PBOMP-1: PBOMP-2 or PBOMP-2: PBOMP-1 sequence(s) is a recombinant virus, the virus itself may be used as a vaccine. Infectious recombinant viruses that express the PBOMP-1 and/or PBOMP-2 proteins and peptides and the PBOMP-1: PBOMP-2 and/or PBOMP-2: PBOMP-1 fusion proteins and peptides, and do not cause disease in a host can be used in live virus vaccine preparations to provide substantial immunity. Alternatively, inactivated virus vaccines can be prepared using "killed" recombinant viruses that express the PBOMP-1, PBOMP-2, PBOMP-1: PBOMP-2 and/or PBOMP-2: PBOMP-1 proteins and peptides.

The present invention is further directed to polyvalent antiserum and monoclonal antibody against PBOMP-1, PBOMP-2, PBOMP-1: PBOMP-2, and/or PBOMP-2: PBOMP-1 as well as methods for use of such immunoglobulin for passive immunization, and diagnostic assays for *H. influenzae*. In a particular embodiment of the invention, monoclonal antibodies may be generated against PBOMP-1, PBOMP-2, PBOMP-1: PBOMP-2 and/or PBOMP-2: PBOMP-1, related peptides.

For the purpose of description, the method of the invention can be divided into the following stages: (1) isolation and purification of PBOMP-1 protein; (2) partial amino acid sequencing of PBOMP-1; (3) generation of PBOMP-1 and/or PBOMP-2 related peptides which encompass an immunogenic region(s) of PBOMP-1 or PBOMP-2 respectively; (4) molecular cloning of genes or gene fragments encoding PBOMP-1 and PBOMP-2, and PBOMP-1: PBOMP-2 and/or PBOMP-2: PBOMP-1 fusion proteins including insertion of the genes or gene fragments into expression vectors and identification and purification of the recombinant gene products; (5) nucleotide sequencing of the genes encoding PBOMP-1 and PBOMP-2; and (6) determination of the immunopotency of the PBOMP-1, PBOMP-2 PBOMP-1: PBOMP-2 and/or PBOMP-2: PBOMP-1 proteins and related products through production of antibodies against purified and recombinant protein and peptide products. The method further encompasses (7) formulation of vaccines and (8) diagnostic assays for detection of PBOMP-1 and PBOMP-2 genes or gene product (and hence *H. influenzae*) in samples of body fluids.

5.1 Isolation and Purification of PBOMP-1

In *H. influenzae* b Eagan and other strains of *H. influenzae*, the outer membrane protein PBOMP-1 is associated with the outer membrane-cell wall complex. A necessary step in the purification of PBOMP-1 is the disruption of the bonds which keep the outer membrane proteins in tight association with the outer membrane and cell wall. This can be accomplished by the novel and improved method of the invention which comprises the following two stages: (1) isolating a PBOMP-1 enriched insoluble cell wall fraction from physically disrupted cells of *H. influenzae*, and then (2) solubilizing PBOMP-1 from the cell wall fraction by heating in the presence of a detergent which is suitable for administration to a human or digesting the cell wall fraction with lysozyme either in the presence or absence of detergent.

The novel improved method of the present invention avoids the use of denaturants and reducing agents such as sodium dodecylsulfate and 2-mercaptoethanol (see Munson et al., 1984, Infect. Immun. 49:544–49) which might destroy important epitopes and which are not suitable components for vaccine formulations for administration to humans.

5.1.1 Isolation of PBOMP-1 Enriched Insoluble Cell Wall Material from *H. influenzae*

A total cell membrane fraction may be obtained by differential sedimentation following disruption of H. influenzae cells by methods including but not limited to: sonication, grinding, by expulsion from a french press other homogenization device. The total membrane fraction may be further fractionated into inner and outer membranes by density gradient sedimentation or by differential solubilization of the inner membrane by certain detergents such as Triton X-100 TM or N-lauroyl sarcosine, sodium salt (sarcosyl). Outer membranes are preferably prepared by differential solubilization of inner membranes in 1% (W/V) sarcosyl in 10 mM HEPES-NaOH, pH 7.4. A subfraction enriched in PBOMP-1 can be produced by differential detergent extraction of other outer membrane-cell wall components. This enrichment can be accomplished, for example, by sequential extraction of the outer membrane-cell wall complex (which remains after Triton X-100 TM or sarcosyl extraction as described above) with 1% octylglucoside, nonylglucoside, zwittergent 3-14 TM, or zwittergent 3-16 TM, followed by extraction of the insoluble material with 1% sarcosyl, and then centrifugation to isolate the PBOMP-1 enriched insoluble material.

Solubilization of PBOMP-1 from the PBOMP-1 Enriched Insoluble Cell Wall Material Solubilization of the PBOMP-1 from the outer membrane-cell wall complex can be achieved in several different ways using one of the following approaches or a combination thereof: (1) PBOMP-1 can be solubilized by extraction of the PBOMP-1 enriched fraction with one or any combination of several detergents, including but not limited to deoxycholate, Triton X-100 TM, Tween 80, CHAPS, CHAPSO, dodecylmaltoside, zwittergent 3-14 TM, and zwittergent 3-16 TM, at 55° C.–6° C. for 1 hour; (2) PBOMP-1 can be solubilized by disruption of the cell wall in the PBOMP-1 enriched fraction with lysozyme, either in the presence or absence of detergent. According to a preferred embodiment the detergent is selected from: deoxycholate and polyethoxylate sorbitan monooleate (Tween-80).

Alternatively, PBOMP-1 can be isolated by extracting whole *H. influenzae* cells, outer membranes or subfractions thereof with one or a combination of detergents including but not limited to: Triton X-100 TM, sarcosyl, octylglucoside, nonylglucoside, zwittergent 3-14 TM, or zwittergent 3-16 TM. This extraction could be performed at 55°–60° C. or at room temperature in an appropriate buffer system.

After solubilization, further purification of the PBOMP-1 can be achieved by standard methods known in the art including but not limited to: ion exchange, molecular sieve, hydrophobic or reverse phase chromatography, affinity chromatography, chromatofocusing, isoelectric focusing and preparative electrophoresis.

5.2 Characterization of PBOMP-1 by Amino Acid Analysis and Sequencing of PBOMP Peptides The PBOMP-1 obtained from *H. influenzae* can be characterized by amino acid analysis in combination with partial amino acid sequencing of peptide fragments. In order to minimize the destruction and/or modification of amino acids in the purified protein it is preferable to hydrolyze the PBOMP-1 in methanesulfonic acid containing tryptamine (Simpson et al., 1970, J. Biol. Chem. 251:1936–40). In one experimental example of the present invention, such amino acid analysis was combined with amino acid sequencing of tryptic peptide fragments of PBOMP-1 to characterize the novel peptide isolated as described (see Section 6.1.1.).

Difficulties experienced during initial attempts to sequence the PBOMP-1 by Edman chemistry suggested that the N-terminus of the Haemophilus outer membrane protein is blocked. Studies by Braun (1970, Eur. J. Biochem 14: 387–391) have shown that fatty acids are linked to the N-terminal cysteinyl residue of Braun's lipoprotein of *Escherichia coli*. A palmityl moiety is amide-linked to the N-terminal cysteine; two additional fatty acids are also attached to the same cysteinyl residue via a glyceryl group that forms a thioether bond in the *E. coli* Braun lipoprotein. (Id.) Hence the PBOMP-1 obtained from *H. influenzae* was further characterized by fatty acid analysis. Such investigation indicated that the N-terminal residues of the outer membrane protein and peptides of the present invention can have covalently attached fatty acid residues. In one experimental example of the present invention, such fatty acid analysis revealed the presence of three major fatty acids, i.e., lauric acid, palmitic acid; and a derivative of palmitic acid. The acetylated proteins and peptides of the present invention having a fatty acid moiety covalently attached may be of particular utility for vaccine formulations against *H. influenzae*.

5.3 Generation of PBOMP-1 and/or PBOMP-2 Related Peptides

PBOMP-1 and/or PBOMP-2 related peptides which contain an antigenic or immunogenic region(s) of PBOMP-1 or PBOMP-2 respectively may be generated by proteolytic cleavage of the entire PBOMP-1 or PBOMP-2 protein or chemical synthesis of peptide fragments. In the latter method, peptide fragments can be chemically synthesized, for example, using an automated peptide synthesizer.

PBOMP-1 or PBOMP-2 related peptides of the present invention generated either by proteolytic digestion or chemical synthesis may be purified by standard methods known in the art including but not limited to: high pressure liquid chromatography or column chromatography using ion exchange, molecular size, hydrophobic or reverse-phase columns, affinity columns or chromatofocusing, isoelectric focusing or preparative gel electrophoresis.

The sequence of proteolytic digests of PBOMP-1 or PBOMP-2, or chemically synthesized PBOMP-1 or PBOMP-2 are determined by techniques known in the art which include but are not limited to an automated sequenator utilizing the Edman degradation procedure or the precedure of amino acid analysis, which involves hydrolysis of peptide bonds (Simpon et al., 1976, J. Biol. Chem. 251:1936-1940).

5.4 Molecular Cloning of Genes or Gene Fragments Encoding PBOMP-1 and Related PBOMPs A 16000 dalton molecular weight (MW) OMP has been detected, both by sodium dodecyl sulfate polyacrylamide gel electrophoresis (SDS-PAGE) and Western Blot analysis in all *H. influenzae* strains tested (currently several hundred). Monoclonal antibody data indicate that this protein is highly conserved (Murphy et al., 1986, Infect. Immun. 54:774-49). Thus, any *H. influenzae* strain could serve as the source for the PBOMP genes. Since many *H. influenzae* strains contain no detectable plasmids or inducible prophages, the PBOMP genes are probably chromosomal. Accordingly, the first step in the molecular cloning of DNA sequences encoding PBOMPs is the isolation of such sequences from *H. influenzae* chromosomal DNA. Hereinafter, DNA encoding *H. influenzae* genes will be referred to as "Hi DNA", and DNA encoding PBOMPs sequences will be referred to as "PBOMP DNA".

In order to generate Hi DNA fragments, the Hi DNA may be cleaved at specific sites using various restriction enzymes. Alternatively, one may use low concentrations of DNAase I to fragment the DNA, or the DNA can be physically sheared, as for example, by sonication. The linear DNA fragments may then be separated according to size by standard techniques, including, but not limited to: agarose and polyacrylamide gel electrophoresis, column chromatography (e.g., molecular sieve or ion exchange chromatography) or velocity sedimentation in sucrose gradients.

Any restriction enzyme or combination of restriction enzymes may be used to generate the Hi DNA fragment(s) containing the PBOMP sequences provided the enzyme(s) does not destroy the immunopotency of the PBOMP gene products. For example, the antigenic site of a protein can consist of from about 7 to about 14 amino acids. Thus, a protein of the size of the PBOMP peptides may have many discrete antigenic sites and therefore, many partial PBOMP polypeptide gene sequences could code for an antigenic site. Consequently many restriction enzyme combinations may be used to generate DNA fragments, which, when inserted into an appropriate vector are capable of directing the production of PBOMP specific amino acid sequences comprising different antigenic determinants.

Once the DNA fragments are generated, identification of the specific DNA fragment containing the PBOMP gene may be accomplished in a number of ways.

The DNA sequences containing the PBOMP genes may be identified by hybridization of the Hi DNA fragments with a synthetic oligonucleotide probe. Redundant synthetic oligonucleotide probes are constructed based upon the amino acid sequence of peptide fragments of the PBOMP protein. For example, synthetic oligonucleotide probes can be prepared based upon the amino acid sequence of the substantially pure PBOMP-1 protein isolated from *H. influenzae* as described in Section 5.1. These synthetic probes can be radio-labeled with $^{32}P$-adenosine triphosphate and used to screen Hi DNA libraries for clones containing PBOMP-specific gene sequences (see Anderson et al., 1983, proc. Nat'l Acad. Sci. USA 80: 6838-42).

Alternatively, the PBOMP gene DNA may be identified and isolated *after* insertion into a cloning vector in a "shotgun" approach. A large number of vector-host systems known in the art may be used. Vector systems may be either plasmids or modified viruses. Suitable cloning vectors include, but are not limited to the viral vectors such as lambda vector system gt11, gt WES.tB, Charon 4, and plasmid vectors such as pBR322, pBR325, pACYC177, pACYC184, pUC8, pUC9, pUC18, pUC19, pLG339, pR290, pKC37, pKC101 and other similar systems. The vector system must be compatible with the host cell used. Recombinant molecules can be introduced into cells via transformation, transfection or infection.

When Hi DNA containing a PBOMP gene or gene fragment is inserted into a cloning vector and used to transform appropriate host cells many copies of the PBOMP gene or gene fragment can be generated. This can be accomplished by ligating the Hi DNA fragment into a cloning vector which has complementary cohesive termini. If, however, the complementary restriction sites are not present, the ends of the DNA molecules may be modified. Such modification includes producing blunt ends by digesting back single-stranded DNA termini or by filling the single-stranded termini so that the ends can be blunt-end ligated. Alternatively, any site desired may be produced by ligating nucleotide sequences (linkers) onto the DNA termini. These ligated linkers may comprise specific chemically synthesized oligonucleotides encoding restriction site recognition sequences. For example, according to the DNA modification procedure of Maniatis, (see Maniatis et al., 1982, Molecular Cloning, Cold Spring Harbor Laboratory, pp. 107-114) sheared DNA is treated with a restriction methylase (for example, M. EcoRI) and ligated to synthetic DNA linkers which encode a restriction site for that enzyme. The DNA is then treated with restriction endonuclease to cleave the terminal linkers (but not the modified internal restriction sites) and ligated to the appropriate vector arms. In an alternative method, the cleaved vector and PBOMP DNA fragment may be modified by homopolymeric tailing.

Identification of a cloned PBOMP gene can be accomplished by establishing a chromosomal gene bank of Hi in a vector system and screening individual clones for the production of PBOMP-1 or PBOMP-1 related protein by any of the methods described herein, including, but not limited to specific reaction with polyclonal or monoclonal antibodies against PBOMPs.

5.4.2 Insertion of PBOMP Genes into Expression Vectors

The nucleotide sequences coding for PBOMPs or portions thereof, are inserted into an appropriate expression vector, i.e., a vector which contains the necessary elements for the transcription and translation of the inserted protein-coding sequences. In a particular embodiment of the invention, the nucleotide sequences coding for both PBOMP-1 and PBOMP-2 or portions thereof are inserted into an appropriate expression vector as described in the previous sentence, infra. A variety of host-vector systems may be utilized to express the protein-encoding sequence(s). Primarily the vector system must be compatible with the host cell used. Host-vector systems include but are not limited to the following: bacteria transformed with bacteriophage DNA, plasmid DNA or cosmid DNA; microorganisms such as yeast containing yeast vectors; mammalian cell systems infected with virus (e.g., vaccinia virus, adenovirus, etc.); insect cell systems infected with virus (e.g., baculovirus). The expression elements of these vectors vary in their strength and specificities. Depending upon the host-vector system utilized, any one of a number of suitable transcription and translation elements can be used.

In order to obtain efficient expression of the gene (or a portion of the gene), a promotor must be present in the expression vector. RNA polymerase normally binds to the promotor and initiates transcription of a gene or a group of linked genes and regulatory elements (called an operon). Promotors vary in their "strength", i.e., their ability to promote transcription. For the purpose of expressing a cloned gene, it is desirable to use strong promotors in order to obtain a high level of transcription and, hence, expression of the gene. Depending upon the host cell system utilized, any one of a number of suitable promotors may be used. For instance, when cloning in $E.$ $coli$, its bacteriophages or plasmids, promotors such as the lac promotor, trp promotor, recA promotor, ribosomal RNA promotor, the PR and PL promotors of coliphage lambda and others including but not limited to lacUV5, ompF, bla, lpp and the like, may be used to direct high levels of hybrid trp-lacUV5 (tac) promotor or other $E.$ $coli$ promotors produced by recombinant DNA or other synthetic DNA techniques may be used to provide for transcription of the inserted gene.

Bacterial host cell strains and expression vectors may be chosen which inhibit the action of the promotor unless specifically induced. In certain operons the addition of specific inducers is necessary for efficient transcription of the inserted DNA; for example, the lac operon is induced by the addition of lactose or IPTG (isopropylthio-beta-D-galactoside). A variety of other operons, such as trp, pro, etc., are under different controls. The trp operon is induced when tryptophan is absent in the growth media; and the $P_L$ promotor of lambda can be induced by an increase in temperature in host cells containing a temperature sensitive lambda represor, e.g., cI857. In this way, greater than 95% of the promotor-directed transcription may be inhibited in uninduced cells. Thus, expression of the genetically engineered PBOMP protein or peptide thereof may be controlled. This is important if the protein product of the cloned gene is lethal or detrimental to host cells. In such cases, transformants may be cultured under conditions such that the promotor is not induced, and when the cells reach a suitable density in the growth medium, the promotor can be induced for production of the protein.

One such promotor/operator system is the so-called "tac" or trp-lac promotor/operator system (Russell and Bennett, 1982, Gene 20:231-243; DeBoer, European Patent Application, 67,540 filed May 18, 1982). This hybrid promotor is constructed by combining the −35 b.p. (−35 region) of the trp promotor and the −10 b.p. (−10 region or Pribnow box) of the lac promotor (the sequences of DNA which are the RNA polymerase binding site). In addition to maintaining the strong promotor characteristics of the tryptophan promotor, tac is also controlled by the lac repressor.

When cloning in a eucaryotic host cell, enhancer sequences (e.g., the 72 bp tandem repeat of SV40 DNA or the retroviral long terminal repeats or LTRs, etc.) may be inserted to increase transcriptional efficiency. Enhancer sequences are a set of eucaryotic DNA elements that appear to increase transcriptional efficiency in a manner relatively independent of their position and orientation with respect to a nearby gene. Unlike the classic promoter elements (e.g., the polymerase binding site and the Goldberg-Hogness "TATA" box) which must be located immediately 5' to the gene, enhancer sequences have a remarkable ability to function upstream from, within, or downstream from eucaryotic genes; therefore, the position of the enhancer sequence with respect to the inserted gene is less critical.

Specific initiation signals are also required for efficient gene transcription and translation in procaryotic cells. These transcription and translation initiation signals may vary in "strength" as measured by the quantity of gene specific messenger RNA and protein synthesized, respectively. The DNA expression vector, which contains a promotor, may also contain any combination of various "strong" transcription and/or translation initiation signals. For instance, efficient translation in $E.$ $coli$ requires a Shine-Dalgarno (SD) sequence about 7–9 bases 5' to the initiation codon (ATG) to provide a ribosome binding site. Thus, any SD-ATG combination that can be utilized by host cell ribosomes may be employed. Such combinations include but are not limited to the SD-ATG combination from the cro gene or the N gene of coliphage lambda, or from the $E.$ $coli$ tryptophan E, D, C, B or A genes. Additionally, any SD-ATG combination produced by recombinant DNA or other techniques involving incorporation of synthetic nucleotides may be used.

Any of the methods previously described for the insertion of DNA fragments into a vector may be used to ligate a promotor and other control elements into specific sites within the vector.

Accordingly, $H.$ $influenzae$ genetic sequences containing those regions coding for the PBOMP proteins or peptides can be ligated into an expression vector at a specific site in relation to the vector promotor and control elements so that when the recombinant DNA molecule is introduced into a host cell the foreign genetic sequence can be expressed (i.e., transcribed and translated) by the host cell. In a specific embodiment of the invention, regions coding for both PBOMP-1 and PBOMP-2 proteins or peptides can be ligated into an expression vector. The relation or orientation of the PBOMP sequences to the vector promoter and control elements will determine whether the genetic sequence expressed is a PBOMP-1: PBOMP-2 or PBOMP-2: PBOMP-1 fusion protein or peptide fragments, thereof. The recombinant DNA molecule may be introduced into appropriate host cells (including but not limited to bacteria, virus, yeast, mammalian cells or the like) by transformation, transduction or transfection (depending upon the vector/host cell system). Transformants are selected based upon the expression of one or more appropriate gene markers normally present in the vector, such as ampicillin resistance or tetracycline resistance in pBR322, or thymidine kinase activity in eucaryotic host systems. Expression of such marker genes should indicate that the recombinant DNA molecule is intact and is replicating. Expression vectors may be derived from cloning vectors, which usually contain a marker function. Such cloning vectors may include, but are not limited to the following: SV40 and adenovirus, vaccinia virus vectors, insect viruses such as baculoviruses, yeast vectors, bacteriophage vectors such as lambda gt-WES-lambda B, Charon 28, Charon 4A, lambda gt-1-lambda BC, lambda gt-1-lambda B, M13mp7, M13mp8, M13mp9, or plasmid DNA vectors such as pBR322, pAC105, pVA51, pACYC177, pKH47, pACYC184, pUBI10, pMB9, pBR325, Col El, pSC101, pBR313, pML21, RSF2124, pCRl, RP4, pBR328 and the like.

Transfer of drug resistance factors between *H. influenzae* and *E. coli* via conjugation (Stuy, 1979, J. Bact. 139:520–529); and transformation (Mann, 1979, Plasmid 2:503–505) and cloning of Haemophilus chromosomal genes in *E. coli* (Mann et al., 1980, Gene 3:97–112) indicate that at least some genes can be efficiently expressed in both organisms; and that the basic mechanisms of transcriptional and translational control may be similar.

In the particular embodiment in the examples of the present invention, an *E. coli* plasmid system was chosen as the expression vector. The invention, however, is not limited to the use of such *E. coli* expression vector.

Genetic engineering techniques could also be used to further characterize and/or adapt the cloned gene. For example, site directed mutagenesis of the gene encoding a PBOMP protein could be used to identify regions of the protein responsible for generation of protective antibody responses. It could also be used to modify the protein in regions outside the protective domains, for example, to increase the solubility of the protein to allow easier purification.

5.4.3 Identification and Purification of the Expressed Gene Products

Expression vectors containing foreign gene inserts can be identified by three general approaches: (1) DNA-DNA hybridization using probes comprising sequences that are homologous to the foreign inserted gene; (2) presence or absence of "marker" gene functions (e.g., resistance to antibiotics, transformation phenotype, thymidine kinase activity, etc.); and (3) expression of inserted sequences based on the physical, immunological or functional properties of the gene product.

Once a recombinant which expresses a PBOMP gene is identified, the gene product should be analyzed. Immunological analysis is especially important because the ultimate goal is to use the gene products or recombinant viruses that express such products in vaccine formulations and/or as antigens in diagnostic immunoassays.

A variety of antisera are available for analyzing immunoreactivity of the product, including, but not limited to polyvalent antisera and monoclonal antibodies described in Section 6.2., infra.

Identification of the proteins and peptides of the invention requires that the PBOMP related protein or peptide be immunoreactive to a variety of antibodies directed against PBOMP or its analogs and derivatives.

The protein or peptide should be immunoreactive whether it results from the expression an entire PBOMP gene sequence, a portion of the gene sequence or from two or more gene sequences which are ligated to direct the production of fusion proteins. This reactivity may be demonstrated by standard immunological techniques, such as radioimmunoprecipitation, radioimmune competition, ELISA or immunoblots.

Once the *H. influenzae* PBOMP related protein is identified, it may be isolated and purified by standard methods including chromatography (e.g., ion exchange, affinity, and sizing column chromatography), centrifugation, differential solubility, or by any other standard techniques for the purification of proteins.

Alternatively, once an immunoreactive *H. influenzae* PBOMP related protein produced by a recombinant is identified, the amino acid sequence of the immunoreactive protein can be deduced from the nucleotide sequence of the chimeric gene contained in the recombinant. As a result, the protein can be synthesized by standard chemical methods known in the art (e.g., see Hunkapiller et al., 1984, Nature 310: 105–111).

In a particular embodiment of the present invention such peptides, whether produced by recombinant DNA techniques or by chemical synthetic methods, include but are not limited to all or part of the amino acid sequences substantially as depicted in FIG. 11 and/or FIG. 15 including altered sequences in which functionally equivalent amino acid residues are substituted for residues within the sequence resulting in a silent change. For example, one or more amino acid residues within the sequence can be substituted by another amino acid of a similar polarity which acts as a functional equivalent, resulting in a silent alteration. Substitutes for an amino acid within the sequence may be selected from other members of the class to which the amino acid belongs. For example, the non-polar (hydrophobic) amino acids include glycine, alanine, leucine, isoleucine, valine, proline, phenylalanine, tryptophan and methionine. The polar neutral amino acids include serine, threonine, cysteine, tyrosine, asparagine, and glutamine. The positively charged (basic) amino acids include arginine, lysine and histidine. The negatively charged (acidic) amino acids include aspartic and glutamic acid.

5.5 Nucleotide Sequencing of PBOMP Genes

Once the fragments of DNA containing the PBOMP genes have been identified, the actual nucleotide sequences of these genes can be ascertained by sequence analysis of the DNA. The sequential order of the base pairs can be determined by either of two methods, the method of Maxam and Gilbert (Maxam and Gilbert, 1980, Methods in Enzymology, 65:49) or the dideoxy method (Sanger et al., 1977, Proc. Nat'l Acad. Sci. USA 74:5463). The actual start and stop signals of the PBOMP genes can be ascertained by analysis of the nucleotide sequence for open reading frames (Rosenberg et al., 1979, Ann. Rev. Genet. 13:319). If more than one open reading frame is found on a particular DNA fragment, the identity of the actual gene could be confirmed by comparing the predicted amino acid sequence of the gene product to the amino acid sequence of the PBOMP. The location of the proper reading frame may also be determined by use of gene fusions.

5.6 Determination of Immunopotency of PBOMPS and PBOMP Associated Peptides

Experience with antibodies to the capsular polysaccharide of type b *Haemophilus influenzae* i.e., PRP, shows that the ability of the antibodies to kill the bacteria in in vitro assays and to protect against challenge with Hib in animal model systems is closely correlated with the ability to elicit a protective immune response in human infants.

Anti-PBOMP antibodies elicited in response to the PBOMP proteins and peptides of this invention which include but are not limited to PBOMP-1 and/or PBOMP-2 proteins and/or PBOMP-1: PBOMP-2 and PBOMP-2: PBOMP-1 fusion proteins can be tested using similar in vitro assay systems and animal model system to demonstrate the ability to kill both Hi and Hib cells and to protect in animal model systems from challenge with Hib. In particular embodiments of the invention, antibodies may be elicited in response to chemically synthesized PBOMP peptides or PBOMP peptides generated by proteolytic cleavage of the PBOMP protein. In a preferred embodiment, such PBOMP peptide fragments would be coupled to a protein carrier, e.g. thyroglobulin, bovine serum albumin, diptheria toxin or detoxified toxin (toxoid), tetanus toxin or toxoid, pseudomonas toxin or toxoid, stapholococcus toxin or toxoid, pertussis toxin or toxoid, $CRM_{197}$, etc. $CRM_{197}$ is distinguished from native diphtheria toxin by a single amino acid. However $CRM_{197}$ and native diphtheria toxin are immunologically indistinguishable. For a detailed description of $CRM_{197}$, see U.S. Pat. No. 4,673,574, issued Jun. 16, 1987, and references incorporated therein. The results from these systems should show a similar correlation with the potential of each of the PBOMPs to elicit a protective immune response and to serve in a vaccine for human infants, children and adults.

An in vitro complement mediated bactericidal assay system (Musher et al., 1983, Infect. Immun. 39:297-304; Anderson et al., 1972, J. Clin. Invest. 51:31-38) which has been used previously for measuring bactericidal activity of antibodies of PRP and lipopolysaccharide (LPS) against *H. influenzae* could be used to determine whether or not antibody directed against a particular PBOMP peptide or fragment thereof has bactericidal activity against type b *H. influenzae* and non-typable *H. influenzae*. These assays can be performed against a relatively large number of clinical isolates of both types of bacteria to determine whether a broad range of strains are killed. See Sections 7.1, 9.4, and 10.5 (infra) for illustrative examples of such in vitro bactericidal assays.

Further data on the ability of a PBOMP or fragment thereof to elicit a protective antibody response may be generated by use of the infant rat meningitis model system (Smith et al., 1973, Infect. Immun. 8:278-290). Infant rats challenged before the sixth day of life, with a suitable dose of *H. influenzae* type b develop bacteremia and a fatal meningitis similar to that seen in human infants. If antibody which is bactericidal against a challenge strain is used to passively immunize infant rats prior to challenge, then they are protected from meningitis and death. Antibodies directed against the current vaccine for type b Haemophilus, PRP, are protective in the infant rat model system. Passive protection against type b Haemophilus meningitis could be demonstrated by immunizing infant rats with rabbit polyclonal anti-PBOMP antibody and subsequently challenging the rats with a lethal dose of *H. influenzae* type b. See Section 7.2 (infra) for an illustrative example of such in vivo protective antibody response elicited by the proteins and peptides of the present invention.

Data on the ability of antibody to a particular PBOMP to protect against Hi could be obtained using the chinchilla otitis media animal model system. (Barenkamp et al., 1986, Infect. Immun. 52:572-78). In this animal model, chinchillas are challenged by inoculation of the inner ear canal with Hi. An otitis media much like that seen in humans develops. Chinchillas, which have been immunized, either actively with Hi OMP's, or passively with antibody directed against Hi OMP's are protected against aural challenge with Hi. (Barenkamp et al., supra). This animal model system could be used to demonstrate the ability of antibody to a PBOMP to protect against Hi.

It is possible to demonstrate that anti-PBOMP antibodies are capable of additive protection along with anti-PRP antibodies by use of the infant rat animal model. Anti-PBOMP-1 antibodies diluted to a point at which they no longer are capable of protecting infant rats against challenge with Hib, mixed with a similar dilution of anti-PRP antibodies, may show additive protection and thus prevent death of infant rats. This additive protection might be useful for a potential combination vaccine composed of PRP, or a fragment or conjugate thereof, and the PBOMP or a fragment thereof.

5.7 Formulation of a Vaccine

Many methods may be used to introduce the vaccine formulations described below into a human or animal. These include, but are not limited to: intradermal, intramuscular, intraperitoneal, intravenous, subcutaneous and intranasal routes of administration.

5.7.1 Subunit Vaccine Formulations

One purpose of the present invention is to provide proteins or polypeptide fragments related to outer membrane proteins of *H. influenzae*, PBOMPs including PBOMP-1, PBOMP-2 and related proteins and peptides as well as PBOMP-1: PBOMP-2 and PBOMP-2: PBOMP-1 fusion proteins and related peptides, which are used as immunogens in a subunit vaccine to protect against meningitis and other disease symptoms of *H. influenzae* infections. Subunit vaccines comprise solely the relevant immunogenic material necessary to immunize a host. Vaccines made from genetically engineered immunogens, chemically synthesized immunogens and/or immunogens comprising authentic substantially pure *H. influenzae* PBOMPs isolated as described herein, which are capable of eliciting a protective immune response are particularly advantageous because there is no risk of infection of the recipients. Thus, the PBOMP related protein or fragment thereof may be purified from recombinants that express the PBOMP epitopes. Such recombinants include any of the previously described bacterial transformants, yeast transformants, or cultured cells infected with recombinant viruses that express the PBOMP epitopes (see Sections 5.4 and 5.5., supra). Alternatively, the PBOMP related protein or peptide may be chemically synthesized. To this end, the amino acid sequence of such a protein or peptide can be deduced from the nucleotide sequence of the gene which directs its expression (see Section 5.5., supra). In yet another alternative embodiment, the PBOMP related protein or peptide is isolated in substantially pure form from cultures of *H. influenzae* (see, for example, Section 5.1., supra).

Whether the immunogen is purified from recombinants or chemically synthesized, the final product is adjusted to an appropriate concentration and formulated with any suitable vaccine adjuvant. Suitable adjuvants include, but are not limited to: surface active substances, e.g., hexadecylamine, octadecylamine, octadecyl amino acid esters, lysolecithin, dimethyl-dioctadecylammonium bromide, N, N-dicoctadecyl-N'-N-bis (2-hydroxyethyl-propane diamine), methoxyhexadecylglycerol, and pluronic polyols; plyamines, e.g., pyran, dextransulfate, poly IC, polyacrylic acid, carbopol; peptides, e.g., muramyl dipeptide, dimethylglycine, tuftsin; oil emulsions; and mineral gels, e.g., aluminum hydroxide, aluminum phosphate, etc. The immunogen may also be incorporated into liposomes, or conjugated to polysaccharides and/or other polymers for use in a vaccine formulation.

In yet another embodiment of this mode of the invention, the PBOMP related protein or peptide is a hapten, i.e., a molecule that is antigenic in that it reacts specifically or selectively with cognate antibodies, but is not immunogenic in that it cannot elicit an immune response. In such case, the hapten may be covalently bound to a carrier or immunogenic molecule; for example, a large protein such as protein serum albumin will confer immunogenicity to the hapten coupled to it. The hapten-carrier may be formulated for use as a subunit vaccine.

5.7 2 Viral Vaccine Formulations

Another purpose of the present invention is to provide either a live recombinant viral vaccine or an inactivated recombinant viral vaccine which is used to protect against meningitis and other disease symptoms of *H. influenzae*. To this end, recombinant viruses are prepared that express PBOMP related epitopes (see Sections 5.4. and 5.5., supra). Where the recombinant virus is infectious to the host to be immunized but does not cause disease, a live vaccine is preferred because multiplication in the host leads to a prolonged stimulus, therefore, conferring substantially long-lasting immunity. The infectious recombinant virus when introduced into a host can express the PBOMP related protein or polypeptide fragment from its chimeric gene and thereby elicit an immune response against *H. influenzae* antigens. In cases where such an immune response is protective against subsequent *H. influenzae* infection, the live recombinant virus itself may be used in a preventative vaccine against *H. influenzae* infection. Production of such recombinant virus may involve both in vitro (e.g., tissue culture cells) and in vivo (e.g., natural host animal) systems. For instance, conventional methods for preparation and formulation of smallpox vaccine may be adapted for the formulation of live recombinant virus vaccine expressing a PBOMP related protein or polypeptide.

Multivalent live virus vaccines can be prepared from a single or a few infectious recombinant viruses that express epitopes of organisms that cause disease in addition to the epitopes of *H. influenzae* PBOMPs. For example, a vaccinia virus can be engineered to contain coding sequences for other epitopes in addition to those of *H. influenzae* PBOMPs. Such a recombinant virus itself can be used as the immunogen in a multivalent vaccine. Alternatively, a mixture of vaccinia or other viruses, each expressing a different gene encoding for different epitopes of PBOMPs and/or other epitopes of other disease causing organisms can be formulated in a multivalent vaccine.

Whether or not the recombinant virus is infectious to the host to be immunized, an inactivated virus vaccine formulation may be prepared. Inactivated vaccines are "dead" in the sense that their infectivity has been destroyed, usually by chemical treatment (e.g., formaldehyde). Ideally, the infectivity of the virus is destroyed without affecting the proteins which carry the immunogenicity of the virus. In order to prepare inactivated vaccines, large quantities of the recombinant virus expressing the PBOMP related protein or polypeptide must be grown in culture to provide the necessary quantity of relevant antigens. A mixture of inactivated viruses which express different epitopes may be used for the formulation of "multivalent" vaccines. In certain instances, these "multivalent" inactivated vaccines may be preferable to live vaccine formulation because of potential difficulties with mutual interference of live viruses administered together. In either case, the inactivated recombinant virus or mixture of viruses should be formulated in a suitable adjuvant in order to enhance the immunological response to the antigens. Suitable adjuvants include, but are not limited to: surface active substances, e.g., hexadecylamine, octadecyl amino acid esters, octadecylamine, lysolecithin, dimethyl-dioctadecylammonium bromide, N, N-dicoctadecyl-N'-N-bis (2-hydroxyethyl-propane diamine), methoxyhexadecylglycerol, and pluronic polyols; plyamines, e.g., pyran, dextransulfate, poly IC, polyacrylic acid, carbopol; peptides, e.g., muramyl dipeptide, dimethylglycine, tuftsin; oil emulsions; and mineral gels, e.g., aluminum hydroxide, aluminum phosphate, etc.

5.7 3 Passive Immunity and Anti-Idiotypic Antibodies

Instead of actively immunizing with viral or subunit vaccines, it is possible to confer short-term protection to a host by the administration of pre-formed antibody against an epitope of *H. influenzae*. Thus, the vaccine formulations can be used to produce antibodies for use in passive immunotherapy. Human immunoglobulin is preferred in human medicine because a heterologous immunoglobulin may provoke an immune response to its foreign immunogenic components. Such passive immunization could be used on an emergency basis for immediate protection of unimmunized individuals exposed to special risks, e.g., young children exposed to contact with bacterial meningitis patients. Alternatively, these antibodies can be used in the production of anti-idiotypic antibody, which in turn can be used as an antigen to stimulate an immune response against *H. influenzae* PBOMP epitopes.

5.8 Diagnostic Assays

Yet another purpose of the present invention is to provide reagents for use in diagnostic assays for the detection of PBOMP antigens (and hence *H. influenzae*) in various body fluids of individuals suspected of *H. influenzae* infection.

5.8.1 Immunoassays

In one mode of this embodiment, the PBOMP related proteins and peptides of the present invention may be used as antigens in immunoassays for the detection of *H. influenzae* in various patient tissues and body fluids including, but not limited to: blood, spinal fluid, sputum, etc.

The antigens of the present invention may be used in any immunoassay system known in the art including, but not limited to: radioimmunoassays, ELISA assays, "sandwich" assays, precipitin reactions, gel diffusion precipitin reactions, immunodiffusion assays, agglutination assays, fluorescent immunoassays, protein A immunoassays and immunoelectrophoresis assays, to name but a few.

5.8.2 Nucleic Acid Hybridization Assay

In another mode of this embodiment, the novel nucleotide sequence of the genes encoding the PBOMP related protein and peptides of the present invention may be used as probes in nucleic acid hybridization assays for the detection of *H. influenzae* in various patient body fluids, including but not limited to: blood, spinal fluid, sputum, etc.

The nucleotide sequences of the present invention may be used in any nucleic acid hybridization assay system known in the art including, but not limited to: Southern blots (Southern, 1975, J. Mol. Biol. 98:508); Northern blots (Thomas et al., 1980, Proc. Nat'l Acad. Sci. USA 77:5201-05); colony blots (Grunstein et al., 1975, Proc. Nat'l Acad. Sci. USA 72:3961-65), etc.

The following series of Examples are presented for purposes of illustration and not by way of limitation on the scope of the present invention.

6 EXAMPLES: ISOLATION AND CHARACTERIZATION OF NATURAL AND RECOMBINANT DNA-DERIVED PBOMPs

6.1 Isolation, Purification and Analysis of PBOMP-1

In one series of experiments, PBOMP-1 substantially free of other cell wall components was obtained from H. influenzae as follows:

H. influenzae Eagan was grown overnight on either brain heart infusion medium containing 10 ug/ml hemin and 1 ug/ml NAD (BHI-XV) or mMIC (modification of Herriott et al., 1970, J. Bacteriol. 101: 513-16) media. Following centifugation at 10,000×g for 15 minutes at 4° C., the supernatant was discarded into Rocal II ™ disinfectant. The cell pellet was weighed and suspended in 10 mM HEPES-NaOH (pH 7.4), 1 mM EDTA, with a volume of buffer equal to about five times the wet weight of the cells. The cell suspension was then sonicated for 5 minutes in an ice bath in 100 ml aliquots with a Branson Model 350 sonifier cell disruptor (Branson Sonic Power, Danbury, Conn.) at 60% power on a pulse setting. Following sonication, the disrupted cell suspension was centrifuged at 10,000×g for 5 minutes at 4° C. to remove unbroken cells. The sedimented unbroken cells were then weighed and re-sonicated as before in a volume of 10 mM HEPES-NaOH pH 7.4, 1 mM EDTA, equivalent to about five times the wet weight of the unbroken cells. The total membrane fraction was obtained as a pellet following addition of sufficient NaCl to provide a final concentration of 0.5M NaCl and ultracentrifugation of the broken cellular material at 100,000×g for about 1 hour.

An outer membrane-cell wall complex was then obtained by removing the inner membrane components from the total membrane fraction by repeated extraction of the total membrane fraction with 1% sarcosyl, in 10 mM HEPES-NaOH, pH 7.4. The insoluble residue containing the outer membrane cell wall fraction was isolated by centrifugation at 350,000×g for 30 minutes, suspended in 50 mM Tris pH 8.0, 5 mM EDTA, and stored overnight at 4° C.

A PBOMP-1 cell wall complex was isolated from the rest of the other proteins in the outer membrane fraction by sequential extraction of the outer membrane-cell wall fraction with octylglucoside (twice), followed by sarcosyl (twice) Both detergents were used at 1% (w/v) in 50 mM Tris, 5 mM EDTA, pH 8.0. Extractions were carried out at room temperature (20° C.) for 30 minutes each. The mixture was then centrifuged at 100,000×g for 1 hour. The insoluble, sedimented material remaining after extraction with octylglucoside and sarcosyl is a PBOMP-1-cell wall complex.

PBOMP-1 was solubilized by two methods: (1) heating to 60° C. for 1 hour in the presence of one of several detergents; or (2) disruption of the cell wall by lysozyme digestion at 37° C. for 1 hour in the presence or absence of detergent. Following either (1) or (2), soluble PBOMP-1 was separated from insoluble material by centrifugation at 100,000×g for 1 hour at 15° C. In neither procedure (1) nor (2) was the particular detergent chosen critical for the solubilization. Indeed, all detergents tested to date (including: deoxycholate, Triton X-100 ™, Tween-80, CHAPS, CHAPSO, dodecylmaltoside, zwittergent 3-14 ™ and zwittergent 3-16 ™) are effective in the heat dependent solubilization as well as the lysozyme induced solubilization. Additionally, octylglucoside is very effective in the lysozyme induced solubilizations and was used routinely at 1% (w/v) final concentration. From 40 g wet weight cells, it was possible typically to isolate about 8 mg of PBOMP-1, substantially free from other cell wall components. This substantially pure PBOMP-1 preparation was analyzed in an SDS PAGE system to determine the relative molecular weight of the reduced denatured form of this protein and to assess its purity (FIG. 1).

Samples were prepared for analysis by SDS-PAGE by adjusting them to 0.1M Tris-HCl, pH 7.0, 25 mM dithiothreitol, and 2% SDS with 5X concentrated sample buffer, then heating for 5 minutes at 100° C. Prior to electrophoresis all samples were adjusted to 6% (w/v) sucrose and 0.001% bromophenol blue. Most routine analyses were performed using the Bio-Rad Mini Protean Gel System (Redmond, Calif.). Gels were 1.5 mm thick and the separating gel contained 15% acrylamide with an acrylamide to bis ratio of 30:0.8, 0.375M Tris-HCl (pH 8.8) and 0.1% SDS. The stacking gel contained 4.8% acrylamide with the same ratio of acrylamide to bis, 125 mM Tris, HCl (pH 7.0), and 0.1% SDS per gel. Following electrophoresis gels were stained for at least 1 hour with 0.125% (w/v) Coomasie blue in ethanol: acetic acid: water (5:1:5), then destained in the same solvent system without the blue dye. Pre-stained low molecular weight standards which included the following: ovalbumin, 43,000; alpha-chymotriypsinogen, 25,700; Beta-lactoglobulin, 18,400; lysozyme, 14,300; bovine trypsin inhibitor, 6,200; insulin (A and B Chains), 2,300 and 3,400 (BRL, Bethesda, Md.) were used to assist in the determination of the relative molecular weight of the PBOMP-1.

Further purification of PBOMP-1 can be achieved by standard methods such as ion exchange chromatography, molecular sieving, hydrophobic or reserve phase chromatography, chromatofocusing, gel electrophoresis and the like.

6.1.1 Characterization of PBOMP-1 by Amino Acid Composition and Sequence

Amino acid analysis was performed according to the procedure of Simpson et al., (1976, J. Biol. Chem. 251:1936-1940). Hydrolysis was accomplished by heating 0.5-1 mg of protein in 0.1 ml 4N methane sulfonic acid under vacuum in a thick-walled sealed glass tube at 100° C. for 22 hours. The quantity of each amino acid is obtained by comparison of the areas under the various peaks with areas obtained using known quantities of standard amino acids. Results obtained are illustrated in Table 1.

TABLE 1

| AMINO ACID COMPOSITION OF PBOMP-1[a] | |
|---|---|
| Amino Acid Residues | Number |
| Aspartic Acid (Asp + Asn) | 15 |

TABLE 1-continued
AMINO ACID COMPOSITION OF PBOMP-1[a]

| Amino Acid Residues | Number |
|---|---|
| Threonine | 6 |
| Serine | 7 |
| Glutamic Acid (Glu + Gln) | 12 |
| Proline | 3 |
| Glycine | 18 |
| Alanine | 19 |
| Cysteine | 1 |
| Valine | 10 |
| Methionine | 0 |
| Isoleucine | 4 |
| Leucine | 11 |
| Tyrosine | 13 |
| Phenylalanine | 4 |
| Lysine | 8 |
| Histidine | 2 |
| Arginine | 7 |
| Tryptophan | 0 |

[a] The apparent molecular weight of PBOMP-1 was 15,057 daltons. The total number of amino acid residues was 140.

Initial attempts at sequencing the PBOMP-1 using Edman chemistry failed to yield satisfactory results because of a blocked N-terminal residue. In order to obtain partial amino acid sequence information, it has been necessary to enzymatically digest the 16,000 dalton molecular weight PBOMP with proteolytic enzymes to obtain peptide fragments that are amenable to sequence analysis.

A proteolytic digest of the 16,000 dalton PBOMP-1 obtained using trypsin, at 27° C. for 1 hour was separated by reverse phase high pressure liquid chromatography (RP-HPLC) using a C18 column. A large hydrophobic peptide peak (T9) was isolated and subsequently immobilized on a polybrene-coated glass fiber paper prior to the start of amino acid sequencing.

The T9 peptide was sequenced by Edman degradation (Edman et al., 1967, Eur. J. Biochem. 1:80–91). Each cycle from the sequenator generated an anilinothiazolinone phenylthiohydantoin (PTH) -amino acid. Analysis was performed on a reverse phase C18 HPLC cartridge column with a liquid chromatography system. The PTHs were eluted at room temperature with a sodium acetate-acetonitrile gradient and detected at 270 nanometers with a variable UV wavelength detector.

The sequence analysis of the T9 peptide is shown below: Tyr-Asn-Thr-Val-Tyr-Phe-Gly-Phe-Asp-Lys-Tyr-Asp-Ile-Thr-Gly-Phe-Tyr-Val-Thr-Ile-Asp-Ala-Asp-Ala-Ala-Tyr-Leu-Asn-Ala-Thr-Pro-Ala-Ala.

The T9 peptide is very hydrophobic containing 8 aromatic amino acids (5 Tyr, 3 Phe) and 5 aliphatic side chain amino acids (1 Leu, 2 Val, 2 Ile). The tyrosine content of this peptide is high but is consistent with the total amino acid composition of PBOMP-1 (Table 1). Additionally, PBOMP-1 is unusual in that it contains 13 tyrosines, but no methionine or tryptophan.

6.1.2 Characterization of PBOMP-1 by Fatty Acid Analysis

As indicated in Section 6.1.1., initial attempts to sequence PBOMP-1 by Edman degradation did not yield satisfactory results because of a blocked N-terminal residue. Fatty acid analysis of purified *H. influenzae* PBOMP-1 was performed to investigate whether covalently linked fatty acyl groups could be identified on the PBOMP-1 peptide.

Prior to fatty acid analysis, PBOMP-1 protein isolated as described above in Section 6.1. was extracted exhaustively with a mixture of organic solvents, i.e., chloroform:methanol (2:1) and with deoxycholate detergent to remove any trace contaminants of endogenous lipids, phospholipids, etc. The denuded protein was obtained either by acetone precipitation or by exhaustive dialysis and dried by lyophilization. A known amount of nonadecanoic acid was added as an internal standard to the dried purified PBOMP-1 (1–3 mg) and the mixture was hydrolyzed with 200 ul of 4 N HCl at 110 C for 4 hours under a nitrogen atmosphere. Such acid hydrolysis released amide- or ester- linked fatty acids. The hyrdolysate, diluted to 2 ml with water, was extracted three times with an equal volume of hexane. The combined hexane phase was washed twice with an equal volume of saline and then dried over sodium sulfate. The fatty acids were converted into corresponding methyl esters with diazomethane (Schlenk, 1960, Anal. Chem. 32: 1412–1414) before injection into a Perkin Elmer Model 8500 gas liquid chromatograph. Separation of fatty acid methyl esters was performed on a SPB-1 fused silica capillary column (Supelco, Inc., Belefonte, Pa.). Resultant peaks were identified by comparison with known standards. Results obtained are illustrated in FIG. 16.

As demonstrated in FIG. 16, three major fatty acids are associated with PBOMP-1, i.e., lauric acid (C12), palmitic acid (C16) and a derivative of palmitic acid (C16,) which remains to be definitively identified. C16' is perhaps a branched chain fatty acid having 16 carbon atoms.

6.2 Preparation of Anti-PBOMP-1 and Anti-PBOMP-2 Antibodies

6.2.1 Preparation of Polyclonal Anti-PBOMP-1 and Anti-PBOMP-2 Antiserum

Substantially pure PBOMP-1 was used as an immunogen to prepare anti-PBOMP-1 antibodies. Partially purified PBOMP-1 enriched fractions, prepared as described in Section 6.1, were electrophoresed on 15% SDS-PAGE gels at 35 mA constant current at 10° C. The protein bands were fixed and stained as described in Section 6.1.1. PBOMP-1 bands were excised from the gels and dialyzed against phosphate buffered saline (PBS) (20 mM sodium phosphate, 150 mM NaCl, pH 7.4) until equilibrated. The acrylamide gel fragments containing PBOMP-1 were minced by passing them through a 25 gauge needle in PBS. The fragments were injected intramuscularly into New Zealand white rabbits at multiple sites. Each rabbit received a total of approximately 20 ug of PBOMP-1. Rabbits were reimmunized at two weeks and three weeks following the initial immunization. Animals were bled one week following the last immunization and the serum collected. Animals were boosted with 20 ug of PBOMP-1 in acrylamide bimonthly to maintain high titers of anti-PBOMP-1 antibodies.

Alternatively PBOMP-1, isolated as described in section 5.1, was mixed with incomplete Freund's adjuvant and emulsified. Rabbits were injected intramuscularly with approximately 20 ug of PBOMP-1 in Freund's adjuvant Animals were reimmunized two weeks and three weeks following the initial immunization and bled one week following the last immunization.

Substantially pure PBOMP-2 was used as an immunogen to prepare anti-PBOMP-2 antibodies. Partially purified PBOMP-2 enriched fractions, prepared as described in Section 6.1, were electrophoresed on 15% SDS-PAGE gels at 35 mA constant current at 10° C. The protein bands were fixed and stained as described in Section 6.1.1. PBOMP-2 bands were excised from the gels and dialyzed against phosphate buffered saline PBS until equilibrated. The acrylamide gel fragments containing PBOMP-2 were minced by passing them through a 25 gauge needle in PBS. The minced PBOMP-2 gel fragments were mixed with complete Freund's adjuvant and emusified. Rabbits were injected intramuscularly with approximately 10 ug of PBOMP-2 in Freund's adjuvant. Animals were boosted with 10 ug of the same preparation in incomplete Freund's adjuvant four weeks after the primary inoculation.

6.2.2 Production of Anti-PBOMP-1 and Anti-PBOMP-2 Monoclonal Antibodies

Hybridoma cell lines secreting antibodies to PBOMP-1 or PBOMP-2 were obtained by fusion of mouse myeloma cell line X63.Ag8.6543 with spleen cells obtained from a C57/B1 mouse immunized against H. influenzae as follows: A female C57/B1 mouse was injected intraperitoneally four times over a period of two months with $1 \times 10^6$ H. influenzae strain S2 cells. Three months later, the mouse was immunized with substantially pure PBOMP-1 or PBOMP-2 isolated from an SDS-PAGE band as described in Section 6.2.1. One month later, the mouse received an intravenous injection of total outer membranes from S2. Cell fusion was performed on the fourth day post- intravenous injection by standard procedures common to those of skill in the field (for example, Gefter et al., 1977, Somat. Cell. Genet 3:231-36).

Hybridoma cell culture supernatants were screened by a standard ELISA using H. influenzae outer membrane proteins as antigens. Assays were performed in 96 well polystyrene plates coated overnight at 4° C. with OMPs.

Plates were blocked with 40 mM Tris (pH 8.0), 150 mM NaCl, 5% nonfat dry milk (BLOTTO) (See Section 6.4.4) and washed with PBS/0.1% Tween-20. Culture supernatants diluted 1:10 in PBS/Tween-20 were added, incubated for 60 minutes at 25° C., and washed as before. Bound antibodies were detected with alkaline phosphatase-Goat F(ab')$_2$ anti-mouse (IgG, IgM) and the alkaline phosphatase substrate. Positive supernatants were then screened by dot blot analysis with purified PBOMP-1, E. coli OMP's, and S2 lipopolysaccharide (LPS). Desired hybridomas were recloned by limiting dilution (McKearn, 1980, in Monoclonal Antibodies, Kennett, McKearn and Bechtol, eds., Plenum Press, p. 374) and screened by Western blot with Hib OMP's. Selected hybridomas were injected into Balb/c mice for growth as ascites by standard procedures (Brodeur et al., 1984, J. Immunol. Meth. 71:265-72).

Seventeen of the hybridomas generated by the fusion of mouse myelomacells with spleen cells from C7/B1 mice immunized with PBOMP-2 were screened for their reactivity to PBOMP-2 using the standard ELISA assay. One of the hybridomas, designated 61-1 was found to be specific for PBOMP-2. Western blot procedures described infra, in section 6.5 5. using 61-1 as the primary antibody showed that PBOMP-2 or a PBOMP-2 like protein was conserved and expressed in the three clinical nontypable H. influenzae strains 0045E, 1939, and HST31 (see FIG. 29).

6.3 Reactivity of Anti-PBOMP-1 and Anti-PBOMP-2 Antibodies with E. coli

Figure 2A:
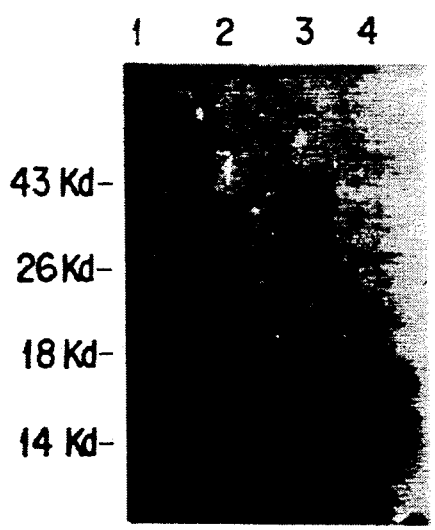

Western blot analysis of the reactivity of anti-PBOMP-1 and anti-PBOMP-2 antiserum was performed as described in Section 6.4.4, infra. Ten microliters of an overnight bacterial culture lysed in sample preparation buffer containing 2-Mercaptoethanol was applied to each lane of a 15% SDS-PAGE gel. After electrophoresis and transfer to nitrocellulose, the blots were probed with 1:250 dilutions of rabbit polyclonal anti-PBOMP-1. Incubation with horseradish peroxidase conjugated goat anti-rabbit IgG (Kirkegaard & Perry Laboratories, Gaithersburg, Md.) showed that the anti-PBOMP-1 antisera recognized the PBOMP-1 in Haemophilus and an 18,000 dalton protein in E. coli (FIG. 2A).

Figure 2B:
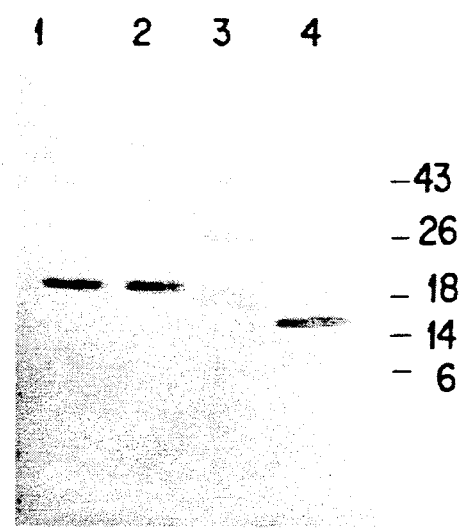

In order to confirm that an epitope of the PBOMP-1 cross-reacts with an 18,000 dalton protein of E. coli, monoclonal antibodies made against the PBOMP-1 were screened for reactivity against E. coli proteins. While most of the monoclonals screened failed to react with E. coli, one class of monoclonals, exemplified by monoclonal G1-1, reacted strongly with the PBOMP-1 of Haemophilus and with an 18,000 dalton protein in E. coli (FIG. 2B). This demonstrates that at least one epitope present on the PBOMP-1 cross-reacts with an epitope on an E. coli protein. This indicates that an antiserum against H. influenzae PBOMP1 may also protect against some E. coli infections. The anti-PBOMP-2 monoclonal antibody, 61-1, was found to cross-react weakly with a protein of about 15,000 daltons from E. coli, but showed no detectable cross-reactivity with PBOMP-1.

6.4 General Procedures Used for Preparation of Recombinant Plasmids

6.4.1 Conditions for Restriction Enzyme Digestions

Restriction endonucleases were purchased from BRL (Bethesda, Md.), IBI (New Haven, Conn.), New England Biolabs (Beverly, Mass.), or U.S. Biochemical Corporation (Cleveland, Ohio).

Restriction enzyme digestions were carried out by suspending DNA in the appropriate restriction buffer, adding restriction endonuclease, and incubating for an appropriate period of time to ensure complete digestion. One unit of enzyme is defined as the amount required to completely digest 1.0 ug of phage lambda DNA in 1 hour in a total reaction mixture of 20 ul volume. Buffers used with the various enzymes are listed below:

Low salt buffer used for ClaI, HpaI, HpaII, and KpnI digestions consisted of: 10 mM Tris (pH 8.0), 10 mM MgCl$_2$ and 10 mM dithiothreitol (DTT).

Medium salt buffer used for AluI, AvaI, EcoRII, EcoRV, HaeII, HaeIII, HincIII, HindIII, PstI, Sau3AI, SphI, SstI, SstII, TaqI, and XhoI digestions consisted of: 50 mM Tris (pH 8.0), 10 mM MgCl$_2$, 50 mM NaCl, and 10 mM DTT.

High salt buffer used for BamHI, EcoRI, PvuI, SalI and XbaI digestions consisted of: 50 mM Tris (pH 8.0), 10 mM MgCl$_2$, 150 mM NaCl and 10 mM DTT.

The buffer used for SmaI digestions consisted of: 10 mM Tris (pH 8.0), 20 mM KCl, 10 mM MgCl$_2$, and 10 mM DTT. The buffer used for ScaI digestions was: 100mM NaCl: 10 mM Tris HCl (pH 7.4); 10 mM MgCl$_2$ and 1 mM DTT. All restriction digestions were carried out at 37° C. except TaqI, which was carried out at 60° C.

6.4.2 Gel Purification of DNA Fragments

After restriction enzyme digestions, DNA fragments of varying sizes were separated and purified using gel electophoresis in low melting temperature agarose (FMC LGT agarose) using 50 mM Tris-acetate 1 mM EDTA buffer pH 7.8 at 10 volts/cm. Agarose concentrations varied from 0.8% to 1.5% depending on the size of fragments to be recovered. DNA bands were visualized by ethidium bromide fluorescence and cut out of the gel. DNA was recovered by melting the agarose at 65° C., adding 4 volumes of 0.65M NaCl, 10M Tris (pH 8.0), 1 mM EDTA to bring the mixture to a final concentration of 0.5M NaCl, loading the DNA onto a NACS column (BRL, Bethesda, Md.) equilibrated with 0.5 mM NaCl, 10 mM Tris pH 8.0, 1 mM EDTA (loading buffer), washing the column with 3-5 volumes of loading buffer, and eluting with 2-3 volumes 2M Nacl, 10 mM Tris pH 8.0, 1 mM EDTA. The DNA eluate was diluted 1:1 with double distilled $H_2O$ and precipitated with 3 volumes of ethanol. The pellet was washed with 70% ethanol, vacuum dried, and re-suspended in 10 mM Tris-HCl buffer, pH 7.5 containing 1 mM EDTA (TE buffer).

6.4.3 DNA Ligation

All ligations were accomplished using T4 DNA ligase. T4 DNA ligase was purchased from BRL (Bethesda, Md.), United States Biochemicals (Cleveland, Ohio) or Boehringer (Indianapolis, Ind.) One unit (U) of T4 DNA ligase is defined as the amount required to yield 50% ligation of HindIII fragments of bacteriophage lambda DNA in 30 minutes at 16° C. in 20 ul volume ligase buffer at a 5'-DNA termini concentration of 0.12 uM (300 ug/ml). DNA ligations were performed in ligase buffer consisting of: 50 mL Tris (pH 7.5), 10 mM $MgCl_2$, 10 mM DTT, 1 mM adenosine triphosphate). Normally a DNA concentration ranging from 20-30 ug/ml, and a molar ratio of vector to insert of 1:1 was used. T4 DNA ligase was added at a ratio of 1 U per 20 ul reaction volume. Incubations were carried out for 18-24 hours. Temperatures used were 15° C. for cohesive end ligations, and 22° C.. for blunt end ligations. If sufficient material was available, ligations were checked by analyzing a portion of the reaction mixture by agarose gel electrophoresis.

6.4.4 Protein Immuno Blot Analysis (Western Blot)

Proteins were fixed to nitrocellulose sheets for immuno blot analysis by various techniques, depending on the particular application. Phage plaques were transferred from agar plates by gently placing a sterile 8.1 cm diameter nitrocellulose disc onto the surface of a 10 cm diameter phage titer plate. The sheet was allowed to wet completely, positions were marked by punching through the filter with a sterile needle, and the filter was lifted after two minutes.

Colony blots were performed by transferring bacterial colonies to a nitrocellulose sheet, allowing the colonies to grow by placing the sheet (colony side up) on nutrient agar for 4 to 6 hours, and exposing the sheet to chloroform vapor for 30 minutes to lyse the colonies. Protein gel transfers were performed by placing an SDS-PAGE gel containing the protein mixture to be analyzed on a nitrocellulose sheet and applying horizontal electrophoresis in a Hoeffer Transphor apparatus at 0.5 A for 14 hours in 25 mM Tris 0.38M glycine pH 8.8 buffer.

Once protein transfer was complete, filters were soaked in 50 mM Tris (pH 8.0), 150 mM NaCl, 5% nonfat dry milk (BLOTTO) at 37° C. for one hour in all cases, except colony blots. When colony blots were performed, the filters were soaked overnight at 4° C. in BLOTTO containing 1 mg/ml lysozyme to digest cell debris. Filters were then absorbed with a first antibody probe at an appropriate dilution (determined by trial and error) in BLOTTO for 3 hours at 37° C., washed three times for 15 minutes with BLOTTO, absorbed with horseradish peroxidase conjugated second antibody (Kirkegaard and Perry, Gaithersburg, Md.) at a dilution of 1:500 in BLOTTO for one hour at 37° C. and washed with BLOTTO three times for 15 minutes. Filters were placed in 50 mM Tris (pH 7.0), 150 mM NaCl, 0.01% hydrogen peroxide; and 0.06% 4-Chloro-1-naphthol (Sigma Chemical Co., St. Louis, Mo.) in methanol was added. If no blue color developed within 20 minutes, the reaction was considered negative. The reaction was stopped by transferring the filter to distilled water and blotting dry.

6.4.5 Gene Fusions

Fusions of a gene or gene fragment encoding a PBOMP protein or peptide thereof to another gene such as the gene encoding alkaline phosphotase (PhoA) were carried out as described by Manoil and Beckwith (1985, Proc. Nat'l Acad. Sci. USA 82:8129-8133). Recombinant plasmids were introduced into an E. coli strain containing a deletion of the native PhoA gene and carrying a derivative of transposon Tn5 (TnPhoA) which contains an alkaline phosphatase gene, which lacks both a promotor and a membrane transport signal sequence, inserted into the left terminal repeat of Tn5 on an F-prime plasmid. Hence, production of active alkaline phosphatase enzyme requires transposition of TnPhoA such that the PhoA gene is fused in frame into an actively transcribed gene containing a membrane transport signal peptide. Such transpositions were detected by plating cells in the presence of 40 ug/ml 5-Bromo-4-Chloro-3-Indolyl Phosphate (XP, Sigma Chemical Co., St. Louis, Mo.). In the presence of this dye, colonies producing active alkaline phosphatase enzyme appear intensely blue in color while colonies which lack active alkaline phosphatase appear white.

6.4.6 DNA Filter Hybridization Analysis (Southern Blot)

DNA filter hybridization analysis was carried out according to the procedure of Southern (1975, J. Mol Biol. 98: 508). DNA to be analyzed by filter hybridization was digested with appropriate restriction endonuclease(s) and separated by agarose gel electrophoresis in 0.8% Agarose (SeaKem Portland, Me.) using 90 mM Tris-borate, 8 mM EDTA buffer and 10 volts/cm. DNA in the gel was denatured by soaking the gel in 1.5M NaCl/0.5M NaOH for 1 hour and neutralized by soaking in 1.5M NaCl/1.0M Tris-HCl for 1 hour. Denatured DNA was transferred to nitrocellulose filter paper by blotting. Following transfer of DNA, filter were washed with 6 X SSC (prepared by dilution from a 20X SSC stock containing 175.5 g NaCl and 88.2 g Na citrate/liter) and air dried. DNA fragments were fixed to the filter by baking at 80° C. for 2 hours under vacuum.

DNA hybridization probes were prepared by nick translation according to the procedure of Rigby et al., (1977, J. Mol. Biol., 113: 237-244). DNA for the probe (1-2 ug) was dissolved in 100 ul nick-translation buffer (50 mM Tris-HCl, pH 7.4, 10 mM MgSO$_4$, 10 mM DTT, 5 ug/ml bovine serum albumin, and 20 um each dGTP, dCTP, and dTTP). To this reaction mixture, 100 uCi of alpha $^{32}$P-dATP (Amersham, 2-3000 Ci/mmole), 1.0 ng of deoxyribonuclease I (Sigma Chemical Co., St. Louis, Mo.) and 10 U E. coli DNA polymerase I (Boehringer) were added and the mixture incubated at 15° C. for 45 minutes. The reaction was stopped by the addition of EDTA to 50 mM and heating to 65° C. for 10 minutes to inactivate the enzymes. The labeled DNA was precipitated by addition of three volumes of ethanol and resuspended to 50 ul of 0.3M ammonium acetate (NH$_4$OAc). The sample was loaded onto a 1 ml Biogel P-50 spin column equilibrated with 0.3M NH$_4$OAc and eluted by centrifugation at 500×g for 5 minutes. The column was washed with 100 ul 0.3M NH$_4$OAc and the eluates combined and precipitated with three volumes of ethanol. The labelled DNA pellet was vacuum dried, resuspended in TE buffer, radioactive incorporation measured in a Beckman (LS9000) scintillation counter by Cherenkov scattering.

For hybridization, filters with bound DNA were wetted with 6 x SSC and prehybridized with 6 X SSC/0.5% SDS/5X Denhardt's solution/100 ug/ml tRNA at 68° C. for 2 hours to block excess binding capacity of the filter (1 X Denhardt's solution is 0.02% Ficoll, 0.02% polyvinylpyrrolidone, 0.02% bovine serum albumin in water). The hybridization reaction was carried out in the same buffer to which 0.01M ETDA and 5-10,000,000 CPM (Cherenkov) labelled probe was added. The probe solution was heated to 90° C. for 10 minutes prior to application to denature the DNA strands, cooled to 68° C., and incubated with the filter at 68° C. for 18-24 hours. After hybridization, filters were washed with several changes of 0.1 X SSC/0.5% SDS at 68° C. in order to remove nonspecifically bound probe. Under the conditions used, DNA homologies of greater than or equal to 90% would show positive binding of the DNA probe. Filters were air dried and exposed on Kodak XAR film at −70° C. using Dupont CRONEX 'Lightning Plus' intensifying screens.

6.5 Cloning the PBOMP Genes of H. influenzae

The source of H. influenzae chromosomal DNA for cloning of the PBOMP genes was either H. influenzae KW20b (HiKW20b), a derivative of a non-encapsulated Rd strain of Hi transformed to type b+ by DNA from strain b-Eagan (Moxon et al, 1984, Clin. Invest. 73:298-306) or H. influenzae S2, (Hi S2), a spontaneous capsule-minus mutant of Hib Eagan.

To generate a phage lambda library, chromosomal DNA from Hi was sheared to an average length of about 15000 base pairs (bp), blunt ended by treatment with T4 DNA polymerase, modified with EcoRI DNA methylase, ligated to synthetic EcoRI linkers, and cloned into the recombinant Lambda phage vector Charon 4.

Figure 3:
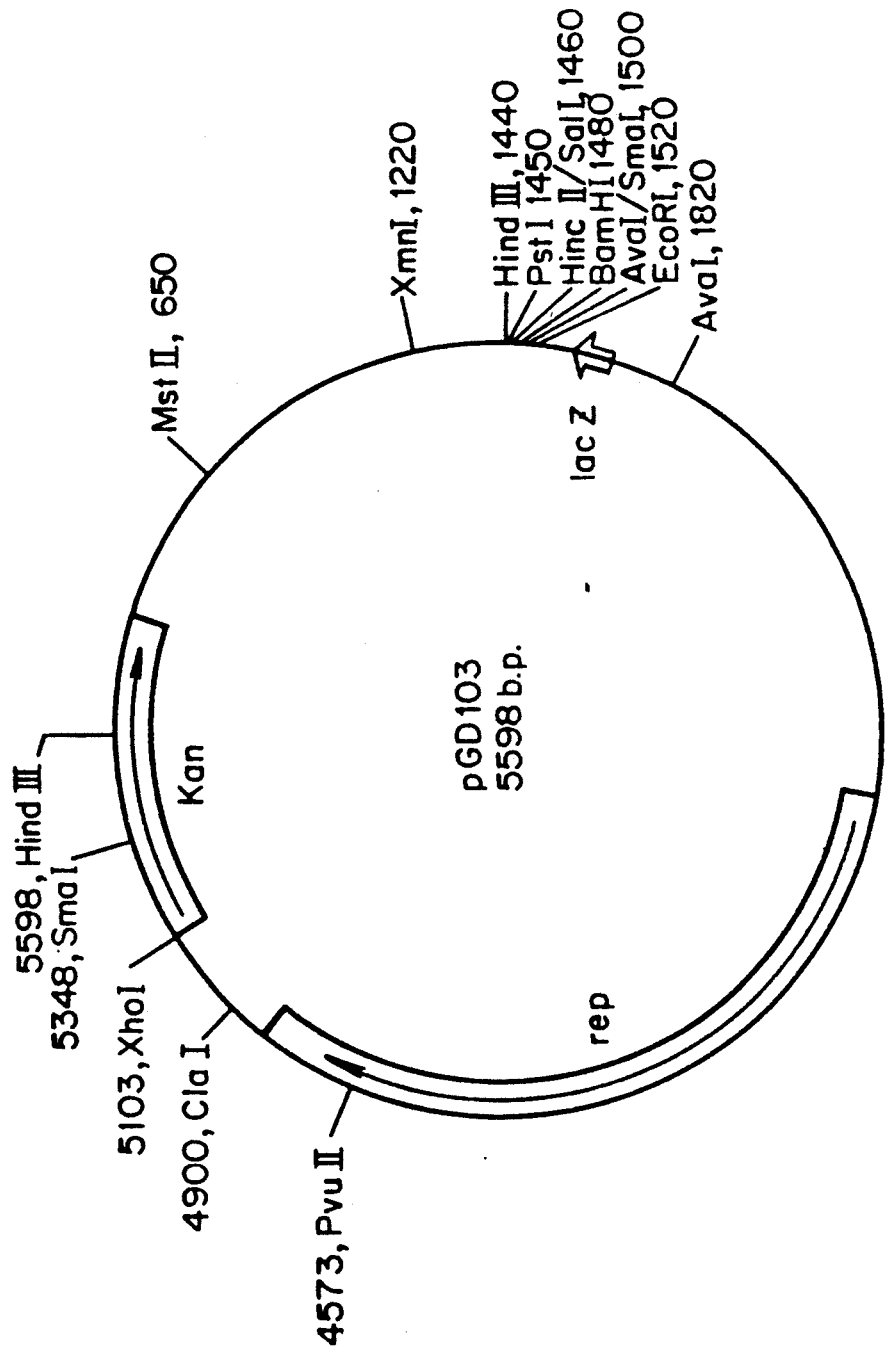

To generate a plasmid library chromosomal DNA of Hi S2 was partially cleaved with Sau3A, the 3-8 kilobase (kb) length restriction fragments thus generated were isolated, and ligated into plasmid vector pGD103 at the BamHI restriction site. This plasmid is a derivative of pLG339 (see FIG. 3: see also Stoker et al., 1982, Gene 18:335-41) and is carried in 6-8 copies/cell. It also contains the lac Z-alpha peptide and polylinker region from plasmid pUC8; and therefore, if transformed into an appropriate E. coli strain (such as JM83), allows selection of recombinant plasmids by screening for loss of the Lac+ phenotype. If cloned in the proper orientation, it is also possible that a cloned gene which is poorly expressed in E. coli could come under control of the strong, regulated lac promotor. E. coli containing recombinant plasmids were screened for production of PBOMPs using a pooled mixture of monoclonal antibodies or polyclonal anti-PBOMP-1 antiserum.

6.5.1 Construction of HI Plasmid Library

It is possible that the PBOMP-1 protein is not expressed on or is incompatible with lambda phage. In order to test this we constructed a plasmid chromosomal library of Hi S2. Cloning of E. coli OMP genes on high copy number plasmids has been shown to be toxic (see, for example, Beck et al., 1980, Nucleic Acid Res. 8:3011-3024). In order to avoid this problem, we used the low copy number plasmid pGD103 (see FIG. 3).

Chromosomal DNA from a Hi S2 was partially digested with restriction endonuclease Sau3A (BRL, Bethesda, Md.). Five hundred micrograms of DNA was digested in 5 ml restriction buffer with 50 units of Sau3A for 1 hour at 37° C. Fragments were separated by velocity sedimentation in a Beckman SW28 rotor on 10-40% sucrose gradients containing 10 mM Tris (pH 8.0), 1 mM EDTA, 1M NaCl at 140,000×g for 24 hours. Two ml fractions were collected and aliquots analyzed by agarose gel electrophoresis. Fractions containing restriction fragments of 3-8 Kb in length were pooled and concentrated in TE buffer. Plasmid pGD103 DNA was digested with BamHI endonuclease and treated with calf alkaline phosphatase (Boehringer, Indianapolis, Ind.) (1 Unit/ug DNA, 37° C.×30 minutes in restriction buffer). DNA was purified from the reaction mixture by phenol extraction and ethanol precipitation and resuspended in TE buffer. Since BamHI and Sau3A restriction enzymes form cohesive ends, no further treatment of DNAs prior to ligation was necessary.

About twenty-five ug each of Hi S2-Sau3A digested DNA and pGD103/BamHI/CAP digested DNA were mixed in 500 ml ligation buffer containing 25 U T4-ligase (Boehringer, Indianapolis, Ind.) and incubated at 15° C. for 18 hours. A 20 ul aliquot of the reaction mixture was analyzed by agarose gel electrophoresis in order to verify the ligation reaction (starting material was run in an adjacent lane). The ligation mixture was then transformed into competent E. coli JM83 (se Maniatis et al., 1982, Molecular Cloning, Cold Spring Harbor Laboratory, p. 250) incubated for 1 hour in LB-broth at 37° C., and plated on LB-agar plates containing 50 ug/ml kanamycin sulfate (Sigma Chemical Co., St. Louis, Mo.) and 40 ug/ml 5-Bromo-4-chloro-3-indolyl-Beta-D-galactopyranoside (X-gal, BRL Bethesda, Md.), and incubated 24 hours at 37° C. About 50% of the kanamycin resistant (kanR) colonies which developed were white (Lac−), indicating insertion of S2 DNA into the BamHI site in the lac region of pGD103 (Lac+ non-recombinants are blue). Ten white colonies were selected at random, amplified, and shown to contain plasmids 4-8 Kb larger than pGD103 with insertions at the vector BamHI site.

One thousand five hundred and twenty-five white colonies were picked, amplified individually, and stored frozen at −70° C. in LB broth containing 18% sterile glycerol in 96-well microtiter dishes.

6.5.2 Construction of HIB Lambda Gene Bank

High molecular weight chromosomal DNA from Hi KW20b was suspended in TE buffer at a concentration of 200 ug/ml and sheared to an average length of 15000 bp by passage through a 25 gauge needle. Protruding ends were removed by treatment with T4 DNA polymerase in 50 mM Tris, (pH 8.8), 10 mM $MgCl_2$, 20 mM $(NH_4)_2SO_4$, 10 mM DTT, 50 uM dATP, dCTP, dGTP, and dTTP) at 37° C. for 20 minutes. DNA was then modified with EcoRI DNA methylase (1 U/ug DNA) (BRL Bethesda, Md.), in 100 mM Tris (pH 8.0), 10 mM EDTA, 0.1 mM S-adenosyl-methionine) for 3 hours at 37° C. Methylation of DNA was verified by removing 1 ug of DNA from the reaction, mixing with 1 ug of unmodified lambda DNA and digesting in 20 ul of high salt restriction buffer with 5 units of EcoRI for 1 hour at 37° C. Under these conditions, the modified Hi DNA was not digested, while the added lambda DNA was digested to completion.

Twenty micrograms of modified Hi DNA was ligated to 1 ug chemically synthesized EcoRI linkers (BRL Bethesda, Md.) in a 100 ul reaction mixture using T4 DNA ligase (5U). After 18 hours, the reaction was stopped by heating to 60° C. for 20 minutes, NaCl was added to a final concentration of 150 mM, and the mixture was digested with 10 U EcoRI for 6 hours. Modified Hi DNA plus linker was separated from cleaved and unligated linkers by agarose gel electrophoresis as described above.

Prepared Hi DNA was mixed with the left and right EcoRI fragments of lambda Charon 4 DNa at a 1:1:1 molar ratio and ligated with T4 DNA polymerase for 18 hours. The ligated DNA mixture was packaged into Lambda phage particles using an in vitro packaging reaction. Five ug of ligated DNA in 4 ul $H_2O$ was added to 7 ul of 20 mM Tris (pH 8), 10 mM 2-mercaptoethanol (2-ME), 3 mM $MgCl_2$, 1 ul of 10 mM Tris, pH 7.5, 1 mM Spermidine, 2 mM putrescine, 10 mM $MgCl_2$, 1.5 mM ATP, 5 mM 2ME and 5 ul of sonic extract from E. coli BHB2690 (−1 imm 434, $cI^{ts}$, b2.red3, Eam 15, Sam7) lysate (Hohn et al., 1977, Proc. Nat'l Acad. Sci. 74:3259). The reaction mixture was incubated at 22° C. for 1 hour and packaged phages were separated by centrifugation in a 3M to 5M CsCl [in 10 mM Tris (pH 7.5), 10 mM $MgCl_2$, 0.02% gelatin (TMG buffer)] step gradient for 250,000×g for 4 hours in a Beckman SW50.1 rotor. Phage were removed from the interface and dialyzed against TMG. Titering of the phage thus prepared indicated a library of 25–30,000 independent clones of the Hi genome had been generated. The phage library was amplified by plate amplification using E. coli KH802 as a phage host to yield 5 ml of phage suspension containing $10^{-9}$ plaque forming units (PFU)/ml.

6.6 Isolation of PBOMP Genes

6.6.1 Isolation of a PBOMP Gene Encoding a Protein which Reacts with Monoclonal Antibodies against PBOMP-1

Figure 4A:
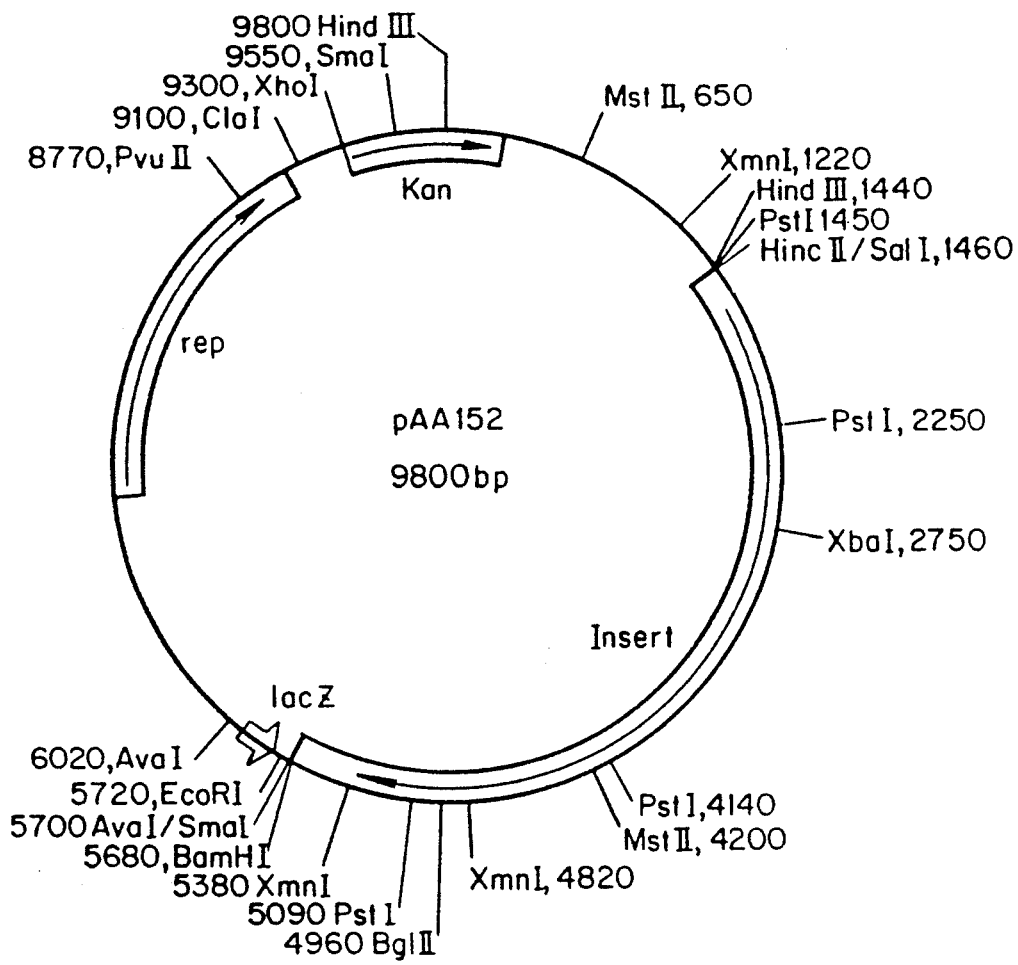
Figure 4B:
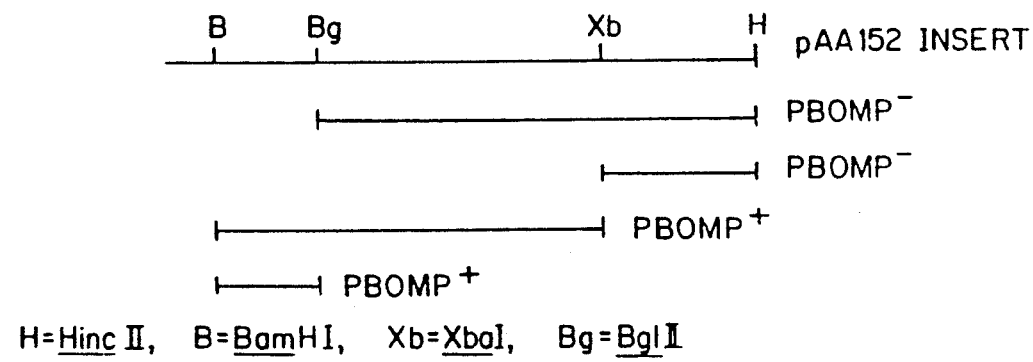
Figure 5:
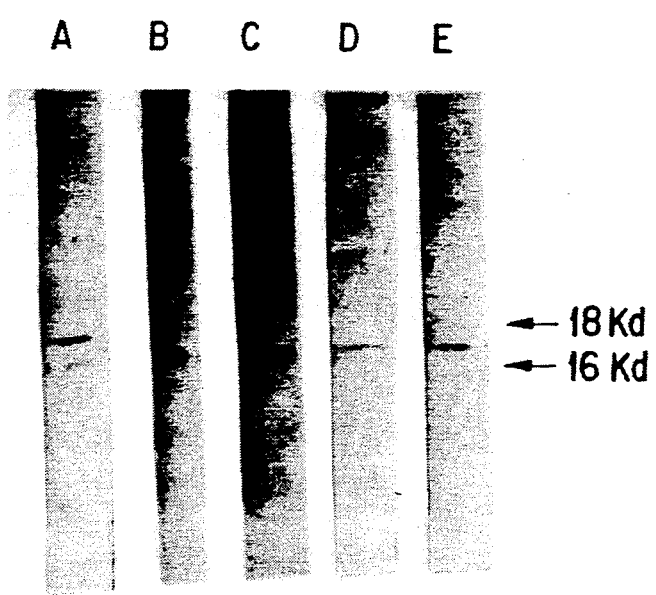

The Hi plasmid library was transferred to nitrocellulose sheets on LB-kanamycin (50 ug/ml) agar, grown for 24 hours at 37° C. and analyzed by the colony blot procedure using a mixture of five non-competing monoclonal antibodies to PBOMP-1 as a probe. A clone which reacted to the mixed monoclonal probe was isolated and the plasmid designated pAA152. FIG. 4 shows a restriction map of pAA152 which contains a 4.2 Kb Hi DNA insert in vector pGD103. Western blot analysis verified that clone pAA152 expresses a 16000 dalton protein which was recognized by polyclonal anti-PBOMP-1 and also by pooled monoclonal antibody probes. Clone pAA152 was subsequently shown to produce a protein which was recognized by each individual monoclonal antibody used in the initial pool (FIG. 5).

Figure 6:
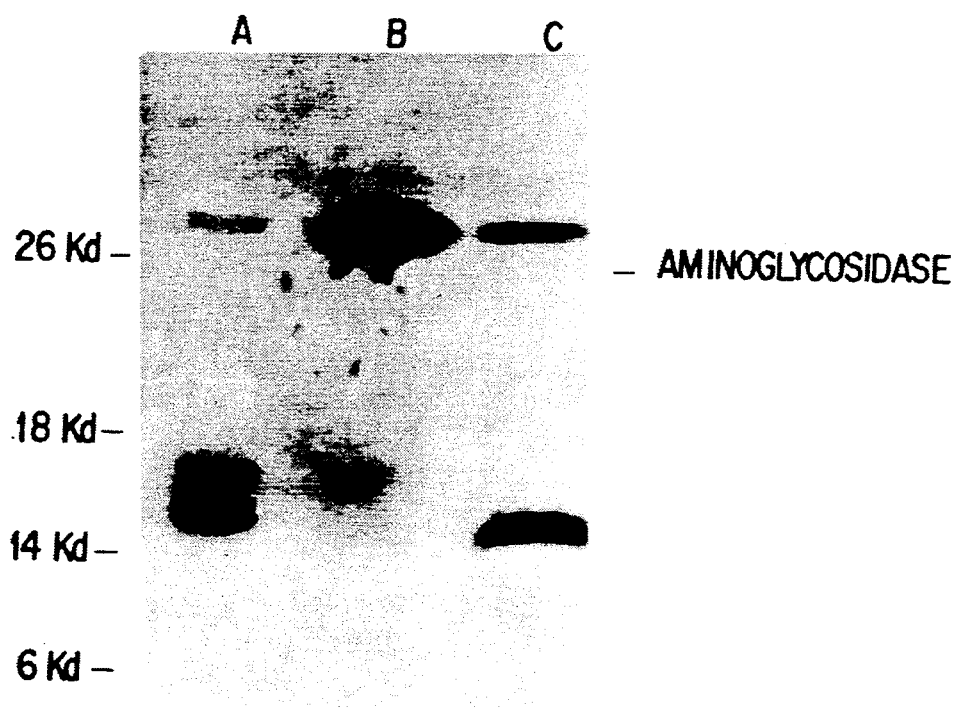

The Sau3A insert in pAA152 was found to have regenerated the BamHI site of the polylinker region at one end of the insert. Deletions from this BamHI site to either the unique BglII site or the unique XbaI site of the Hi DNA resulted in loss of expression of the PBOMP detected on Western blots. Deletions from the HincII site of the polylinker to either the XbaI or BglII sites of the Hi insert DNA retained PBOMP expression (FIG. 4). From these results, we conclude that the gene encoding this PBOMP lies in the BglII-BamHI 737 base pair fragment within the Hi DNA insert of pAA152. Analysis of minicells (Achtman et al., 1979, Proc. Nat'l Acad. Sci. USA 76:4837–41) carrying pAA152 indicated that the cloned Hi DNA encodes two proteins of 16000 and 40,000 daltons molecular weight respectively (FIG. 6). Western blots of JM83 (pAA152) show that pooled monoclonal antibodies raised against PBOMP-1 react with a 16000 dalton protein. No cross reaction is apparent within the 40,000 dalton molecular weight region.

6.6.2 Isolation of a PBOMP Gene Encoding a Protein which Reacts with Polyclonal Anti-PBOMP-1 Antisera The amplified phage library prepared as described in section 6.5.1. was diluted to 1–2000 PFU in one ml TMG and 50 ul of E. coli KH802 ($5 \times 10^9$ cells/ml) were added. The mixture was incubated at 37° C. for 20 minutes and plated with 3 ml soft agar on agar plates containing NZYCM medium: 10 g NZ Amine A, 5.0 g NaCl, 2.0 g $MgSO_4.7H_2O$, 5 g Yeast Extract, 1 g casamino acids (per liter). Plates were incubated overnight, chilled to 4° C. for 30–60 minutes, and plaques were transferred to nitrocellulose. Filters were probed with polyclonal anti-PBOMP-1 as described above in Section 6.4.4. Several positive plaques were detected in this manner. However, no positive plaques were detected when PBOMP-1 monoclonal antibodies were used as a probe. Positive plaques were picked from the plate and amplified by growth in E. coli KH802. Clones were verified by SDS-PAGE gel/Western Blot analysis of phage lysates. All positive clones expressed a protein of apparent molecular weight 16000 daltons which reacted with polyclonal antibody to PBOMP-1. This protein was not present in control lysates of Charon 4 phage. In similar experiments, lysates from the positive clones failed to react with monoclonal antibodies to PBOMP-1.

One positive phage, designated lambda 16-3 was selected for further analysis. This phage isolate was amplified by growth in E. coli KH802 in NZYCM broth, recovered by precipitation with 20% Polyethylene glycol 6000 and banded in cesium chloride equilibrium gradients (4M CsCl in TMG, Beckman SW50.1 rotor, 300,000×g for 24 hours). Phage DNA was isolated by treatment with 0.1% SDS and 20 ug/ml proteinase K (Sigma Chemical Co., St. Louis, Mo.) at 55° C. for 1 hour followed by extraction with phenol and ethanol precipitation.

Figure 7A:
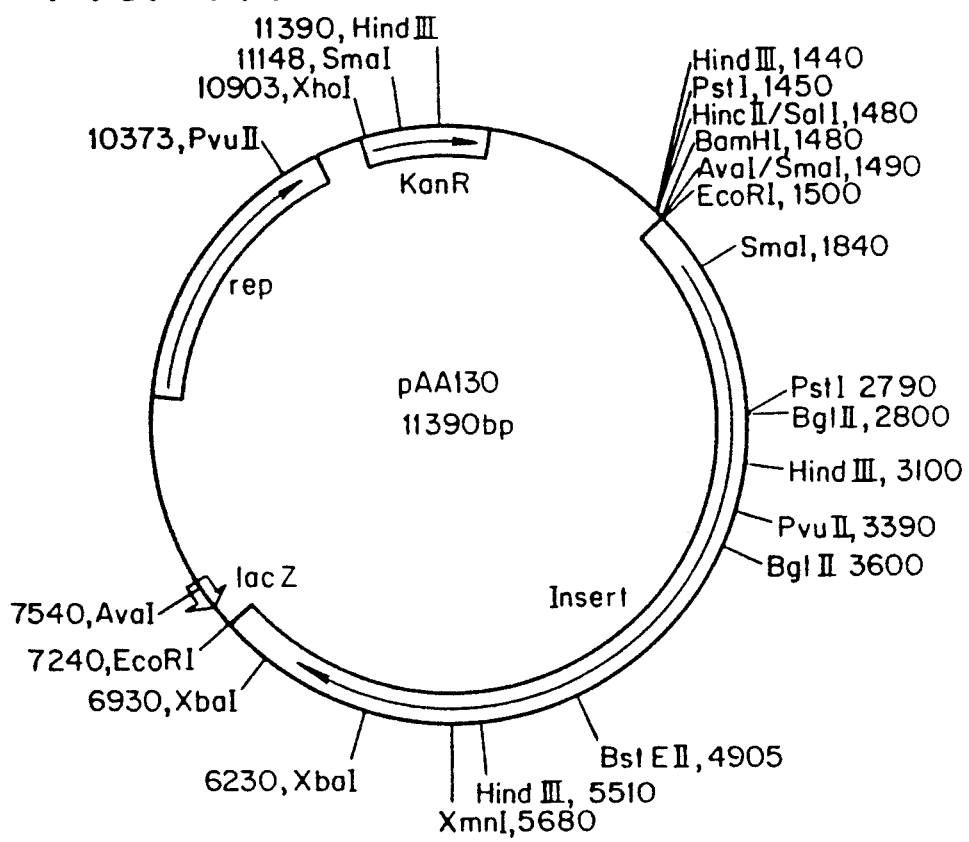
Figure 7B:
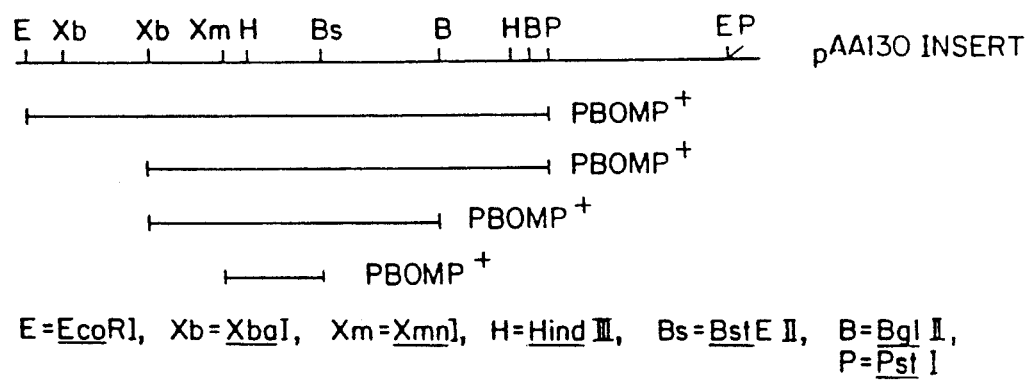

The lambda 16-3 DNA was digested with EcoRI and a partial physical map of the Hi chromosomal insert was obtained. EcoRI fragments of the insert were isolated and subcloned into plasmid vector pGD103. Clones carrying fragments expressing the PBOMP-1 cross-reactive 16000 dalton protein were identified by Western blot transfer analysis of cell lysates. One of these was designated pAA130. FIG. 7 represents a restriction map of this plasmid having an 5.7 Kb fragment from Hi DNA cloned into pGD103 plasmid.

Figure 8:
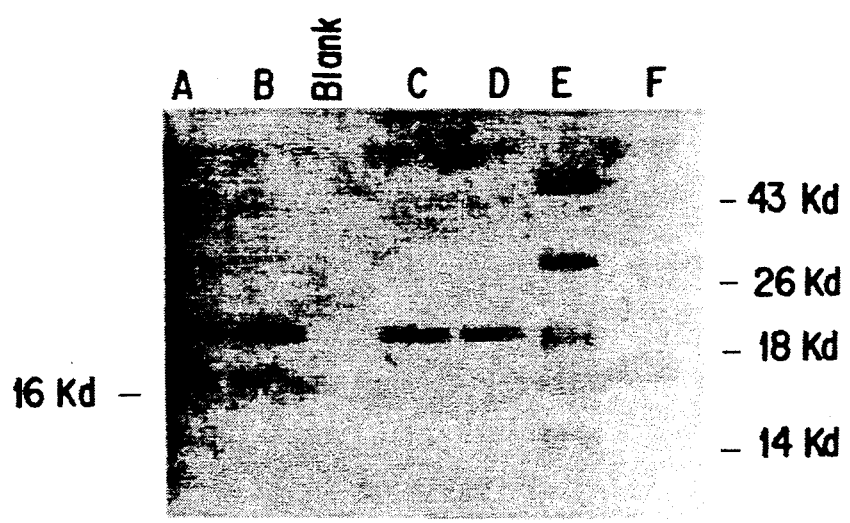
FIG. 8 represents reactivity of whole cell lysates of *E. coli* JM83 and *E. coli* JM83 containing pAA130 with polyclonal anti-PBOMP-1 antiserum. Lanes represent: (A) JM83 containing pAA130; (B) JM83 containing pAA130; (C) JM83; (D) JM83; (E) molecular weight standards as displayed in kilodaltons on the right side of the FIG.; and (F) Hi S-2.

Monoclonal antibodies against PBOMP-1 did not react with the 16000 dalton protein expressed from pAA130 (data not shown). The protein expressed by this recombinant plasmid was recognized, however, by polyclonal anti-PBOMP-1 antisera (see FIG. 8 for example).

Analysis of minicells (Achtman et al., supra) carrying pAA130 indicated that the cloned Hib DNA codes for proteins of apparent molecular weights of 16,000 and 17,000 daltons. The labelled 16,000 dalton protein was specifically immunoprecipitated by polyclonal anti-PBOMP-1 (data not shown). Thus, plasmid pAA130 directs the expression of a 16000 dalton molecular weight PBOMP.

An internal deletion generated by excision of DNA inserted between the unique PstI site of the insert and the single PstI in the polylinker did not affect the expression of the cross-reacting protein. The XbaI fragment of this plasmid was deleted by a similar method and expression of the PBOMP-cross reacting protein was retained (FIG. 7). An additional deletion derivative of this plasmid was generated by religation of the two internal BglII sites and this derivative also retained expression of the PBOMP-cross reactive protein.

The 781 base pair BstEII-XmnI fragment was cloned by isolating the fragment from a low melting point agarose gel, filling in the BstEII end with Klenow fragment of DNA Polymerase I and cloning the fragment into the HincII site of pGD103. Western blot analysis using polyclonal anti-PBOMP-1 showed that this plasmid retained expression of the 16,000 dalton PBOMP. As with pAA130, the PBOMP produced from this plasmid failed to react with monoclonal antibodies to PBOMP-1.

As an independent method of verifying the location of this PBOMP gene, the large EcoRI-PvuII fragment of pAA130 was ligated with the EcoRI-PvuII fragment of pLG339 to generate a new tetracycline resistant plasmid designated pAA136. This plasmid expressed the PBOMP as verified by Western blots. This plasmid was transformed into an *E. coli* strain with deletion of the chromosomal alkaline phosphatase gene (phoA) and carrying the transposible element TnPhoA. Three independent transpositions of the TnPhoA element into pAA136 which restored alkaline phosphatase activity were isolated. The sites of the TnPhoA insertions into pAA136 were determined using the unique DraI restriction site near the left terminal region of TnPhoA and the HindIII, BstEII, XmnI, and PstI sites of pAA136. All three insertions were determined to fall within the BstEII-XmnI fragment of pAA136. All three TnPho insertions were in the same orientation indicating that transcription of the PBOMP gene is directed from the BstEII site towards the XmnI site in pAA136. All three TnPhoA transpositions resulted in loss of the 16,000 protein detected by polyclonal anti-PBOMP-1 antiserum as detected by Western blots. One fusion generated a new band on Western blots at 60,000 dalton which was detected by polyclonal anti-PBOMP-1 antiserum. This size is within the predicted range of fusion proteins that might be generated by fusion of alkaline phosphatase (45000 daltons MW) to a 16,000 dalton MW protein. Restoration of PhoA activity in these transpositions verifies that the PBOMP protein contains a peptide signal for membrane transport; and hence, is probably a membrane protein.

The TnPho fusions were sequenced by subcloning the junction between TnPhoA and the Hi cloned DNA sequences into M13. In all cases the PhoA coding sequences were determined to be in frame with the predicted open reading frame for the PBOMP-2 gene of pAA130 (see Section 6.7.2, infra).

6.7 Determination of the Nucleotide Sequence of PBOMP Genes

6.7.1 Sequencing Strategy for the PBOMP Gene Expressed by pAA152

The nucleotide sequence of the PBOMP gene expressed by pAA152 was obtained by dideoxynucleotide sequencing (Sanger et al., 1978, Proc. Nat'l Acad. Sci USA 74:5463-5467) of the 737 bp BglII-BamHI fragment of pAA152, after subcloning into single stranded phages of the M13 family, i.e., M13 mp18 and mp19.

Figure 9:
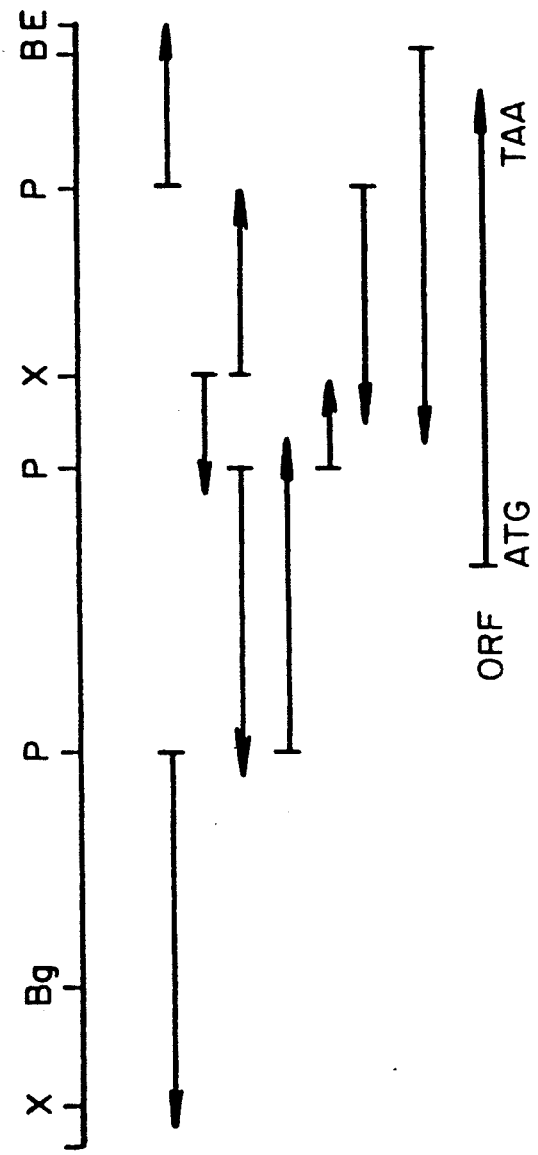
FIG. 9 represents the DNA sequencing strategy of the 737 bp insert fragment of pAA152 showing the origin, direction, and extent of sequence determined from the various clones. The arrow at the bottom denotes the location of the major open reading frame (ORF).

The location and direction of sequences determined from these subclones is shown in FIG. 9. The complete nucleotide sequence of the BglII-BamHI fragment is shown in FIG. 10.

The 737 BglII-BamHI fragment of pAA152 contains a single open reading frame (ORF) coding for a polypeptide of 153 amino acids (FIG. 11). The amino acid composition of the PBOMP gene determined from the DNA sequence closely matches the amino acid composition of the PBOMP-1 purified protein (see Tables 1 and 2).

TABLE 2

| DEDUCED AMINO ACID COMPOSITIONS OF MATURE PBOMP-1 AND PBOMP-2 | | |
|---|---|---|
| Amino Acid Residues | Mature PBOMP-1 of pAA152[a] | Mature PBOMP-2 of pAA130[b] |
| Aspartic Acid | 9 | 6 |
| Asparagine | 8 | 4 |
| Threonine | 7 | 5 |
| Serine | 6 | 13 |
| Glutamic Acid | 7 | 5 |
| Glutamine | 5 | 7 |
| Proline | 3 | 1 |
| Glycine | 16 | 24 |
| Alanine | 21 | 16 |
| Cysteine | 1 | 1 |
| Valine | 10 | 18 |
| Methionine | 0 | 1 |
| Isoleucine | 3 | 13 |
| Leucine | 9 | 5 |
| Tyrosine | 11 | 2 |
| Phenylalanine | 3 | 2 |
| Lysine | 7 | 7 |
| Histidine | 2 | 0 |
| Arginine | 6 | 6 |
| Tryptophan | 0 | 0 |

[a] The apparent molecular weight of mature PBOMP-1 was 14,238 daltons. The number of amino acid residues was 134.
[b] The apparent molecular weight of mature PBOMP-2 was 13,461. The number of amino acid residues was 136.

In addition, the PBOMP-1 gene has an internal peptide sequence (AA 48-81) in which 30/33 amino acids align with the amino acid sequence of the T9 internal peptide of PBOMP-1 if an allowance is made for the Leu-68 residue which is absent from the sequence of the T9 peptide (FIG. 12). The amino terminal region of PBOMP-1 also contains an amino acid sequence which shows similarities with other membrane transport peptide sequences (Watson, 1984, Nucleic Acids Res. 12:5145–5164). From these data and from the monoclonal antibody binding data, we conclude that this gene encodes the PBOMP-1 protein.

6.7.2 Sequencing Strategy for the PBOMP Gene of pAA130

The nucleotide sequence of the PBOMP gene of pAA130 was determined by dideoxynucleotide sequencing (Sanger, et al., supra) of the 789 base pair BstEII-XmnI fragment of pAA130 after subcloning into M13 mp18 and mp19 phage. These recombinant phage are designated M18001 and M19001 respectively. The universal 17 base oligonucleotide sequencing primer (New England Biolabs) was used to determine the sequence from both ends of the BstEII-XmnI fragment (see FIG. 13). Two additional oligonucleotides were synthesized and used as primers for dideoxynucleotide sequencing (M18PRI, M19PR2). All other sequencing primers were made at Praxis Biologics, Rochester, N.Y. on an Applied Biosystems 380 B DNA synthesizer. The primers were made on a 1 umole controlled pore glass column with beta-cyanoethyl phosphate protecting group chemistry. The yield of oligonucleotide was sufficiently pure to allow the use of the primers directly from the column without further purification. The two synthetic oligonucleotide primers bind to sequences approximately 200 nucleotides in from each end of the fragment as shown in FIG. 13. The total 789 bp DNA sequence of the BstEII-XmnI fragment of pAA130 is shown in FIG. 14. The ORF is underlined as shown in FIG. 15. Thus ORF encodes a polypeptide of 154 amino acids. The amino terminal 18 residue peptide resembles a membrane transport signal sequence determined for other proteins (Watson, 1984, supra). In addition, sequence data from the TnPhoA fusions in pAA130 demonstrated that all three transpositions were into the reading frame of the 154 amino acid polypeptide.

The amino acid composition of the proposed mature gene product as deduced from the DNA sequence of the ORF of pAA130 differs significantly from that determined by amino acid analysis of purified PBOMP-1 (Tables 1 and 2). No significant homology was found when the amino acid sequence of the PBOMP gene of pAA130 was compared to that of the tryptic peptide T9 from purified PBOMP-1 protein. In addition, although the product encoded by this gene is recognized by polyclonal anti-PBOMP-1 antisera, it is not recognized by monoclonal antibodies to PBOMP-1. From these observations, it is clear that the Hi gene expressed by pAA130 is not the gene for PBOMP-1. Thus the PBOMP-gene encoded by pAA130 was designated PBOMP-2.

6.8. Characterization of PBOMPs Expressed by Recombinant E. coli as Lipoproteins As demonstrated in Section 6.1.2., PBOMP-1 isolated from H. influenzae has covalently attached fatty acids, including lauric acid, palmitic acid and a derivative of palmitic acid, and hence can be classified as a bacterial lipoprotein. The following experiments were performed to investigate whether PBOMPs expressed by recombinant E. coli also exist as lipoproteins. Two different in vivo methods were used to verify the lipoprotein nature of the expressed PBOMPs.

In one series of experiments, cells containing recombinant plasmids expressing PBOMPs were cultured in the presence of a radioactively labelled fatty acid. Under such conditions, any lipoprotein formed containing the covalently attached fatty acid will be specifically radiolabeled.

E. coli JM83 cells containing either plasmid pAA152 expressing PBOMP-1 or plasmid pAA130 expressing PBOMP-2 were grown for 2 hours in M9-minimal medium containing 50 uCi/ml $^{14}$C-palmitic acid. Whole cell lysates (10,000 trichloroacetic acid precipitable cpm/lane) were electrophoresed on 15% SDS-PAGE gels at 35 mA constant current. The gels were impregnated with sodium salicylate ($5 \times$ gel volume $\times$ 1M solution for 20 minutes), dried, and exposed at $-70°$ C. on XAR-5 film (Eastman Kodak Company, Rochester, N.Y.). Whole cell lysates of normal E. coli JM83 cells similarly cultured were run as controls. Results obtained are illustrated in FIG. 17.

As demonstrated in FIG. 17, a radiolabeled protein of about 15,000 daltons was observed in lysates of E. coli containing pAA152 and pAA130 which was not observed in lysates of control E. coli cells. Thus, the PBOMP-1 and the PBOMP-2 expressed by the recombinant E. coli were specifically radiolabeled.

In another series of experiments, cells containing recombinant plasmids expressing PBOMPs were cultured in the presence of globomycin, an antibiotic known to specifically block processing of all known bacterial lipoproteins by inhibition of the liproprotein signal peptidase (Inukai et al., 1978, J. Antibiotics (Tokyo) 31:1203–1205).

E. coli JM83 cells containing either pAA152 or pAA130 were cultured in the presence of 25 ug/ml globomycin (obtained from Dr. M. Inouye, Robert Woods Johnson Medical Dental School, Piscataway, N.J.) for 1 hour. Similar cultures untreated with globomycin served as controls. Whole cell lysates were electrophoresed on 15% SDS-PAGE gels, transferred to nitrocellulose, and probed with polyclonal anti-PBOMP-1 antisera. Results obtained are illustrated in FIG. 18.

As demonstrated in FIG. 18, in lysates of globmycin-treated cells expressing either PBOMP-1 or PBOMP-2, an approximately 16,500 dalton band was observed which was not detected in lysates of control or untreated cells.

Based on results obtained in both series of in vivo experiments, the PBOMP-1 and PBOMP-2 proteins expressed by recombinant E. coli containing PBOMP genes are lipoproteins.

7 EFFICACY OF PBOMP-1 AND PBOMP-2 SUBUNIT VACCINES

7.1 Bactericidal Activity of Anti-sera Induced by PBOMP-1 and PBOMP-2

Anti-PBOMP-1 polyclonal rabbit antisera, prepared as described in Section 6.2., were examined for their ability to kill Hib and Hi in an in vitro complement mediated bactericidal assay system (see Musher et al., 1983, Infect. Immun. 39:297–304; Anderson et al., 1972, J. Clin. Invest. 51:31–38). Sources of complement used for the assay system were either pre-collostral calf serum (PCCS) or normal rabbit serum (NRS) which had been absorbed previously with a non-typable Hi strain, S2, to remove any pre-existing anti-Haemophilus antibodies. The PCCS was used undiluted and the NRS was used at a dilution of 1:4 for Hib and 1:8 for non-typable Hi. All dilutions were prepared using phosphate-buffered saline [20 mM phosphate buffer (pH 7.4), 0.15M NaCl containing 0.15 mM $MgCl_2$ and 0.5 mM $CaCl_2$ (PCM)]. Bacterial strains to be tested were grown in BHI-XV until they reached a concentration of $1 \times 10^9$ cells/ml as measured by optical density at 490 mm. Bacteria were diluted to a final concentration of 1250 cells/20 ul in PCM. Twenty microliters of an appropriate antibody dilution in PCM was mixed with 20 ul of complement source on ice in wells of a 24 well microtiter plate (Costar). The microtiter plate was removed from ice and 20 ul of test diluted bacteria were added to each well. Wells containing no antibody served as negative controls. After 30 minutes incubation at 37° C., 800 ul of BHI-XV, containing 0.75% agar at 56° C., were added to each well and allowed to solidify at room temperature. The plates were incubated overnight at 37° C. and read the next day.

The BC titer of an antisera was read as the reciprocal of the highest dilution capable of killing 50% of the test bacteria as compared to non-antibody control wells.

The anti-PBOMP-1 was tested for bactericidal (BC) activity against several Hib clinical and laboratory isolates and the results shown in Table 3.

TABLE 3

BC ACTIVITY OF ANTI-PBOMP-1 ANTISERA AGAINST LABORATORY & CLINICAL STRAINS OF HAEMOPHILUS INFLUENZAE

| | KILLED BY ANTI-PBOMP-1 |
|---|---|
| LABORATORY STRAINS | |
| H. influenzae type a HST-1 | +[a] |
| H. influenzae type c HST-5 | +/−[b] |
| H. influenzae type b HST-3 | + |
| H. influenzae type b HST-10 | + |
| H. influenzae type b HST-12 | + |
| N.T. H. influenzae S-2 | + |
| N.T. CLINICAL STRAINS | |
| N.T. H. influenzae HST-31 | + |
| N.T. H. influenzae HST-35 | + |
| HIB CLINICAL STRAINS | 112 strains killed |
| 112 strains tested | |

[a] + = greater than 50% killing of test bacteria
[b] +/− = approximately 50% of test bacteria survived As can be seen from Table 3, anti-PBOMP-1 antibody had BC activity against a wide variety of clinical isolates both typable (e.g. a, b, c) and non-typable H. influenzae strains. One hundred and twelve out of 112 Hib clinical isolates were killed by anti-PBOMP-1 antisera. These strains were isolated in the Southwestern U.S., the Northeastern U.S. and Western Canada.

In order to eliminate the possibility that the killing was the result of anti-LPS antibody, the BC assay was performed with 200 ng of LPS from the Hib strain used to prepare the immunogen in each well. Results of these experiments are shown in Table 4.

TABLE 4

BACTERICIDAL ACTIVITY OF ANTISERA ABSORBED WITH LPS

| ANTISERUM | LPS[a] | TEST BACTERIA | TITER[b] |
|---|---|---|---|
| PBOMP-1 | + | N.T. H. influenzae | 40 |
| | − | N.T. H. influenzae | 160 |
| | + | Hib Eagan | 40 |
| | − | Hib Eagan | 40 |
| PRP-CRM | + | N.T. H. influenzae | 10 |
| | − | N.T. H. influenzae | 10 |
| | + | Hib Eagan | 400 |

TABLE 4-continued

BACTERICIDAL ACTIVITY OF ANTISERA ABSORBED WITH LPS

| ANTISERUM | LPS[a] | TEST BACTERIA | TITER[b] |
|---|---|---|---|
| | − | Hib Eagan | 800 |

[a] ZERO or 200 ng Hib Eagan LPS used per well
[b] Expressed as reciprocal of highest dilution of antisera showing 50% bacterial survival The LPS lowered the titer of the anti-PRP two-fold, the titer of the anti-PBOMP-1 against Hi four-fold and the titer of anti-PBOMP-1 against Hib not at all. While the LPS reduced the BC activity of anti-PBOMP-1, it did not eliminate it. Some of the observed reduction was undoubtably the result of anti-complementary activity of the LPS, as demonstrated by the reduction of the anti-PRP BC titer.

The anti-PBOMP-2 antibody prepared as described in Section 6.2, was tested for bactericidal (BC) activity against the Haemophilus Influenzae S2 strain and the results are shown in Table 5. Sera was collected prior to inoculation and 7 and 10 weeks after initial immunization. As shown below, the BC activity of anti-PBOMP-2 antisera was found to increase significantly 7 weeks after inoculation. No further increase was observed 10 weeks after inoculation.

TABLE 5

BC ACTIVITY OF ANTI-PBOMP-2 ANTISERA AGAINST THE S2 STRAIN OF HAEMOPHILUS INFLUENZAE

| SERUM FROM WEEK | BACTERICIDAL TITER | FOLD INCREASE IN TITER |
|---|---|---|
| 0 | 1/20 | — |
| 7 | 1/160 | 8× |
| 10 | 1/160 | 8× |

7.2 Infant Rat Protection from H. influenzae

Infant rat protection studies were performed according to Smith et. al. (1973, Infec. Immun. 8: 278–90. Sprague-Dawley infant rats were passively immunized with 0.1 ml of varying dilutions of rabbit antisera in PCM by intraperitoneal inoculation on day four of life. Eighteen hours post-immunization, the rats were challenged intraperitoneally with $10^4$–$10^6$ Hib cells in 0.1 ml of PCM. Survival of challenged rats at 72 hours post-infection indicated protection. Results of these experiments are shown in Table 6.

TABLE 6

INFANT RAT PROTECTION BY ANTI-PBOMP-1

| Hib Challenge Strain | Antiserum Passively Transferred | Antiserum Dilution | Challenge Dose | Survivors/ Total |
|---|---|---|---|---|
| HST-60 | NRS | 1/10 | $10^6$ | 0/6 |
| | PBOMP-1 | 1/10 | $10^6$ | 5/5 |
| | PBOMP-1 | 1/30 | $10^6$ | 6/6 |
| | PBOMP-1 | 1/90 | $10^6$ | 6/6 |
| HST-61 | NRS | 1/10 | $10^5$ | 0/5 |
| | PBOMP-1 | 1/10 | $10^5$ | 6/6 |
| | PBOMP-1 | 1/30 | $10^5$ | 6/6 |
| | PBOMP-1 | 1/90 | $10^5$ | 3/5 |
| Eagan | NRS | 1/10 | $10^4$ | 0/4 |
| | PBOMP-1 | 1/10 | $10^4$ | 3/5 |
| | PBOMP-1 | 1/30 | $10^4$ | 5/5 |
| | PBOMP-1 | 1/90 | $10^4$ | 0/5 |

The results in Table 6 indicate that infant rats are protected against challenge with a fatal dose of Hib by passively transferred anti-PBOMP-1 antibody. The additional clinical Hib strains which were used as challenge strains in the infant rat meningitis model to demonstrate protection that anti-PBOMP-1 protects against heterologous Hib clinical isolates.

To determine whether anti-PBOMP-1 blocks the protective effects of anti-PRP or has additive effects, infant rats were passively immunized with anti-PRP and anti-PBOMP-1 diluted beyond their protective end points. Upon challenge with Hib, the antisera together were able to protect high dilutions than either one above (Table 7). These results shown in Table 7 indicate that anti-PBOMP-1 antibody and anti-PRP antibody do not interfere with each other and are capable of giving additive protection the infant rat meningitis model.

TABLE 7

| ANTI-PBOMP-1 + ANTI-PRP INFANT STUDIES SERA INJECTED | | |
|---|---|---|
| ANTI-PBOMP-1 (1:100)[a] | ANTI-PRP[b] | SURVIVORS/TOTAL[c] |
| — | — | 0/6 |
| + | — | 1/6 |
| — | 1:2000 | 2/6 |
| + | 1:1000 | 6/6 |
| + | 1:3000 | 5/6 |
| + | 1:4000 | 4/6 |

[a]Polyclonal rabbit anti PBOMP-1 diluted in PCM.
[b]Polyclonal rabbit anti-PRP:CRM$_{197}$ conjugate.
[c]Infant Sprague-Dawley rats surviving at 72 hours post-challenge.

7.3 Immunogenicity of PBOMP-1 in Human Adults

Six human adult volunteers received two vaccinations with vaccine formulations comprising PBOMP-1 isolated from *H. influenzae* as described in Section 6.1., (5.2 ug PBOMP-1 without alum) at one month intervals, except for one individual who received only a single vaccination. Blood samples were obtained just prior to the initial vaccination and at monthly intervals thereafter. The specific antibody response of vaccinated adults was evaluated by measurement of antibody titers to *H. influenzae* PBOMP (ELISA), to diphtheria toxoid (ELISA) (see, Engvall et al., 1972, J. Immunol. 109:129-135 for general description of ELISA assays) and to Hib PRP polysaccharide (Farr-type RIA) (see, Farr, 1958, J. Infect. Dis. 103:239-262 for description of Farr-type RIA). Results obtained in the PBOMP-1 ELISA assay are illustrated in FIG. 19.

As demonstrated in FIG. 19, three of the six individuals showed a significant rise in antibody titer to PBOMP-1. This rise in antibody titer was highly specific to the PBOMP-1 employed as an immunogen as no significant change was observed in the titer of antibody specific to either diptheria toxoid or Hib PRP (results not shown).

7.4 Bactericidal Activity of Antisera Induced by Signal-less PBOMP-1

A recombinant signal-less PBOMP-1 (herein designated rPBOMP-1) obtained from *E. coli* PR13 cells containing plasmid pPX167 as described infra in Section 8.1 was used as an immunogen to immunize white New Zealand rabbits. The rPBOMP-1 was either emulsified in incomplete Freund's adjuvant (IFA) or bound to aluminum hydroxide. rPBOMP-1 was bound to alum by mixing rPBOMP-1 at a concentration of 500 ug/ml in 0.85% saline with alum at a concentration of 500 ug/ml at a 1:1 ratio. The mixture was shaken at 37° C. for 3 hours and the alum pelleted by centrifugation. Supernatent was assayed by BCA protein assay (Pierce Chem. Co., Chicago, Ill.) for unbound protein. None was detected. Alum was resuspended in physiological saline at 500 ug/ml. rPBOMP-1 was emulsified in IFA (Difco) in a 1:1 ratio. Animals were immunized intramuscularly with 50 ug of either preparation at 4 week intervals. Animals were bled at weeks 0, 6, and before each immunization.

The anti-rPBOMP-1 polyclonal rabbit antisera obtained were examined for the ability to kill Hi in an in vitro complement mediated bactericidal assay system as described supra in Section 7.1. Antisera were tested from just prior to the first immunization, week 0, and two weeks after a second immunization, week 6. The bactericidal (BC) activity of the antisera were compared with that of antisera made against PBOMP-1 isolated from *H. influenzae* (designated "native PBOMP-1"). The test bacterium was nontypable *H. influenzae* strain S-2. Results are shown in Table 8.

TABLE 8

| BC ACTIVITY OF ANTISERA AGAINST rPBOMP-1[a] | | | |
|---|---|---|---|
| | Antiserum Against | | |
| Antiserum[b] | Native PBOMP-1 | rPBOMP-1 (IFA) | rPBOMP-1 (Alum) |
| Week 0 | 1:5 | 1:5 | 1:10 |
| Week 6 | NT | 1:160 | 1:80 |
| Hyperimmune[c] | 1:160 | NT | NT |

[a]Test organism: nontypable *H. influenzae* S-2.
[b]For text for details of immunizations employed to obtain antisera
[c]Hyperimmune antiserum was made against multiple doses of native PBOMP-1.

The BC titer of an antisera was read as the reciprocal of the highest dilution capable of killing 50% of the test bacteria as compared to non-antibody control wells.

While both rabbits had low levels of BC activity prior to immunization, titers of 1:5 and 1:10, the BC of the sera obtained at week 6 had significant increases in BC activity. The rabbit immunized with rPBOMP-1 in IFA had a titer of 1:160 and the rabbit immunized with rPBOMP-1 on alum had a titer of 1:80. Hyperimmune antiserum was obtained after the rabbit received multiple doses of native PBOMP-1. The hyperimmune rabbit anti-PBOMP-1 serum had a titer of 1:160. These results clearly indicate that the rPBOMP-I is capable of eliciting antibody which recognizes the native PBOMP-1 in Haemophilus and is biologically active in the bactericidal assay system.

8 NOVEL PLASMIDS FOR ENHANCED EXPRESSION OF PBOMPs IN *E. coli*

8.1 Enhanced Expression of PBOMP-1 in *E. coli*

The PBOMP-1 protein is expressed from the 737 bp BamHI-BglII fragment of pAA152, presumably under control of its native promoter. The sequence contains a good consensus ribosome binding site and initiation codon of the PBOMP-1 gene. While PBOMP-1 expressed in *E. coli* with plasmids containing this fragment was easily detected by Western blot analysis, the amount of such protein produced was less than 1% of cell protein, i.e., less than the amount of PBOMP-1 made in *H. influenzae* cells containing the native gene.

As an initial attempt to produce higher levels of PBOMP-1 in *E. coli*, the cloned gene was placed under the control of promoters lac and lambda PL known to yield high protein production. Promoters were linked to the BstNI site upstream of the PBOMP-1 initiation codon (FIG. 4A). Cleavage at this site removes the native PBOMP-1 promoter but leaves the ribosome binding site intact.

These constructions were carried out as follows. First, the 739 bp BamHI-BglII fragment of pAA152 carrying the PBOMP-1 gene was cloned into the BamHI site of lac promoter of plasmid pUC19. One clone carrying the PBOMP-1 gene in the same orientation as the lac promoter was designated pPX160. Expression of PBOMP-1 from pPX160 in E. coli JM103 was under regulation of the native promoter not under lac regulation; apparently due to a transcription termination signal in the 240 bp between the BglII site and the translation initiation codon of PBOMP-1. Plasmid pPX160 was then cleaved with BstNI, which cleaves between the PBOMP-1 initiation codon and the consensus translation initiation site of the gene, but leaves the ribosome binding site attached to the coding region. The ends were filled in with E. coli DNA polymerase I (Klenow fragment), and the linearized plasmid was cleaved with BamHI. The 577 bp BstNI-BglII fragment carrying the promotorless PBOMP-1 gene was ligated to pUC19 cleaved with HincII and BamHI. The resulting plasmid designated pPX166 was found by Western blot to express PBOMP-1 under regulation of the lac promoter in E. coli JM103.

When PBOMP-1 was expressed from lac or $P_L$ promoters in E. coli JM103 or HB101 strain, only low levels of PBOMP-1 were expressed. Western blot analysis of lysates from these cells with monoclonal antibody G-204, which binds to the amino terminal 20 amino acids of mature PBOMP-1, demonstrated the presence of a 4000-5000 dalton peptide recognized by this monoclonal antibody (FIG. 20). In cells expressing PBOMP-1 under regulation of the induced PL promoter, greater than 90% of the G-204 binding activity was in this presumed breakdown product, indicating PBOMP-1 expressed at high levels in E. coli is unstable.

Plasmids pPX160 and pPX166 were transformed into several E. coli strains containing mutations reported to stabilize foreign proteins. These include ATP-dependent protease (lon⁻) mutations, heat shock response (htp), and an mRNA-stabilizing mutation (pnp). In addition, since processing of PBOMP-1 as a lipoprotein may enhance its stability, the plasmids were placed in an E. coli strain lacking the major native E. coli lipoprotein, the murein lipoprotein (lpp⁻). In all strains testes, the PBOMP-1 breakdown product recognized by monoclonal antibody G-204 was present at about the same level. Hence, it appears that breakdown of PBOMP-1 in E. coli is due to some other unidentified activity.

As a second approach, a modified PBOMP-1 gene was created by removing the native signal sequence of the gene. Such a construction offers two potential advantages over native PBOMP-1 protein. First, the signal-less PBOMP-1 may not be transported to the membrane, and hence, toxicity effects due to overexpression of PBOMP-1 may be lessened. Second, since it is not modified with the extremely hydrophobic lipid groups, signal-less PBOMP-1 may not require use of detergents for isolation or storage in solution.

Construction of a signal-less form of PBOMP-1 is illustrated in FIG. 21. As shown in FIG. 21, the PBOMP-1 gene from plasmid pPX160 was cleaved at codon 19 with AluI restriction endonuclease. The resulting fragment was ligated to the SmaI restriction site within the pUC19 polylinker region. The resulting gene expressed a hybrid protein containing all of the amino acids sequence of native PBOMP-1 plus an additional 18 amino acids from the pUC19 polylinker region at the amino terminus. This plasmid was designated pPPX167.

As shown further in FIG. 21, a second recombinant plasmid espressing PBOMP-1 was derived from plasmid pPX167 by cleaving at the BamHI site in the polylinker and cloning the fragment into the BamHI site of plasmid pINIII-ompA3. The resulting plasmid pPX168 contains a hybrid gene which encodes mature PBOMP-1 linked at the amino terminus to the signal sequence of E. coli OMP A protein. This hybrid product is processed through the membrane via the OMP A signal sequence to generate a mature PBOMP-1 lacking lipoprotein modification and containing eight additional amino acids at its amino terminus.

Plasmids pPX167 and pPX168 were transformed into E. coli JM103 and tested for recombinant PBOMP-1 synthesis. By SDS-PAGE Western blot analysis, both plasmids were shown to encode proteins which were recognized by polyclonal and monoclonal anti-PBOMP-1 antisera. The modified PBOMP-1 synthesized from pPX167 was inducible with isopropylthio-beta-d-galactopyranoside (IPTG), was located in the cell cytoplasm, and was soluble in the absence of detergents. The modified PBOMP-1 was not detectable by Coomassie blue staining of whole cell lysates from IPTG-induced cells; and comprised less than 1% of total cell protein. The modified PBOMP-1 synthesized from pPX168 was also inducible with IPTG (under control of the hybrid lilac promoter), was excreted into the medium, and was also soluble in the absence of detergents. When fully induced, this modified PBOMP-1 was produced at a level of approximately 1 to 2 mg of cells.

Plasmids pPX167 and pPX168 were also tested in a variety of E. coli strains for levels of expression. The most successful combination tested was the pPX167 chimeric plasmid transformed into E. coli PR13, a strain containing the mRNA stabilizing mutation pnp. In this strain, recombinant PBOMP-1 is expressed under control of the lac promoter at about 2-3% of total cell protein after lac induction. This recombinant PBOMP-1 is expressed as a cytoplasmic fusion protein containing about 17 amino acids from the lac alpha-peptide and multiple cloning sequence fused to the amino terminus of the PBOMP-1 gene.

8.1.1 Purification and Characterization of Signal-less PBOMP-1

The following experiments were performed to purify and characterize the signal-less PBOMP-1 (designated herein rPBOMP-1).

Isolation of cytoplasmic extract. Cells from overnight cultures of E. coli PR13 containing pPX167 grown in Luria broth at 37° C. were pelleted at 4° C. in a GSA roter at 8,000 rpm for 10 minutes. Pellets were washed in 1/10 volume of 10 mM Tris-HCl, pH 7.5 and resuspended in 1/100 volume of 10 mM Tris, pH 7.5 containing 10 ug/ml DNase and 10 ug/ml RNase. Cells were disrupted by either sonication at 40W for 10 minutes on ice or by three passages through a French pressure cell at 20,000 psi. Unbroken cells were removed by centrifugation at 10,000 rpm in an SS-34 rotor at 4° C. for 10 minutes. Total cell membranes were removed by centrifugation at 55,000 rpm in a 60Ti rotor for 30 minutes at 4° C. Membranes were discarded and the supernatant retained DEAE Fractionation of cytoplasmic extract. The supernatant was passed over an ion exchange DEAE- Biogel A (Biorad Laboratories, Richmond, Calif.) column equilibrated with 10 mM Tris, pH 7.5. Essentially all proteins were bound to the column under these conditions. Bound rPBOMP-1 and other proteins were eluted stepwise with 10 mM Tris, pH 7.5 containing 80 mM NaCl. All proteins eluted by this buffer were pooled and concentrated by precipitation with 60% saturated ammonium sulfate at 4° C. The pellet was collected by centrifugation and dissolved in 10 mM Tris, pH 7.5 followed by dialysis against the same buffer to remove any residual ammonium sulfate.

Reverse phase chromatography of rPBOMP-1. The rPBOMP-1 containing supernatant was run over a 4.6×15 mm C-4 reverse phase HPLC column after dilution into a buffer containing 0.1% trifluoroacetic acid (TFA) in dH$_2$O. The column was run at a flow rate of 2 ml/min using the same buffer. Most of the proteins bound to the column under these conditions. Bound rPBOMP-I was eluted as a single peak by 0 to 95% acetonitrile gradient in 0.1% TFA over 20 minutes. The large peak containing rPBOMP-1 (see FIG. 22, peak 1) was collected, and fractions pooled and concentrated by evaporation of the solvent. Dried rPBOMP-1 was redissolved in dH$_2$O.

SDS-PAGE was performed as described above herein, on the cytoplasmic extract, the DEAE eluate and the reverse phase eluate obtained from the *E. coli* PR13 cells containing plasmid pPX167. After electrophoresis, the gels were stained with Coomassie brilliant blue stain for about 2 hours. Western blot analysis using monoclonal antibody GD204 was also performed. Results obtained are illustrated in FIG. 23 A and B.

As shown in FIG. 23A, rPBOMP-1 is the major protein present in the cytoplasmic extract of cells of *E. coli* PR13 containing plasmid pPX167 when stained with Coomassie stain (FIG. 23A, lane 1). As estimated by Western blot reactivity, greater than 95% of the rPBOMP-1 is located in the cytoplasmic extract. Since no detergent was used in preparing the cytoplasmic extract, the results indicate that the rPBOMP-1 obtained from those cells is soluble in 10 mM Tris-Hcl, pH 7.5 without detergent. This represents a departure from the PBOMP-1 obtained from Hib cells as a lipoprotein.

Preliminary experiments using the cytoplasmic extract indicated that rPBOMP-1 obtained from *E. coli* PR13 cells containing pPX167 may exist in aqueous solutions as a complex either with itself or with other cytoplasmic proteins. When gel filtration chromatography using acrylamide-agarose polymers or Sephadex beads was performed using this rPBOMP-1, the rPBOMP-1 eluted at an apparent molecular mass of greater than 100,000 daltons (data not shown). Ion exchange chromatography using DEAE-Biogel A (Biorad Laboratories, Richmond, Calif.) showed that rPBOMP-1 did not elute as a single peak at a particular salt concentration. The rPBOMP-1 eluted over a range of NaCl concentrations from approximately 20 mM to 75 mM in 10 mM Tris, pH 7.5. While the eluted rPBOMP-1 was one of many eluted proteins in the 80 mM NaCl wash, a significant number of cytoplasmic proteins remained bound to the column at salt concentrations greater than 80 mM. Thus, DEAE chromatography as described above was used as a preliminary step to remove a significant number of contaminating proteins from the rPBOMP-1.

As shown in FIG. 23A DEAE chromatography greatly reduced the number of proteins found in the cytoplasmic material (FIG. 23A, lane 2) and did not alter the reactivity of rPBOMP-1 with monoclonal antibody (FIG. 23B, Lane 2).

The amino acid sequence of rPBOMP-1 indicates that it sould be a relatively hydrophobic protein. While it was soluble in the cytoplasmic extract without detergents, it was expected that the rPBOMP-1 would be more hydrophobic than most of the cytoplasmic proteins. The DEAE eluate containing the rPBOMP-1 was thus chromatographed on a C-4 hydrophobic interaction column as described above and eluted using a gradient of increasing acetonitrile. In this system, more hydrophobic proteins should be bound more tightly to the column and thus elute in higher concentrations of acetonitrile. It was thought that the rPBOMP-1 would bind more tightly than most of the contaminating proteins and elute after most of them. When the rPBOMP-1 containing fraction was chromatographed on a C-4 column, the PBOMP-1 was found to be the major peak eluted from the column (FIG. 21) and surprisingly it eluted first at the lowest concentration of acetonitrile.

As shown in FIG. 23A, lane 3, the rPBOMP-1 peak was pure as determined by Coomassie brilliant blue R-250 staining of 10 ug of protein after SDS-PAGE. The peak showed two bands, a major and a minor band, on Coomassie staining, both of which reacted with monoclonal antibody to PBOMP-1 which recognizes the amino terminal 20 amino acids of PBOMP-1 (FIG. 23B, lane 3). The minor band, approximately 2000 kilodaltons smaller than full size rPBOMP-1 was also present in whole cell extracts of PR13(pPX167) indicating that the smaller protein is not a by-product of the purification process. After concentration by evaporatin of the solvent, the purified rPBOMP-1 was soluble in aqueous solvents without detergent.

Immunization of rabbits. New Zealand white rabbits were immunized with rPBOMP-1 obtained from *E. coli* PR13 cells containing pPX167 either emulsified in incomplete Freunds adjuvant or bound to aluminum hydroxide. rPBOMP-1 was bound to alum by mixing rPBOMP-1 at a concentration of 500 ug/ml in 0.85% saline with alum at a concentration of 500 ug/ml at a 1:1 ratio. The mixture was shaken at 37° C. for 3 hours and the alum pelleted by centrifugation. Supernatent was assayed by BCA protein assay (Pierce Chem. Co, Chicago, Ill.) for unbound protein. None was detected. Alum was resuspended in physiological saline at 500 ug/ml. rPBOMP-1 was emulsified in incomplete Freund's adjuvant (Difco) in a 1:1 ratio. Animals were immunized intramuscularly with 50 ug of either preparation at 4 week intervals. Animals were bled at weeks 0, 6, and before each immunization. Sera were assayed for anti-PBOMP-1 and anti-rPBOMP-1 antibody using ELISA and Western blot analyses.

Immunization with the recombinant PBOMP-1 elicited antibody titers against recombinant PBOMP-1 and PBOMP-1 obtained from *H. influenzae* (designated native PBOMP-1) as determined by ELISA assays. Results are illustrated in Table 9.

TABLE 9

| ELISA TITERS OF ANTISERA AGAINST rPBOMP-1 | | | |
|---|---|---|---|
| ANTI-rPBOMP-1 | | ELISA Titer[a] Against | |
| Antisera | Adjuvant | rPBOMP-1 | Native PBOMP-1 |
| Week 0 | Alum | 800 | 800 |
| Week 6 | Alum | 12,800 | 12,800 |
| Week 0 | IFA | 800 | 800 |

TABLE 9-continued

| ELISA TITERS OF ANTISERA AGAINST rPBOMP-1 | | | |
|---|---|---|---|
| ANTI-rPBOMP-1 | | ELISA Titer[a] Against | |
| Antisera | Adjuvant | rPBOMP-1 | Native PBOMP-1 |
| Week 6 | IFA | 12,800 | 12,800 |

[a]ELISA-titer represents the reciprocal of the highest dilution of antiserum yielding twice the background level.

As shown in Table 9, immunization of animals with rPBOMP-1 in either alum or IFA elicited significant titers of antibody reactive with both rPBOMP-1 and native PBOMP-1 at 6 weeks post-immunization.

8.2 Enhanced Expression of PBOMP-2 in E. coli

PBOMP-2 is also expressed at low levels (less than 1% of cell protein) from plasmid pAA130. Expression of PBOMP-2 is apparently under control of its native promoter.

In order to improve the yield of PBOMP-2, the PBOMP-2 gene in pAA130 was cleaved at a unique SspI restriction site 5 bases 5' to the PBOMP-2 initiation codon and ligated to the SmaI site of pUC19 (FIG. 24). The ligation results in a hybrid open reading frame (ORF) containing the entire PBOMP-2 ORF (including the signal sequence) plus 18 codons from pUC19 and 2 codons from the gene fusion site. The protein product of this fusion gene has a predicted molecular weight of 17,999 daltons; and is expressed under regulation of lac promoter. This plasmid is designated pPX163.

When plasmid pPX163 was transformed into E. coli JM103 and induced with IPTG, a protein of 17,500 daltons apparent molecular weight was expressed. In addition, a protein doublet at 15,000 daltons molecular weight was observed. All three proteins were recognized by anti-PBOMP-1 antisera on Western Blot (FIG. 25). By Coomassie blue staining of SDS-PAGE, the three forms of recombinant PBOMP-2 comprised approximately 15% of total cell protein after lac induction (FIG. 25, Lane 3). The three forms of recombinant PBOMP-2 expressed from pPX163 have been isolated and N-terminal peptide analysis reveals that:

1. The 17,500 dalton apparent MW band is the predicted pUC19/PBOMP-2 hybrid protein;
2. The upper 15,000 dalton MW band starts at the first methionine residue of the PBOMP-2 signal sequence (i.e. the initiation codon of the PBOMP-2 ORF); and is apparently due to reinitiation of translation at this point; and
3. The lower 15,000 dalton MW band is blocked to N-terminal analysis and can be labeled with $^{14}$C-palmitate. Hence, this band consists of lipoprotein processed PBOMP-2.

9 MAPPING OF EPITOPE DETERMINANTS OF PBOMP-1

9.1 Synthetic and Cleavage Peptides

Most antibodies recognize antigenic determinants on proteins that are conformation-specific, formed by residues adjacent in space but not in primary sequence. A small proportion of antibodies recognize linear portions of the protein molecule. These linear or continuous epitopes, usually consist of about 5-10 amino acids and protrude from the protein surface, forming the corner or bends of the molecule and assuming reverse turns or loop structures. For the most part, continuous epitopes are hydrophilic and surface accessible. Computer algorithms of Hopp and Wood (1981, Proc Natl. Acad. Sci. USA 78:3824-3828) and Chou and Fasman (1978, Ann. Rev. Biochem. 47:251-276) were used to identify several hydrophilic regions (indicated by cross-hatched rectangular boxes in FIG. 26) of PBOMP-1 (amino acid sequence is shown in FIG. 11) that contained reverse turns (indicated by solid arrows in FIG. 26), each based on a tetrapeptide moving average. This computer search revealed hydrophilic turns predominating near the amino and carboxyl-terminal regions of PBOMP-1.

Five peptides, P1-P5, corresponding to the two end termini were selected for chemical synthesis. Peptide P1 corresponds to the N-terminal residues 1-20 of the mature protein (see FIG. 26 and 27). The remaining four peptides, P2-P5, are a nested series from the C-terminal end of PBOMP-1; the longest of these is P5, a 38 amino acid sequence containing residues 97-134 of the mature protein. Synthetic peptides were prepared by the solid phase method of Merrifield (1964, J. Am. Chem. Soc. 85:2149-2154) utilizing symmetric anhydride coupling chemistry except for the amino acids arginine, asparagine, and glutamine, for which 1-hydroxybenotriazole esters were used. The synthesis was carried out with an Applied Biosystems (Model 430A) automated peptide synthesizer. Each amino acid was double-coupled, resulting in stepwise yields of greater than 99.5% as indicated by the ninhydrin test. Peptides were cleaved from the resin by anhydrous hydrogen fluoride.

Proteolytic fragments of PBOMP-1 were obtained by digesting with a variety of proteases. EndoLys-C digestion resulted in the generation of a large 63 amino acid peptide (residues 1-63) of the mature protein. Tyr 87-Glu 121 was obtained from a digest with Staphylococcus V8 protease and Gly 18-Arg 85 was derived from an endoArg-C digestion.

Both chemically synthesized peptides and proteolytic fragments were analyzed by reverse-phase HPLC on a Vydac C4 column using an acetonitrile/water gradient with 0.1% trifluoracetic acid (TFA). In all cases, the purity of the synthetic peptides exceeded 95% as confirmed by amino acid sequencing.

9.2 Monoclonal Antibodies (Mabs)

Monoclonal antibodies were produced and purified as described in Section 6.2.2. Briefly, hybridoma cell lines secreting antibodies to PBOMP-1 were obtained by fusion of mouse myeloma cell line, X63. Ag8,6543 with spleen cells obtained from a C57/B1 mouse immunized with PBOMP-1. Desired hybridomas were recloned by limiting dilution and screened for reactivity for PBOMP-1 by Western Blot. Selected hybridomas were injected into Balb/c mice for growth as ascites.

A total of 43 hybridoma clones secreting anti-PBOMP-1 antibodies were obtained from the fusion experiments. Using competitive ELISA, we demonstrated that extensive cross-competition exists among Mabs, thus indicating that they recognized overlapping or very close antigenic determinants. Mabs were categorized according to their reactivity profiles into seven groups. Representative Mabs from these groups were used in further experiments, to determine and define useful contiguous epitopes for vaccine formulations.

9.3 Epitope Mapping with Mabs

9.3.1 Reactivity of Synthetic Peptides via Direct Elisa Assays

A direct ELISA assay was used to determine the binding of Mabs to synthetic peptides of PBOMP-1. As indicated in Table 10, only two Mabs, G204-2 and G194-3, reacted directly with the P1 peptide. These two Mabs apparently, recognize the same epitope since they competed with each other in competition binding experiments (data not shown). The remaining Mabs did not react with any of the peptides under the conditions used to coat the microtiter plates.

TABLE 10

DOT BLOT ASSAY TO DETERMINE BINDING OF MAB TO SYNTHETIC PEPTIDES SEGMENTS OF PBOMP-1

| PEPTIDE | G SERIES MAB | | | | | | | | | |
|---|---|---|---|---|---|---|---|---|---|---|
| | 196-3 | 204-2 | 216-3 | 219-3 | 212-6 | 214-3 | 194-3 | 190-8 | 56-5 | 130-3 |
| P1 CYS1-TYR20 | − | ++ | − | − | − | − | + | − | − | − |
| P5 LYS97-TYR134 | − | − | − | − | − | − | − | − | − | − |
| P4 LYS103-TYR134 | − | − | − | − | − | − | − | − | − | − |
| P3 LYS113-TYR134 | − | − | − | − | − | − | − | − | − | − |
| P2 ASP120-TYR134 | − | − | − | − | − | − | − | − | − | − |

9.3.2 Inhibitory Activity of Synthetic Peptides

The relative abilities of the synthetic peptides to inhibit the binding of the various Mabs to PBOMP-1, coated on the microtiter plates, are shown in Table 11. All of the monoclonal antibodies used in the competition ELISA (see Section 6.2.2 for detailed description of the procedure) reacted with PBOMP-1. Peptide P1 was 100% effective in inhibiting the binding of Mabs G204-2 and G194-3 to native PBOMP-1. Both of these Mabs also reacted directly with the P1 peptide (see above). Thus, the epitope(s) recognized by Mabs G204-2 and G194-3 lies within the first twenty amino acids of PBOMP-1.

The binding of Mabs G196-3, G212-6, G214-3, and G190-8 to PBOMP-1 was effectively inhibited (100%) by all of the C-termini peptides, P2-P5 (Table 11). These four Mabs must be recognizing an epitope(s) contained within the P2 peptide, a 15 amino acid sequence spanning Asp120-Tyr134.

Both Mabs G187-1 and G216-3 were strongly inhibited from binding to PBOMP-1 coated on plate by the P4 and P5 peptides (Table 11). On the other hand, both the P3 and P2 peptides were minimally effective in inhibiting the binding of these two Mabs to PBOMP-1. These inhibition data indicated that the 10 amino acid region (K-L-G-T-V-S-Y-G-E-E-K, residues 103-113 of the mature protein) contains an epitope recognized by Mabs G187-1 and G216-3. It is possible that this 10 amino acid region may contain two sites since Mabs 216-3 and G187-1 are from two non-crossreacting groups.

peptide (residues 1-63 of the mature protein) obtained from endoLys-C digestion, reacted with Mab G204-2. This observation was not surprising since the N-terminal 20 amino acid sequence is contained within this cleavage peptide. A peptide, Tyr87-Glu121, obtained from a V8 digest, reacted with Mab G216-3. This Mab has been shown (see above) to recognize a 10 amino acid sequence, residues 103-113 of the mature protein, which is encompassed by this V8 peptide. Finally, Mab G219-3, which did not bind with any of the synthetic peptides, was shown to react with a 68 amino acid peptide, Gly18-Arg85, derived from an endoArg-C digestion.

In summary, these studies involving the binding of Mabs to synthetic peptides and peptides generated by proteolytic digestion revealed the presence of four continuous antigenic regions of PBOMP-1. A schematic diagram representing the mapping of epitopes recognized by Mabs is depicted in FIG. 28. Two of the four determinants were localized at the chain termini, i.e, the N-terminal residues 1-20 and the C-terminal 120-134 of the mature protein. The third antigenic region, recognized by Mab G216-3 and G187-1, was localized to a small amino acid sequence (10 amino acids) spanning residues 103-113 of the mature protein. Finally, a rather large antigenic region, recognized by Mab G219-3, is encompassed by residues Gly18-Arg85. Since the latter peptide is quite large, the epitope could likely be conformation-dependent, since attempts so far to narrow it down have resulted in loss of antigenicity.

9.4 Functional Activity of Mabs

The functional activity of the Mabs were tested in a bactericidal assay against *H. influenzae* strain S2. The complement used was precollostral calf serum (PCCS) adsorbed 2× with washed S2 whole cells. Bacteria were grown overnight in brain heart infusion (BHI) broth supplemented with hemin at 10 ug/ml and NAD at 2 ug/ml (BHIXV), then diluted 1:15 in fresh broth

TABLE 11

COMPETITION BETWEEN PBOMP-1 AND SYNTHETIC PEPTIDE SEGMENTS OF PBOMP-1 FOR ANTI-PBOMP-1 MAB IN ELISA

| PEPTIDE | % INHIBITION BINDING OF MAB | | | | | | | | |
|---|---|---|---|---|---|---|---|---|---|
| (200 ug/ml) | 196-3 | 212-6 | 214-3 | 190-8 | 204-2 | 194-3 | 216-3 | 187-1 | 219-3 |
| P1 CYS1-TYR20 | 0 | 0 | 0 | 0 | 100 | 100 | 22 | 0 | 0 |
| P5 LYS97-TYR134 | 100 | 100 | 100 | 100 | 12 | 0 | 100 | 78 | 0 |
| P4 LYS103-TYR134 | 100 | 100 | 100 | 100 | 20 | 11 | 100 | 71 | 0 |
| P3 LYS113-TYR134 | 100 | 100 | 100 | 100 | 9 | 0 | 21 | 0 | 0 |
| P2 ASP120-TYR134 | 100 | 100 | 100 | 100 | 0 | 0 | 17 | 0 | 0 |

9.3.3 Reactivity of Mabs with Proteolytically Cleaved PBOMP-1 Fragments

PBOMP-1 peptide fragment-s generated by proteolytic cleavage were tested for reactivity with a limited number of anti-PBOMP-1 Mabs by direct dot blot and Western immunoblot analysis. A large 63 amino acid and incubated at 37° C. with aeration. Cells were grown to an OD at 490 nm of 0.9 (approximately 10 CFU/ml). Bacteria were diluted 40,000 fold by a series of dilution in sterile phosphate-buffered saline containing 0.15 mM $CaCl_2$, 0.5 mM $MgCl_2$ and containing 0.5% bovine serum albumin (PCMA). The final dilution was done in PCMA with PCCS at a 4:1 ratio.

Ascites fluid was washed in PCMA by first diluting ten fold in the buffer then concentrating back to original volume by using a Centricon microconcentration unit with a 10,000 cut-off membrane. Monoclonal mouse antiserum was reacted with saturated ammonium sulfate at 35% final concentration at 4° C. overnight. The sample was centrifuged for 10 minutes at 4° C. in an Eppendorf table-top centrifuge. The supernatant was discarded and the pellet was resuspended in 10 times the original serum volume of PCMA. The sample was restored to original volume using a centricon unit with a 10,000 cut-off membrane. The sample was washed four more times to remove any ammonium sulfate.

Fifteen microliters of the serum sample were placed in the first well of a sterile 96 well U-bottom microtiter plate held on ice. Two-fold serial dilutions using PCMA were done in the remaining wells. The plates were removed from the ice and 15 ul of the cell/complement suspension were added to the serum in the wells. The plates were incubated at 37° C. for 45 minutes. A 10 ul sample from each well was spread on a BHIXV plate was incubated overnight at 37° C. The bactericidal titer was reported as the reciprocal of the highest dilution capable of reducing the number of CFU's by 50% compared to a nonantibody containing control.

The results of these bactericidal assays are shown in Table 12. Of the ten anti-PBOMP Mabs tested, G102-5, G56-5, G216-3, and G204-2 were positive for bactericidal activity. An unrelated viral Mab showed no activity. Interestingly, two of the four defined antigenic determinants of PBOMP-1, N-terminal residues 1–20 and 103–113 of the mature protein, were separately recognized by two bactericidal Mabs, namely G204-2 and G216-3, respectively. The bactericidal activity of these two Mabs supports the contention that these two regions are surface-exposed on the bacteria. Surprisingly, preliminary inhibition data suggested that Mab G204-2 exhibited a stronger reactivity to the synthetic N-terminal peptide than to native PBOMP-1. This is in marked contrast to the usually low antigenic activity associated with synthetic peptides, when measured with antibodies to whole protein. Obviously, the free N-terminal peptide in solution was mimicking the structure of this peptide sequence in the mature PBOMP-1 molecule and may be sterically more accessible for antibody bonding. In addition to Mabs G204-2 and G216-3, two other Mabs, G102-5 and G56-5, have been found to be bactericidal to Haemophilus organisms. Since they did not react with synthetic or cleavage peptides, these bactericidal Mabs were thought to be recognizing discontinuous (or conformational) epitopes.

TABLE 12

BACTERICIDAL ACTIVITY OF ANTI-PBOMP-1 MONOCLONAL ANTIBODIES AGAINST NONTYPABLE H. INFLUENZAE STRAIN S2[a]

| Mabs | Group | Results |
|---|---|---|
| G102 | VI | + |
| G56-5 | II | + |
| G216-3 | — | + |
| G146 | II | — |
| G204-2 | VII | + |
| G125-6 | I | — |
| G196-3 | III | — |
| G64 | VI | — |
| G25-2 | III | — |
| G219-3 | — | — |
| G130-3 | II | — |
| L7-4 | viral | — |

[a]Conditions used for the bactericidal assay are described in the text. Of the eleven anti-PBOMP-1 Mabs, four were positive for bactericidal assay against a nontypable Haemophilus S2 strain. An unrelated viral monoclonal showed no activity.

10 INDUCTION OF A BIOLOGICALLY FUNCTIONAL ANTIBODY BY A CONJUGATE OF A SYNTHETIC N-TERMINAL PEPTIDE OF PBOMP-1

10.1 Chemical Characterization of Peptide-Protein Conjugates

The peptide selected for synthesis in this study corresponded to the N-terminal 20 amino acid sequence, Cys1-Tyr20 (P1) of the mature PBOMP-1 using the procedures described in Section 9.1. As also described in Section 9.1., the peptide was purified by reverse-phase HPLC. The final purity (95%) of the synthetic peptides was confirmed by direct amino acid seqencing with an Applied Biosystem Model 77A protein sequenator.

Conjugates were prepared using MBS (3-maleimidobenzoic acid N-hydroxysuccinimide ester, Pierce Chemical Co., Rockport, Ill.) as the cross-linking reagent (Liu et al., 1979, Biochemistry 18:690–697). The conjugation process proceeded in a stepwise manner. First, the epsilon amino groups of surface lysinyl residues of BSA (or thyroglobulin) were N-acylated with an excess of MBS. The coupling reaction was carried out at room temperature in phosphate-buffered saline, pH 7.3, by mixing the protein carrier with MBS at a molar ratio of 1:100. The reaction mixture was desalted over Sephadex-G-50 to remove excess MBS reagents. Second, the peptide Pl, bearing an amino terminal cysteinyl residue, was reduced with sodium borohydride to ensure a reactive sulfhydryl group. Third, conjugation was achieved by adding the reduced peptide to the solution containing the BSA-MBS or thyroglobulin-MBS derivative and allowing the covalent reaction to take place overnight. Dialysis was performed to remove excess unreacted peptide prior to freeze-drying. Covalency was demonstrated by a shift in molecular weight on SDS gels and by Western blot analysis. The shift in molecular weight corresponded to 7 molecules of peptide per BSA molecule and 25 molecules of peptides per thyroglobulin molecule. Moreover, the conjugate bands reacted with both anti-PBOMP-1 and anti-peptide antisera on a Western blot.

To enhance immunogenicity, the N-terminal peptide was fatty acid acylated with palmityl groups according to the method of Hopp (1984, Mol. Immuno. 21: 13–16). Essentially, the peptide was elongated at the amino terminus with di-glycine spacer followed by a lysyl residue. Both the alpha- and epsilon-amino groups of N-terminal lysine were acylated with palmitic acids by the symmetric anhydride coupling procedure. Completeness of the fatty acid acylation was verified by (1) a negative ninhydrin test indicating complete derivitization of lysyl amino groups, (2) refractoriness of the peptide toward amino acid sequencing due to blocked N-terminus, and (3) longer HPLC elution time using a reverse-phase column due to increased hydrophobicity.

10.2 Preparation of Polyclonal Anti-PBOMP-1 N-terminal (N-1-20) Peptide Antiserum Swiss-Webster mice which were at least 6 weeks old were obtained from Taconic Farms (Germantown, NY). Groups of 5 mice were pre-bled and vaccinated intramuscularly with one or 10 ug of a (N-1-20) carrier peptide conjugate, with and without complete Freund's adjuvant (CFA). Animals were boosted at week 4 with the same dose of vaccine used for priming. Mice primed with CFA were boosted with conjugate in incomplete Fueund's adjuvant (IFA). Mice were bled at weeks 4 and 6.

Rabbits obtained from Taconic Farms (Germantown, NY) were immunized with 10 ug peptide-conjugate and bled according to the same vaccination schedule as described above.

10.3 Preparation of Monoclonal Antibodies to PBOMP-1 N-terminal (N-1-20) Peptide Hybridoma cell lines secreting antibodies to the PBOMP-1 N-terminal peptide-carrier conjugate were obtained by the fusion of the mouse myeloma cell line, X63.Ag8.6543 with spleen cells obtained from a C57/B1 mouse immunized with (N-1-20)-carrier conjugate as described in Section 6.2.2. Desired hybridomas were recloned by limiting dilution (see Section 6.2.2. for a detailed description of procedure) and screened for reactivity with (N-1-20)--carrier conjugate by Western Blot. Selected hybridomas were injected in Balb/c mice for growth as ascites by standard procedures (Brodeur et al., supra).

10.4 Immunogenicity of PBOMP-1 N-terminal (N-1-20) Peptide-carrier Conjugate The immunogenicity of a PBOMP-1 N-terminal (N-1-20) peptide conjugate was examined in one study. Mice and rabbits were immunized subcutaneously with 10 ug of the (N-1-20) peptide-carrier conjugate (or PBOMP-1) emulsified in CFA, followed 4 weeks later with a booster injection in IFA. Animals were bled 14 days after the last injection.

Anti-(N-1-20) peptide activity of the animal antisera was determined by the ELISA method as described in Section 6 2.2., supra. Briefly, 96 well polystyrene plates (NUNC Intermed, Thousand Oaks, Calif.) were coated with PBOMP-1 or a N-1-20)-peptide carrier conjugate, i.e., (N-1-20)-peptide-BSA, at a concentration of 1 ug/ml in PBS. Plates were incubated overnight at 37° C. in humidified chamber. Prevaccination serum was always used as a negative control and a polyclonal anti-PBOMP-1 serum was used as a positive control. Alkaline phosphatase coupled to IgG anti-mouse antisera was used as secondary antibody. The reaction was developed with p-nitrophenylphosphate at 1 mg/ml in diethanolamine buffer. Optical density (OD) at 410 and 690 nm was read using a Bio-Tek 310 Autoreader. Results are presented in Table 13.

TABLE 13

| ANTIBODY RESPONSE TO N-TERMINAL PEPTIDE AS MEASURED BY ELISA | | | |
|---|---|---|---|
| | (N-1-20):BSA | PBOMP-1 | BSA |
| MOUSE ANTI-(N-1-20) SERA[a] | | | |
| Week 0 | <1:100 | 1:400 | <1:500 |

TABLE 13-continued

| ANTIBODY RESPONSE TO N-TERMINAL PEPTIDE AS MEASURED BY ELISA | | | |
|---|---|---|---|
| | (N-1-20):BSA | PBOMP-1 | BSA |
| Week 6 | 1:1,024,000 | 1:512,000 | <1:4000 |
| RABBIT ANTI-(N-1-20) SERA | | | |
| #1 Week 0 | 1:400 | <1:1000 | <1:100 |
| #2 Week 0 | 1:200 | <1:1000 | <1:100 |
| #1 Week 6 | 1:256,000 | 1:32,000 | <1:100 |
| #2 Week 6 | 1:4,096,000 | 1:512,000 | <1:100 |
| MOUSE ANTI-PBOMP-1 SERA[a] | | | |
| Week 0 | <1:100 | <1:100 | <1:500 |
| Week 6 | 1:256,000 | 1:512,000 | <1:500 |

[a]The mouse sera are pooled sera from five animals.

The ELISA results showed that (N-1-20)-carrier conjugate was highly effective in eliciting mouse and rabbit anti-peptide antibodies having the ability to recognize the peptide (attached to BSA carrier) and native PBOMP-1 (see Table 13). Mice immunized with (N-1-20)-carrier conjugate, gave a high anti-peptide titer response of 1:1,024,000. The mouse anti-peptide antibodies also strongly recognized the parent PBOMP-1 in the ELISA at a 1:512,000. These anti-peptide antibodies appear to be specific to the N-terminal peptide since only negligible amounts of these antibodies reacted with BSA.

The maximum rabbit anti-peptide titer was obtained with Rabbit #2 at 1:4,096,000. Rabbit #1 also had a strong anti-peptide titer of 1:256,000. Both the rabbit anti-peptide sera were capable of recognizing native PBOMP-1 as seen by the 32-fold and 512-fold increase in titers compared to the preimmune titers of Rabbit #1 and Rabbit #2, respectively. Interestingly, antiprotein antibodies were raised to PBOMP-1 that reacted with the N-terminal peptide at greater than 1:256,000 ELISA titer, thus suggesting that the N-terminal epitope is immunodominant.

The SDS/Western blot technique was also used to evaluate the mouse antipeptide sera raised to the (N-1-20)-carrier conjugate. The antipeptide antibody and the mouse anti-PBOMP-1 polyclonal sera were observed to react with both conjugates: peptide-BSA and peptide-thyroglobulin, and also with native PBOMP-1 on immunoblots. The Western blot results also revealed that little, if any, antibodies were made to the MBS-spacer since the antipeptide sera did not react with a control conjugate consisting of 'nonsense' peptide (of an equivalent size) linked to BSA through the MBS spacer.

The free peptide (10 ug dose) was not immunogenic, even when administered with FCA. Contrary to other findings (Hopp, 1984, Mol. Immuno. 21:13-16), the palmityl-peptide conjugate was also not immunogenic in mice. In order to elicit a useful antibody response, the N-terminal peptide was coupled to a protein carrier, e.g., thyroglobulin.

10.5 Functional Assays: Bactericidal Activity of Anti-(N-1-20) Peptide Antibodies The bactericidal activity (BC) of mouse anti-(N-1-20) peptide antisera against H. influenzae S2 strain was measured using procedures described in Section 9.4, supra.

The results are presented in Table 14.

TABLE 14
BACTERICIDAL ACTIVITY OF ANTIPEPTIDE
ANTIBODIES TO N-TERMINAL PEPTIDE OF PBOMP-1

|  | BC Titer[a] | |
|---|---|---|
|  | Pre-bleed | week 6 |
| MICE IMMUNIZED WITH |  |  |
| Free (N-1-20) peptide | 1/5 | 1/10 |
| Peptide-carrier Conjugate | 1/5 | 1/40 |
| Native PBOMP-1 | 1/5 | 1/80 |
| RABBITS IMMUNIZED WITH PEPTIDE-CARRIER CONJUGATE |  |  |
| Rabbit 1 | 1/320 | 1/2560 |
| Rabbit 2 | 1/320 | 1/1250 |

[a]Bactericidal activity was measured against a nontypable *H. influenzae* strain S2.

The mouse anti-(N-1-20) peptide-conjugate antibodies were capable of killing S2 organisms at a dilution of 1/40, compared to mouse anti-PBOMP-1 polyclonal sera at 1/80. As a control group, mice immunized with free peptide (unconjugated, administered in CFA) did not yield an effective bactericidal antisera (Table 14). In fact, no significant (greater than two-fold) immune response to the N-terminal (N-1-20)- peptide was observed in the control group.

The bactericidal activities of the two individual rabbit anti-(N-1-20) peptide antisera are also shown in Table 14. Even though the two preimmune sera possessed bactericidal activity, the post immunization sera were more efficient in mediating complement-dependent killing of *H. influenzae*. Rabbit #1 gave a bactericidal (BC) titer of 1/2560, representing an eight fold rise over its preimmune level; whereas, Rabbit #2 gave a titer of 1/1280, representing a 4-fold rise. We expected rabbit #2 antisera, which had the higher anti-(N-1-20) titer, to have the higher BC activity; however, rabbit #1 antiserum exhibits better killing effect.

11. ISOLATION AND CHARACTERIZATION OF THE RECOMBINANT-DNA DERIVED PBOMP-2: PBOMP-1 FUSION PROTEIN

11.1. Construction of Plasmid pPX183 for the Expression of PBOMP-2: PBOMP-1 in *E. coli*

The construction of plasmid pPX183 for the expression of the PBOMP-2: PBOMP-1 fusion protein under the control of the lac promoter is described below and represented diagramatically in FIG. 30.

DNA fragments including the PBOMP-1 and PBOMP-2 genes were derived from plasmids pPX167 and pPX163 respectively. The isolation of each of these plasmids is described in Sections 8.1 and 8.2, supra. Purified DNA fragments of plasmids pPX163 and pPX167 were each separately digested with ScaI to completion. The pPX163 digest was then further treated with HindIII to yield a partial digest. A resulting ScaI-HindIII fragment of 2.7 Kb, including the origin of replication, the lac promoter, and the PBOMP-2 gene was isolated from an agarose gel as described in Section 6.4.2., supra. A 1.4 Kb ScaI-HindIII fragment including the PBOMP-1 gene and regulatory sequences was isolated in a similar fashion from a complete ScaI-HindIII digest of pPX167. The two isolated ScaI-HindIII fragments were then ligated together using procedures described in Section 6.4.3. Selection of ampicillin resistant transformants ensured the reformation of an active β-lactamase gene (interrupted by the ScaI site). This procedure yielded a 4.1 Kb plasmid which was designated pPX183. This plasmid encodes a PBOMP-2: PBOMP-1 fusion protein with the two PBOMP genes ligated in frame as shown in FIG. 30.

11.2. Expression of the PBOMP-2: PBOMP-1 Fusion Protein

Plasmid pPX183 was transformed into *E. coli* JM103 and the resulting strain was tested for production of a recombinant fusion protein under lac regulation. Coomassie Blue stained SDS-polyacrylamide gels of total cell extracts of IPTG-induced JM103 cells containing plasmid pPX183 revealed a new protein of about 30,000 daltons molecular weight which comprised 1-2% of total cell protein. Western blot analysis showed that this recombinant fusion protein reacted with monoclonal antibodies specific for PBOMP-1 and also with those specific for PBOMP-2. Thus the fusion protein product encoded by plasmid pPX183 carries epitopes of both PBOMP-1 and PBOMP-2.

11.3. Construction of Plasmid pPX199 Expressing PBOMP-2: PBOMP-1 Fusion Protein Although plasmid pPX183 encodes a hybrid PBOMP-1/PBOMP-2 protein, i.e. a fusion protein, the protein expressed by this plasmid contains additional amino acids encoded by the pUC19 vector. Specifically, the nucleotide sequence of pPX183 contains 18 additional codons at the 5' end from pPX163 and 13 additional codons at the fusion junction—31 codons derived from the pUC19 vector. A new fusion gene lacking most of this excess information was constructed as follows.

First, a derivative of pAA130 containing the PBOMP-2 gene was digested with SspI, which cleaves 5 nucleotides 5' to the initiation codon of PBOMP-2, and then with HindIII which cleaves the PBOMP-2 gene at codon 148, i.e., 6 codons from the 3' end of the gene. Sequence analysis showed that this fragment could be ligated into plasmid pUC8 and digested with SmaI and HindIII to generate a recombinant PBOMP-2 gene with seven codons fused to the 5' end of the "native" gene and six amino acids missing at the 3' end. A plasmid was produced in this manner and designated pPX195 (see FIG. 31).

Next, plasmid pPX167 containing the PBOMP-1 gene (see Section 8.1, supra) was modified in the following manner: the BamHI site at the 3' end of the gene was removed by partial digestion with BamHI and religated by treatment with *E. coli* DNA polymerase I (Klenow fragment). The resulting plasmid designated pX188 was verified by restriction analysis and production of rPBOMP-1 (see FIG. 31). The 5' end of the rPBOMP-1 gene of pPX188 was modified by removal of the HindIII - BamHI fragment from the pUC19 polylinker region and insertion of a synthetic oligonucleotide having HindIII and BamHI sticky ends and the six 3' codons of PBOMP-2. This construction was verified by DNA sequence analysis and the plasmid designated pPX198.

Plasmids pPX195 and pPX198 were digested with HindIII and ScaI and the fragments carrying the PBOMP-2 and PBOMP-1 genes respectively were isolated and ligated together. The resulting plasmid was designated pX199 (FIG. 31). Plasmid pX199 expresses a PBOMP-2: PBOMP-1 fusion gene with seven additional codons (from pUC8) at the 5' end and two at the fusion junction. The fusion protein has an apparent molecular weight of about 32000 daltons by SDS- PAGE (see FIG. 32) and is recognized on Western blots by polyclonal antisera against PBOMP-1, PBOMP-2, PBOMP-2 Mab 61-1 (See Section 6.2.2) and a variety of PBOMP-1 Mabs.

11.4. Expression of Signal-less PBOMP-2: PBOMP-1 Fusion Protein

PBOMP-2: PBOMP-1 fusion protein gene of pPX199 encodes the PBOMP-2 signal peptide, and the resulting fusion protein is modified as a lipoprotein and tightly associated with the outer membrane of *E. coli* cells expressing it. This fusion protein is difficult to separate from the membrane and poorly soluble in aqueous solvents. Construction of a plasmid which expresses a signal-less PBOMP-2: PBOMP-1 fusion protein is illustrated in FIG. 33.

First, a signal-less form of the PBOMP-2 gene was constructed in the following manner: The 660 bp EcoRI/SalI restriction fragment of plasmid pPX163 encoding the PBOMP-2 protein was isolated and cleaved at the unique HphI site at nucleotide 91 of the gene and the 545 bp HphI/EcoRI fragment encoding the carboxyterminal 125 amino acids of PBOMP-2 was isolated.

The following synthetic oligonucleotide linker was then constructed to restore a modified 5' end of the PBOMP-2 gene:

```
XbaI        SD box      NcoI            EcoRv        HphI
CTAGAATAAAGGAAACAAACCATGGCAAATACTGATATCTTCAGCGGTGATGTTTATA
    TTATTTCCTTTGTTTGGTACCGTTTATGACTATAGAAGTCGCCACTACAAATATC
                         Met  . . . . . . . . . . . . . . . . . . . . . . . . . . . .
```

The linker was designed to create a modified PBOMP-2 gene with the following features:
(1) Absence of the signal peptide encoding sequences,
(2) Restoration of the entire mature PBOMP-2 sequence, except the N-terminal cysteine residue (replaced by methionine),
(3) A new and unique NcoI restriction site at the initiation codon,
(4) A wobble base change to generate a new and unique EcoRV restriction site at nucleotide 12 of the coding region,
(5) A new translation initiation site (SD box), and
(6) An upstream in frame stop codon (TAA) to prevent lac translational readthrough.

The linker was mixed at a 1:1:1 molar ratio with the HphI/EcoRI fragment from pPX163 and pUC19 DNA cleaved with XbaI and EcoRI and ligated. The ligation mixture was transformed into *E. coli* DH5 lacI$^q$ and AmpR colonies were screened for PBOMP-2 production with Mab 61-1. Several positive colonies were found and the construction was verified by restriction and DNA sequence analysis. One of the isolates was designated pPX510.

Plasmid pPX510 encodes a 14,000 apparent dalton molecular weight protein by SDS-PAGE which was recognized by both polyclonal anti-PBOMP-2 sera and anti-PBOMP-2 Mab 61-1. Expression of the signal-less recombinant PBOMP-2 was under lac regulation, and fully induced cells expressed the construction as ~5% of total cell protein.

A signal-less fusion gene was then constructed from pPX510 and pPX198 in a manner analogous to the construction of pPX199 (see Section 11.3, supra). Briefly, the two plasmids were digested with HindIII and ScaI and the PBOMP-1 and PBOMP-2 fragments were ligated together. The resulting plasmid was transformed into *E. coli* DH 5α (BRL, Gaithersburg, Md.) and was designated pPX512. The signal-less fusion protein expressed by pPX512 had an apparent molecular weight of 30,000 daltons by SDS-PAGE and was recognized by polyclonal antisera against both PBOMP-1 and PBOMP-2. The fusion protein was also recognized by PBOMP-2 MAb 61-1 and all PBOMP-1 Mabs tested by Western blot analysis.

12. EFFICACY OF FUSION PROTEIN SUBUNIT VACCINES

12.1. Preparation of Anti-PBOMP-2: PBOMP-1 Antibodies

Substantially pure PBOMP-2: PBOMP-1 was isolated from an SDS-PAGE gel of cell extracts of *E. coli* JM103 containing pPX183 (see Section 11.1, supra). The position of the fusion protein band on the preparative SDS-PAGE gel was deduced by Coomassie Blue staining of strips cut from the edges of the gel. Slices containing the fusion protein were soaked in Gel Elution Buffer (0.2M NaCl, 0.05M Tris, pH 8.0, 0.1% SDS and 0.1 mM EDTA) overnight at room temperature with gentle agitation. Extracted protein was estimated by a Lowry Protein assay with BSA as standard.

Two female New Zealand White rabbits were used in an initial immunogenicity study. Prebleeds (at week 0) were obtained prior to vaccination as a source of preimmune sera. Fifty micrograms of substantially pure PBOMP-2: PBOMP-1 fusion protein (adjusted to a volume of 100 μl) were mixed with an equal volume of CFA and injected intramuscularly into the rabbits at multiple sites. Blood samples were collected 3 weeks later and the rabbits were reimmunized at week 4 with 50 μg of fusion protein emulsified in IFA. Blood samples were then collected at week 7 and sera prepared for ELISA and bactericidal assays. Results of the ELISA and bactericidal activity assays are presented in Table 15.

TABLE 15

RESPONSE OF RABBIT POLYCLONAL ANTI-PBOMP-2: PBOMP-1 ANTISERA[a]

| Rabbit Serum | Bleed | Increase in BC titer[b] | Increase in ELISA titer Anti-PBOMP-1 | Increase in ELISA titer Anti-PBOMP-2 |
|---|---|---|---|---|
| 1 | wk 3[c] | 32× | 750× | 80× |
|   | wk 7[d] | 128× | 2000× | 2000× |
| 2 | wk 3[c] | 32× | 40× | 25× |
|   | wk 7[d] | 128× | 400× | 250× |

[a]See text for details of immunizations.
[b]Increase over titer at week 0 in BC against *H. influenzae* S2.
[c]Bleed taken after one immunization.
[d]Bleed taken after two immunizations.

Immunization with the recombinant fusion protein PBOMP-2: PBOMP-1 elicited antibody responses to both PBOMP-1 and PBOMP-2 as determined in ELISA assays and these antisera had bactericidal activity against the unencapsulated *H. influenzae* strain S2 (Table 15). These results show that PBOMP-2: PBOMP-1 fusion protein is highly effective in provoking an antibody response against both PBOMP-1 and PBOMP-2 and that this immunogenic response is biologically functional in a bactericidal assay.

In another series of experiments, adult chinchillas were used as a test system to demonstrate further the immunogenicity and efficacy of the PBOMP-1: PBOMP-2 fusion protein as a subunit vaccine formulation. The chinchilla serves as a model animal system because this animal when infected with *H. influenzae* develops an otitis media much like that seen in humans. (See, Barenkamp et al., 1986, Infect. Immun. 52:572-78).

As indicated in Section 11.3, the PBOMP-2: PBOMP-1 fusion protein expressed by *E. coli* JM103 containing pPX199 is modified as a lipoprotein and is tightly associated with the outer membrane of the *E. coli* host cells. Substantially pure PBOMP-2: PBOMP-1 was isolated from *E. coli* JM103 containing pPX199 by the following method entailing differential detergent extraction of the inner and outer membrane proteins of the *E. coli* host cells. Briefly, the inner membrane proteins of *E. coli* were extracted using 1% sarcosyl in 10 mM Tris-HCl pH 8, 5 mM EDTA leaving an unsoluble outer membrane-cell wall complex.

A subfraction enriched in PBOMP-2: PBOMP-1 fusion protein was obtained by differential detergent extraction of other outer membrane-cell wall components. The outer membrane proteins were extracted from the sarcosyl insoluble outer membrane cell wall components by sequential extraction with 1% Zwittergent 3-12 TM, 1% Zwittergent 3-14 TM in 10 mM Tris-HCl pH 8, 5 mM EDTA, 1% deoxycholate at 60° C. The PBOMP-2: PBOMP-1 fusion protein enriched insoluble material was obtained following centrifugation. The PBOMP-2: PBOMP-1 fusion protein was solubilized by extraction of the PBOMP-2: BOMP-1 enriched fraction with 1% Zwittergent 3-14, 50 mM Tris-HCl, 5 mM EDTA, pH 8.0, 6 M urea at 80° C. for 45 minutes. After solubilization, the urea was removed from the extracted fusion protein by dialysis against the same buffer without urea at room temperature overnight.

The apparent purity of the solubilized fusion protein was in the range of 75-80%. Approximately 25 mg of protein was solubilized from ~10-20 g wet weight fusion protein. The major protein was identified as the intact fusion protein. The major lower MW protein also was derived from the fusion protein since it contained the N-terminal region of the PBOMP-1 protein fused to the PBOMP-2 protein, as determined o by epitope analysis. The C-terminal § of the PBOMP-1 was lost from this protein. This may have been the result of proteolytic degradation, possibly during induction, or to premature termination of translation. The purity of this preparation is shown in FIG. 32.

Five adult chinchillas were used in one animal experiment. Preebleeds (at day 0) obtained via cardiac puncture prior to vaccination were used as a source of preimmune sera. Twenty five micrograms of substantially pure PBOMP-2: PBOMP-1 fusion protein, obtained from *E. coli* cells containing plasmid pPX199 as described above, absorbed onto alum was injected intramuscularly into the chinchillas. Blood samples were collected thirty days later and the animals were reimmunized at day 30 with 25 μg of purified fusion protein on alum. Blood samples were again collected via cardiac puncture at day 60. Sera was prepared for ELISA and bactericidal assays. ELISA assays were performed as described above using as antigen either substantially purified PBOMP-1 (Anti-PBOMP-1) or a recombinant form of PBOMP-2 (anti-PBOMP-2). The bactericidal activity of the serum samples was tested as described above in Section 7.1 using *H. influenzae* P860295, a clinical non-typable strain obtained from Dr. Charles Bluestone, Children's Hospital of Pittsburgh, Pa. Results of the ELISA and bactericidal activity assays are presented in Table 16.

TABLE 16

RESPONSE OF CHINCHILLA
ANTI-PBOMP-2: PBOMP-1 ANTISERA[a]

| Bleed[b] | ELISA Titer | | BC Titer |
|---|---|---|---|
| | Anti-PBOMP-1[c] | Anti-PBOMP-2 | |
| Pre | 466 | 799 | 1:5 |
| Post 1* | 970 | 20,297 | 1:40 |
| Post 2* | 9,675 | 109,480 | ≧1:1280 |

[a]See text for details of immunizations.
[b]Bleeds were taken at day 0 (Pre); at day 30 (Post 1*) and at day 60 (Post 2*).
[c]Bactericidal activity against *H. influenzae* P860295.

Immunization with 25 μg of the fusion protein PBOMP-2: PBOMP-1 elicited one of the highest titers of BC activity ever observed in our laboratory against an outer membrane of Haemophilus. Together with the high level of activity observed in the ELISA assays against both PBOMP-1 and PBOMP-2, the results in Table 16 show that the PBOMP-2: PBOMP-1 fusion protein is surprisingly highly effective in provoking an antibody response against both PBOMP-1 and PBOMP-2 in chinchillas. These results further demonstrate that the fusion protein elicits an immune response which is biologically active in a bactericidal assay against a clinical strain of *H. influenzae*.

12.2. PBOMP-2: PBOMP-1 Fusion Protein in Combination with E Protein Induces Anti-haemophilus Antibodies The E protein is another outer membrane protein of *H. influenzae* having a molecular weight of about 28,000 daltons. E protein exists as a lipoprotein in association with other outer membrane proteins of *H. influenzae*.

E protein from *H. influenzae* was obtained in substantially pure form as described in U.S. patent application Ser. No. 07/320,971 filed Mar. 9, 1989. Briefly, cell envelopes were isolated from Hib strain Eagan cells grown on either brain heart infusion medium containing 10 μg/ml hemin and 1 μg/ml NAD (BHI/XV) or mMIC (modification of Herriortt et al., 1970 J. Bacteriol., 101: 513-516 media). Cells were harvested from liquid cultures by centrifugation at 10,000×g, 4° C. for 10 minutes. The cell pellet was weighed and resuspended in 10 mM HEPES-NaOH (pH 7.4), 1 mM EDTA, with a volume equal to five times the wet weight of the cells. The cells were disrupted using a Gaulin homogenizer. The disrupted cell suspension was centrifuged at 10,000×g for 5 minutes at 4° C. to remove unbroken cells and large debris. The supernatant fraction was saved and NaCl added to 0.5M. Cell membranes were pelleted by centrifugation at 100,000×g for about 1 h at 4° C.

An outer membrane-cell wall complex was obtained by removing the inner membranes from the total membrane fraction by repeated extraction of the total membrane fraction with 2% Triton X-100 in 10 mM HEPES-NaOH, 1 mM MgCl₂, pH.7.4. The insoluble residue containing the outer membrane-cell wall complex was pelleted by centrifugation at 350,000×g for 30 minutes at 4° C. This complex was then resuspended in 50 mM Tris-HCl, 5 mM Na₂EDTA, pH 8 and stored 4° C.

Contaminating proteins were soluilized from *H. influenzae* cell envelopes by differential detergent extraction as follows. Cell envelopes prepared as described above were sequentially extracted twice with 1% sarcosyl in 50 mM Tris-HCl, 5 mM Na₂EDTA, pH 8. This extraction was repeated three times. The solubilized protein E-containing fractions were pooled and passed through a DEAE column equilibrated with 50 mM Tris-HCl, 5 mM Na₂EDTA, pH 8. The E protein was not retained under these conditions but the major protein contaminants were retained. The fall-through fractions containing E protein were then passed over a hydroxylapatite column which had been equilibrated with 50mM Tris-HCl, pH 8. The E protein was retained under these conditions. The hydroxylapatite column with the adsorbed E protein was then washed with one column volume of 50 mM Tris-HCl, pH 8. The E protein was eluted from the hydroxylapatite with 1% Zwittergent 3-14 TM in 0.3M dibasic phosphate, pH 8. Fractions containing protein E were pooled, concentrated by diafiltration, and precipitated with ethanol. The precipitated E protein was then solubilized again by differential detergent extraction. The precipitate was first extracted with 1% octylglucoside in 50 mM Tris-HCl, pH 8 and the insoluble E protein remained in the precipitate. The protein E was then solubilized with 1% Zwittergent 3-14 TM in 50 mM Tris-HCl, 5 mM Na₂EDTA, pH 8. E Protein prepared as described above is substantially pure and essentially free of endotoxin.

Twenty-five micrograms of the substantially pure E protein was mixed with 25 μg of substantially pure PBOMP-2: PBOMP-1 fusion protein obtained as described in Section 12.1, supra, diluted into 0.85% saline and absorbed with alum.

Adult chinchillas were injected intramuscularly with an aliquot of the mixture containing 25 μg of PBOMP-2: PBOMP-1 fusion protein and 25 μg of E protein. Blood samples were collected at day 0 immediately prior to the first immunization, at day 30 prior to the second immunization, and at day 60. ELISA assays were performed as described above using PBOMP-2: PBOMP-1 or E protein as antigen. Bactericidal assays were performed as above using *H. influenzae* P860295 as the test strain. Results of the ELISA and bactericidal assays are tabulated in Table 17.

TABLE 17

RESPONSE OF CHINCHILLA ANTI-PBOMP-2: PBOMP-1 ANTI-E ANTISERA[a]

| Bleed[b] | ELISA Titer | | | BC Titer[c] |
|---|---|---|---|---|
| | Anti-PBOMP-1 | Anti-PBOMP-2 | Anti-E | |
| Pre | 385 | 578 | <100 | <5 |
| Post 1* | 1423 | 64283 | 1137 | 160 |
| Post 2* | 134988 | 277204 | 206959 | >1280 |

[a]See text for details of immunizations.
[b]Bleeds were taken at day 0 (Pre); at day 30 (Post 1*) and at day 60 (Post 2*).
[c]Bactericidal activity against *H. influenzae* P860295.

Results of the ELISA studies show that the response to E protein was very high, achieving levels comparable to that of the PBOMP-2 portion of the fusion protein. No blocking effects were observed between E protein and fusion protein. Biologic activity of the antisera was measured using the BC assay. Twenty-five μg of E elicited one of the highest BC titers our laboratory has ever seen with antibodies against OMPs of Haemophilus. The BC titer was greater than that of the chinchillas which received only fusion protein. While it is not possible to state that the BC activity of the mixed vaccine antisera exhibited a synergistic or additive effect, the activity of the mixture is as effective or better than that of the fusion alone. These results strongly support the use of a mixture of the fusion protein in combination with the purified E protein as a vaccine against Haemophilus.

13. DEPOSIT OF MICROORGANISMS

The following *E. coli* strains carrying the listed plasmids have been deposited with the Agricultural Research Culture Collection (NRRL), Peoria, Ill. and have been assigned the following accession numbers:

| E. Coli Strain | Plasmid | Accession Number |
|---|---|---|
| JM 83 | pAA152 | B-18155 |
| JM 83 | pAA130 | B-18154 |
| JM 83 | pGD103 | B-18153 |
| JM 103 | pPX163 | B-18285 |
| PR 13 | pPX167 | B-18286 |
| JM 103 | pPX168 | B-18287 |
| JM 103 | pPX183 | B-18377 |
| Jm 103 | pPX199 | B-18530 |
| DH5α | pPX512 | B-18531 |

The present invention is not to be limited in scope by the microorganisms deposited since the deposited embodiment is intended as a single illustration of one aspect of the invention and the many microorganisms which are functionally equivalent are within the scope of the present invention. Indeed, various modifications of the invention in addition to those shown and described herein will become apparent to those skilled in the art from the foregoing description and accompanying figures. Such modifications are intended to fall within the scope of the appended claims.

It is also to be understood that all base pair sizes given for nucleotides are approximate and are used for purposes of description.

What is claimed is:

1. A recombinant vector comprising a DNA sequence coding for an antigenic determinant of an *Haemophilus influenzae* fusion protein having an amino acid sequence comprising (a) the amino acid sequence as depicted in FIG. 11 from amino acid residue 20 to 153 of an *Haemophilus influenzae* PBOMP-1 protein and (b) the amino acid sequence as depicted in FIG. 15 from amino acid residue 19 to 154 of an *Haemophilus influenzae* PBOMP-2 protein.

2. The recombinant vector according to claim 1 in which the vector is pPX183 or a mutant, recombinant or genetically engineered derivative thereof.

3. The recombinant vector according to claim 1, in which the vector is pPX199 or a mutant, recombinant or genetically engineered derivative thereof.

4. The recombinant vector according to claim 1, in which the vector is pPX512 or a mutant, recombinant or genetically engineered derivative thereof.

5. A bacterium containing the recombinant vector of claim 1, comprising an *Escherichia coli* bacterium deposited with the NRRL and assigned the accession No. B-18377.

6. A bacterium containing the recombinant vector of claim 1, comprising an *Escherichia coli* bacterium deposited with the NRRL and assigned the accession No. B-18530.

7. A bacterium containing the recombinant vector of claim 1, comprising an *Escherichia coli* bacterium deposited with the NRRL and assigned the accession No. B-18531.

8. A recombinant vector, comprising a DNA sequence coding for an antigenic determinant of an *Haemophilus influenzae* outer membrane protein having the amino acid sequence as depicted in FIG. 11 from amino acid residue 20 to 153 of an *Haemophilus influenzae* PBOMP-1 protein.

9. A recombinant vector, comprising a DNA sequence coding for an antigenic determinant of an *Haemophilus influenzae* outer membrane protein having the amino acid sequence as depicted in FIG. 15 from amino acid residue 19 to 154 of an *Haemophilus influenzae* PBOMP-2 protein.

10. The recombinant vector according to claim 8, in which the vector is pAA152 or a mutant, recombinant or genetically engineered derivative thereof.

11. The recombinant vector according to claim 8, in which the vector is pPX167 or a mutant, recombinant or genetically engineered derivative thereof.

12. The recombinant vector according to claim 8, in which the vector is pPX168 or a mutant, recombinant or genetically engineered derivative thereof.

13. The recombinant vector according to claim 9, in which the vector is pAA130 or a mutant, recombinant or genetically engineered derivative thereof.

14. The recombinant vector according to claim 9, in which the vector is pPX163 or a mutant, recombinant or genetically engineered derivative thereof.

15. A bacterium containing the recombinant vector of claim 8, comprising an *Escherichia coli* bacterium deposited with the NRRL and assigned accession No. B-18155.

16. A bacterium containing the recombinant vector of claim 8, comprising an *Escherichia coli* bacterium deposited with the NRRL and assigned accession No. B-18286.

17. A bacterium containing the recombinant vector of claim 8, comprising an *Escherichia coli* bacterium deposited with the NRRL and assigned accession No. B-18287.

18. A bacterium containing the recombinant vector of claim 9, comprising an *Escherichia coli* bacterium deposited with the NRRL and assigned accession No. B-18154.

19. A bacterium containing the recombinant vector of claim 9, comprising an *Escherichia coli* bacterium deposited with the NRRL and assigned accession No. B-18285.

* * * * *